US012673963B2

(12) United States Patent
Heyes et al.

(10) Patent No.: US 12,673,963 B2
(45) Date of Patent: Jul. 7, 2026

(54) CATIONIC LIPIDS FOR LIPID NANOPARTICLE DELIVERY OF THERAPEUTICS TO HEPATIC STELLATE CELLS

(71) Applicant: GENEVANT SCIENCES GMBH, Basel (CH)

(72) Inventors: James Heyes, Vancouver (CA); Kieu Mong Lam, Burnaby (CA); Richard J. Holland, Vancouver (CA); Wenxuan Zhang, Burnaby (CA)

(73) Assignee: GENEVANT SCIENCES GMBH, Basel (CH)

( * ) Notice: Subject to any disclaimer, the term of this patent is extended or adjusted under 35 U.S.C. 154(b) by 915 days.

(21) Appl. No.: 17/797,760

(22) PCT Filed: Feb. 11, 2021

(86) PCT No.: PCT/US2021/017676

§ 371 (c)(1),
(2) Date: Aug. 5, 2022

(87) PCT Pub. No.: WO2021/163339

PCT Pub. Date: Aug. 19, 2021

(65) Prior Publication Data

US 2023/0139594 A1 May 4, 2023

Related U.S. Application Data

(60) Provisional application No. 62/975,116, filed on Feb. 11, 2020.

(51) Int. Cl.

| | |
|---|---|
| ***C07F 7/18*** | (2006.01) |
| ***A61K 9/14*** | (2006.01) |
| ***A61K 31/695*** | (2006.01) |
| ***A61K 31/7105*** | (2006.01) |
| ***A61K 31/713*** | (2006.01) |
| ***A61K 45/06*** | (2006.01) |
| ***A61K 47/24*** | (2006.01) |
| ***A61K 47/54*** | (2017.01) |
| ***A61P 1/16*** | (2006.01) |
| ***C12N 15/113*** | (2010.01) |
| ***C12N 15/88*** | (2006.01) |

(52) U.S. Cl.

CPC ............ *C07F 7/1804* (2013.01); *A61K 9/145* (2013.01); *A61K 47/24* (2013.01); *A61K 47/543* (2017.08); *C12N 15/1137* (2013.01); *C12N 15/88* (2013.01); *C12N 2310/141* (2013.01); *C12N 2310/321* (2013.01)

(58) Field of Classification Search

CPC ..... C07F 7/1804; A61K 9/145; A61K 31/695; A61K 31/713; A61K 31/7105; A61K 45/06; A61K 47/6929; A61P 1/16

See application file for complete search history.

(56) References Cited

U.S. PATENT DOCUMENTS

| | | | | |
|---|---|---|---|---|
| 2,713,064 | A | 7/1955 | Weyenberg | |
| 3,029,269 | A | 4/1962 | Abbott et al. | |
| 3,810,843 | A * | 5/1974 | Slusarczuk et al. | C01B 33/146 106/490 |
| 4,176,124 | A | 11/1979 | Darms et al. | |
| 4,271,074 | A | 6/1981 | Lohmann et al. | |
| 4,329,486 | A | 5/1982 | Knollmueller | |
| 8,058,069 | B2 | 11/2011 | Yaworski et al. | |
| 8,492,359 | B2 | 7/2013 | Yaworski et al. | |
| 8,822,668 | B2 | 9/2014 | Yaworski et al. | |
| 9,006,417 | B2 | 4/2015 | Yaworski et al. | |
| 9,364,435 | B2 | 6/2016 | Yaworski et al. | |
| 9,404,127 | B2 | 8/2016 | Yaworski et al. | |
| 9,504,651 | B2 | 11/2016 | Maclachlan et al. | |
| 9,518,272 | B2 | 12/2016 | Yaworski et al. | |
| 11,141,378 | B2 | 10/2021 | Yaworski et al. | |
| 2019/0161506 | A1 | 5/2019 | Roeben et al. | |

FOREIGN PATENT DOCUMENTS

| | | | |
|---|---|---|---|
| CN | 102911401 | B | 4/2014 |
| CN | 108239103 | B | 9/2020 |
| DE | 1180359 | B | 10/1964 |
| EP | 1783781 | A2 | 5/2007 |
| EP | 2177562 | A2 | 4/2010 |
| GB | 709345 | A | 5/1954 |
| GB | 1210510 | A | 10/1970 |
| JP | S54-52062 | A | 4/1979 |
| JP | H04161459 | A | 6/1992 |
| JP | H09132609 | A | 5/1997 |
| JP | 2009132855 | A | 6/2009 |
| JP | 2009209311 | A | 9/2009 |
| JP | 2017197455 | A | 11/2017 |
| WO | 2008041976 | A2 | 4/2008 |

(Continued)

OTHER PUBLICATIONS

CAS Registry Ro.: 18828-83-6 (Entered STN date: Nov. 16, 1984). (Year: 1984).*
CAS Registry RN 2279074-81-4 (Entered STN: Mar. 5, 2019). (Year: 2019).*
STN CAPlus result of US-3810843-A. Retrieved on Jan. 30, 2026. (Year: 2026).*
Abbott, A, et al., "Silicate Esters and Related Compounds", Journal of Chemical and Engineering Data 6 (3), 437-442 (1961).
Kaufman, H , et al., "Properties of Several Arylated Silicon Compounds", Journal of Chemical and Engineering Data 7 (4), 556-558 (1962).
CAS Registry No. 18882-16-1, Entered STN: Nov. 16, 1984; 2 pages.
CAS Registry No. 18822-22-5, Entered STN: Nov. 16, 1984; 2 pages.

(Continued)

*Primary Examiner* — Kamal A Saeed
*Assistant Examiner* — Sagar Patel
(74) *Attorney, Agent, or Firm* — Kilpatrick Townsend & Stockton LLP

(57) ABSTRACT

Certain embodiments of the invention provide lipids useful for preparing lipid nanoparticles for delivering therapeutic agents to, e.g., hepatic stellate cells.

30 Claims, 4 Drawing Sheets

Specification includes a Sequence Listing.

(56) References Cited

FOREIGN PATENT DOCUMENTS

| | | | |
|---|---|---|---|
| WO | 2008041976 | A3 | 7/2008 |
| WO | 2010088537 | A2 | 8/2010 |
| WO | 2011153493 | A2 | 12/2011 |
| WO | 2012/166949 | | 12/2012 |
| WO | 2015130584 | A2 | 9/2015 |
| WO | 2015199952 | A1 | 12/2015 |
| WO | 2016010840 | A1 | 1/2016 |
| WO | 2017/205566 | A1 | 11/2017 |
| WO | 2018081480 | A1 | 5/2018 |
| WO | 2019089828 | A1 | 5/2019 |
| WO | 2019123263 | A2 | 6/2019 |
| WO | 2019123263 | A3 | 11/2019 |
| WO | 2020010059 | A1 | 1/2020 |
| WO | 2022133344 | A1 | 6/2022 |

OTHER PUBLICATIONS

CAS Registry No. 18825-57-5, Entered STN: Nov. 16, 1984; 2 pages.

CAS Registry No. 18828-83-6, Entered STN: Nov. 16, 1984; 2 pages.

CAS Registry No. 18862-05-0, Entered STN: Nov. 16, 1984; 2 pages.

CAS Registry No. 18876-60-3, Entered STN: Nov. 16, 1984; 2 pages.

Patent Cooperation Treaty , International Search Report and Written Opinion for PCT/US2021/017676, 10 bages, dated Jun. 23, 2021.

Planelles-Arago, J , et al., “New insights on organosilane oligomerization mechanisms using ESI-MS and 29Si NMR”, New Journal of Chemistry 33, 1100-1108 (2009).

PUBCHEM , “Trioctoxy(3-trioctoxysilylpropyl)silane”, CID 20761013, 8 pages (Create date Dec. 5, 2007; Modify date Apr. 3, 2021).

Love, K.T. et al., “Lipid-like materials for low-dose, in vivo gene silencing,” PNAS, Jan. 11, 2010, vol. 107, No. 5, pp. 1864-1869.

Intellectual Property Office of Singapore, Application No. SG11202252019M, Search Report and Written Opinion mailed Nov. 14, 2025, 7 pages.

European Patent Application No. 21753059.1, Extended European Search Report, Apr. 3, 2024, 10 pages.

* cited by examiner

SEQUENCE LISTING

```
<160> NUMBER OF SEQ ID NOS: 7

<210> SEQ ID NO 1
<211> LENGTH: 21
<212> TYPE: RNA
```

-continued

<213> ORGANISM: Artificial Sequence
<220> FEATURE:
<223> OTHER INFORMATION: The sequence is artificially synthesized
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(19)
<223> OTHER INFORMATION: um
<220> FEATURE:
<221> NAME/KEY: modified_base
<222> LOCATION: (20)..(21)
<223> OTHER INFORMATION: Phosphorothioate linkage
<220> FEATURE:
<221> NAME/KEY: modified_base
<222> LOCATION: (20)..(21)
<223> OTHER INFORMATION: Deoxythymidine

<400> SEQUENCE: 1
ggucucaagc cacucguuuu u 21

<210> SEQ ID NO 2
<211> LENGTH: 21
<212> TYPE: RNA
<213> ORGANISM: Artificial Sequence
<220> FEATURE:
<223> OTHER INFORMATION: The sequence is artificially synthesized
<220> FEATURE:
<221> NAME/KEY: modified_base
<222> LOCATION: (20)..(21)
<223> OTHER INFORMATION: Deoxythymidine
<220> FEATURE:
<221> NAME/KEY: modified_base
<222> LOCATION: (20)..(21)
<223> OTHER INFORMATION: Phosphorothioate linkage

<400> SEQUENCE: 2
aaacgagugg cuugagaccu u 21

<210> SEQ ID NO 3
<211> LENGTH: 21
<212> TYPE: RNA
<213> ORGANISM: Artificial Sequence
<220> FEATURE:
<223> OTHER INFORMATION: The sequence is artificially synthesized
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (16)..(16)
<223> OTHER INFORMATION: um

<400> SEQUENCE: 3
gagacacaug ggugcuauug u 21

<210> SEQ ID NO 4
<211> LENGTH: 21
<212> TYPE: RNA
<213> ORGANISM: Artificial Sequence
<220> FEATURE:
<223> OTHER INFORMATION: The sequence is artificially synthesized
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (18)..(18)
<223> OTHER INFORMATION: um

<400> SEQUENCE: 4
aauagcaccc augugucuca g 21

<210> SEQ ID NO 5
<211> LENGTH: 100
<212> TYPE: RNA
<213> ORGANISM: Artificial Sequence
<220> FEATURE:
<223> OTHER INFORMATION: The sequence is artificially synthesized
<220> FEATURE:
<221> NAME/KEY: variation
<222> LOCATION: (100)..(100)
<223> OTHER INFORMATION: A nucleotide can be repeated up to one hundred fifty times

<400> SEQUENCE: 5
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa 100

<210> SEQ ID NO 6
<211> LENGTH: 30
<212> TYPE: RNA
<213> ORGANISM: Artificial Sequence
<220> FEATURE:
<223> OTHER INFORMATION: The sequence is artificially synthesized
<220> FEATURE:

-continued

<221> NAME/KEY: variation
<222> LOCATION: (30)..(30)
<223> OTHER INFORMATION: A nucleotide can be repeated one or more times

<400> SEQUENCE: 6
aaaaaaaaaa aaaaaaaaaa aaaaaaaaaa 30

<210> SEQ ID NO 7
<211> LENGTH: 35
<212> TYPE: RNA
<213> ORGANISM: Artificial Sequence
<220> FEATURE:
<223> OTHER INFORMATION: The sequence is artificially synthesized
<220> FEATURE:
<221> NAME/KEY: variation
<222> LOCATION: (35)..(35)
<223> OTHER INFORMATION: A nucleotide can be repeated up to two thousand nine hundred sixty five times

<400> SEQUENCE: 7
aaaaaaaaaa aaaaaaaaaa aaaaaaaaaa aaaaa 35

CATIONIC LIPIDS FOR LIPID NANOPARTICLE DELIVERY OF THERAPEUTICS TO HEPATIC STELLATE CELLS

CROSS-REFERENCE TO RELATED APPLICATION(S)

This patent application is a national stage entry under 35 U.S.C. § 371 of International Patent Application No. PCT/US2021/017676, filed Feb. 11, 2021, which claims the benefit of priority of U.S. Provisional Application No. 62/975,116, filed Feb. 11, 2020.

SEQUENCE LISTING

This application contains a Sequence Listing which has been submitted electronically in ASCII text format to comply with WIPO Standard ST.25 and is hereby incorporated by reference in its entirety. Said text copy, created on Mar. 16, 2026, is named 104290-G00810US-1455301_ST25.txt, and is 3596 bytes in size.

BACKGROUND

Cationic lipid-containing nanoparticles have been used for the delivery of a variety of therapeutic agents. Currently, the difficulty and cost associated with the preparation of the cationic lipid component of these nanoparticles can limit their attractiveness for commercial development as delivery vehicles. Accordingly, there is a need for additional cationic lipids that can be incorporated into lipid nanoparticles. For example, there is a need for cationic lipids that can be prepared using less expensive and more efficient processes. There is also a need for cationic lipids that are relatively more biodegradable, such that the related lipid nanoparticles better degrade following delivery of an active agent or a therapeutic agent. There is also a need for lipid nanoparticle with characteristics for delivering therapeutic agents to hepatic stellate cells for the treatment, e.g., of liver fibrosis.

SUMMARY

The invention provides cationic lipids that are effective for delivering an active agent or therapeutic agent, such as a nucleic acid, when incorporated into lipid nanoparticles to hepatic stellate cells. The cationic lipids are also biodegradable, such that associated lipid nanoparticles better degrade following delivery of an active agent or a therapeutic agent.

Accordingly, in certain embodiments, provided herein a compound of formula (I):

(I)

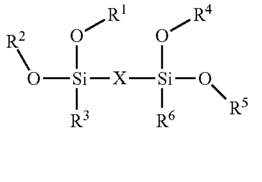

wherein:

$R^1$ is a $C_2$-$C_{30}$ hydrocarbyl;

$R^2$ is a $C_2$-$C_{30}$ hydrocarbyl;

$R^3$ is $C_1$-$C_4$ alkyl or —O—$C_2$-$C_{30}$ hydrocarbyl;

$R^4$ is a $C_2$-$C_{30}$ hydrocarbyl;

$R^5$ is a $C_2$-$C_{30}$ hydrocarbyl;

$R^6$ is $C_1$-$C_4$ alkyl or —O—$C_2$-$C_{30}$ hydrocarbyl; and

X is a divalent linking group.

Also provided are lipid particle comprising such compounds, and for methods of using the lipid particles, e.g., to deliver therapeutics specifically to hepatic stellate cells to treat diseases.

DETAILED DESCRIPTION

Figure 1:
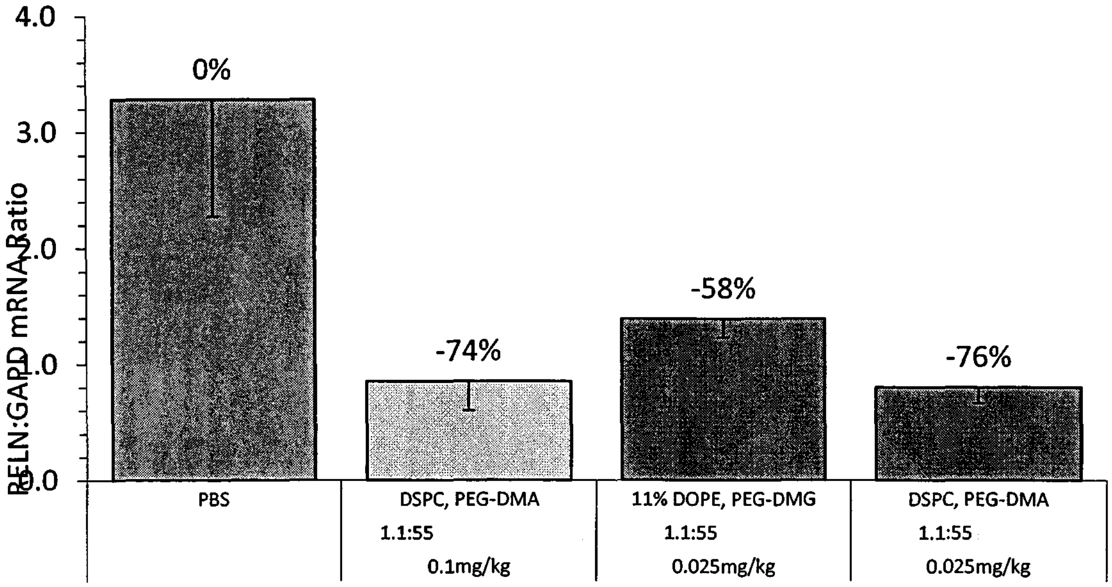
FIG. 1 depicts reelin mRNA knock-down 48 hours following IV administration of the LNP formulations in Balb/C Mice (n=4). LNP with a representative compound of the invention (presented in columns 3 and 4) has equivalent potency to a benchmark compound (100; presented in column 2), but at 4-times lower dose (0.025 mg/kg instead of 0.1 mg/kg).

In certain embodiments, provided herein is a compound of formula (I):

(I)

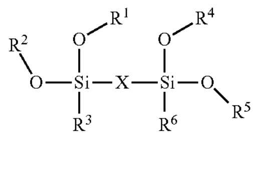

wherein:

$R^1$ is a $C_2$-$C_{30}$ hydrocarbyl;

$R^2$ is a $C_2$-$C_{30}$ hydrocarbyl;

$R^3$ is $C_1$-$C_4$ alkyl or —O—$C_2$-$C_{30}$ hydrocarbyl;

$R^4$ is a $C_2$-$C_{30}$ hydrocarbyl;

$R^5$ is a $C_2$-$C_{30}$ hydrocarbyl;

$R^6$ is $C_1$-$C_4$ alkyl or —O—$C_2$-$C_{30}$ hydrocarbyl; and

X is a divalent linking group.

In certain embodiments, $R^1$ is $C_2$-$C_{20}$ hydrocarbyl.

In certain embodiments, $R^1$ is $C_2$-$C_{15}$ hydrocarbyl.

In certain embodiments, $R^1$ is $C_2$-$C_{10}$ hydrocarbyl.

In certain embodiments, $R^1$ is $C_5$-$C_{20}$ hydrocarbyl.

In certain embodiments, $R^1$ is ($C_2$-$C_{20}$)alkyl, ($C_2$-$C_{20}$) alkenyl, or ($C_2$-$C_{20}$)alkynyl.

In certain embodiments, $R^1$ is ($C_7$-$C_{15}$)alkyl.

In certain embodiments, $R^1$ is ($C_7$-$C_{15}$)alkenyl.

In certain embodiments, $R^1$ is ($C_7$-$C_{15}$)alkynyl.

In certain embodiments, $R^1$ is ($C_7$-$C_{15}$)alkenyl, having only one double bond.

In certain embodiments, $R^1$ is (Z)-4-decen-1-yl, 1-tridecyl, (Z)-3-hept-1-yl, or (Z)-5-dodecen-1-yl.

In certain embodiments, $R^2$ is $C_2$-$C_{20}$ hydrocarbyl.

In certain embodiments, $R^2$ is $C_2$-$C_{15}$ hydrocarbyl.

In certain embodiments, $R^2$ is $C_2$-$C_{10}$ hydrocarbyl.

In certain embodiments, $R^2$ is $C_5$-$C_{20}$ hydrocarbyl.

In certain embodiments, $R^2$ is ($C_2$-$C_{20}$)alkyl, ($C_2$-$C_{20}$) alkenyl, or ($C_2$-$C_{20}$)alkynyl.

In certain embodiments, $R^2$ is a ($C_7$-$C_{15}$)alkyl.

In certain embodiments, $R^2$ is a ($C_7$-$C_{15}$)alkenyl.

In certain embodiments, $R^2$ is a ($C_7$-$C_{15}$)alkynyl.

In certain embodiments, $R^2$ is a ($C_7$-$C_{15}$)alkenyl, having only one double bond.

In certain embodiments, $R^2$ is (Z)-4-decen-1-yl, 1-tridecyl, (Z)-3-hept-1-yl, or (Z)-5-dodecen-1-yl.

In certain embodiments, $R^3$ is $C_1$-$C_4$ alkyl.

In certain embodiments, $R^3$ is methyl.

In certain embodiments, $R^3$ is —O—$C_2$-$C_{20}$ hydrocarbyl.

In certain embodiments, $R^3$ is —O—$C_2$-$C_{15}$ hydrocarbyl.

In certain embodiments, $R^3$ is —O—$C_2$-$C_{10}$ hydrocarbyl.

In certain embodiments, $R^3$ is —O—$C_5$-$C_{20}$ hydrocarbyl.

In certain embodiments, $R^3$ is —O—($C_2$-$C_{20}$)alkyl, —O—($C_2$-$C_{20}$)alkenyl, or —O—($C_2$-$C_{20}$)alkynyl.

In certain embodiments, $R^3$ is a —O—($C_7$-$C_{15}$)alkyl.

In certain embodiments, $R^3$ is a —O—($C_7$-$C_{15}$)alkenyl.

In certain embodiments, $R^3$ is a —O—($C_7$-$C_{15}$)alkynyl.

In certain embodiments, $R^3$ is a —O—($C_7$-$C_{15}$)alkenyl, having only one double bond.

In certain embodiments, $R^3$ is (Z)-4-decen-1-yloxy, 1-tridecyloxy, (Z)-3-hept-1-yloxy, or (Z)-5-dodecen-1-yloxy.

In certain embodiments, $R^4$ is $C_2$-$C_{20}$ hydrocarbyl.

In certain embodiments, $R^4$ is $C_2$-$C_{15}$ hydrocarbyl.

In certain embodiments, $R^4$ is $C_2$-$C_{10}$ hydrocarbyl.

In certain embodiments, $R^4$ is $C_5$-$C_{20}$ hydrocarbyl.

In certain embodiments, $R^4$ is ($C_2$-$C_{20}$)alkyl, ($C_2$-$C_{20}$) alkenyl, or ($C_2$-$C_{20}$)alkynyl.

In certain embodiments, $R^4$ is ($C_7$-$C_{15}$)alkyl.

In certain embodiments, $R^4$ is ($C_7$-$C_{15}$)alkenyl.

In certain embodiments, $R^4$ is ($C_7$-$C_{15}$)alkynyl.

In certain embodiments, $R^4$ is ($C_7$-$C_{15}$)alkenyl, having only one double bond.

In certain embodiments, $R^4$ is (Z)-4-decen-1-yl, 1-tridecyl, (Z)-3-hept-1-yl, or (Z)-5-dodecen-1-yl.

In certain embodiments, $R^5$ is $C_2$-$C_{20}$ hydrocarbyl.

In certain embodiments, $R^5$ is $C_2$-$C_{15}$ hydrocarbyl.

In certain embodiments, $R^5$ is $C_2$-$C_{10}$ hydrocarbyl.

In certain embodiments, $R^5$ is $C_5$-$C_{20}$ hydrocarbyl.

In certain embodiments, $R^5$ is ($C_2$-$C_{20}$)alkyl, ($C_2$-$C_{20}$) alkenyl, or ($C_2$-$C_{20}$)alkynyl.

In certain embodiments, $R^5$ is a ($C_7$-$C_{15}$)alkyl.

In certain embodiments, $R^5$ is a ($C_7$-$C_{15}$)alkenyl.

In certain embodiments, $R^5$ is a ($C_7$-$C_{15}$)alkynyl.

In certain embodiments, $R^5$ is a ($C_7$-$C_{15}$)alkenyl, having only one double bond.

In certain embodiments, $R^5$ is (Z)-4-decen-1-yl, 1-tridecyl, (Z)-3-hept-1-yl, or (Z)-5-dodecen-1-yl.

In certain embodiments, $R^6$ is $C_1$-$C_4$ alkyl.

In certain embodiments, $R^6$ is methyl.

In certain embodiments, $R^6$ is —O—$C_2$-$C_{20}$ hydrocarbyl.

In certain embodiments, $R^6$ is —O—$C_2$-$C_{15}$ hydrocarbyl.

In certain embodiments, $R^6$ is —O—$C_2$-$C_{10}$ hydrocarbyl.

In certain embodiments, $R^6$ is —O—$C_5$-$C_{20}$ hydrocarbyl.

In certain embodiments, $R^6$ is —O—($C_2$-$C_{20}$)alkyl, —O—($C_2$-$C_{20}$)alkenyl, or —O—($C_2$-$C_{20}$)alkynyl.

In certain embodiments, $R^6$ is a —O—($C_7$-$C_{15}$)alkyl.

In certain embodiments, $R^6$ is a —O—($C_7$-$C_{15}$)alkenyl.

In certain embodiments, $R^6$ is a —O—($C_7$-$C_{15}$)alkynyl.

In certain embodiments, $R^6$ is a —O—($C_7$-$C_{15}$)alkenyl, having only one double bond.

In certain embodiments, $R^6$ is (Z)-4-decen-1-yloxy, 1-tridecyloxy, (Z)-3-hept-1-yloxy, or (Z)-5-dodecen-1-yloxy.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), (—$NR^a$—), (a divalent ($C_3$-$C_8$)cycloalkyl), or (a divalent 3-12 membered heterocycle), and wherein the chain, the divalent ($C_3$-$C_8$)cycloalkyl, or the divalent 3-12 membered heterocycle is optionally substituted with one or more (e.g. 1, 2, 3, or 4) substituents independently selected from the group consisting of ($C_1$-$C_6$)alkoxy, ($C_1$-$C_6$)alkanoyl, ($C_1$-$C_6$)alkanoyloxy, ($C_1$-$C_6$)alkoxycarbonyl, cyano, nitro, halo, hydroxy, oxo (═O), and carboxy; and wherein each $R^a$ is independently selected from H and ($C_1$-$C_6$)alkyl that is optionally substituted with one or more groups independently selected from halo, hydroxy, and ($C_1$-$C_6$)alkoxy.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), (—$NR^a$—), (a divalent ($C_3$-$C_8$)cycloalkyl), or (a divalent 3-8 membered heterocycle), and wherein the chain, the divalent ($C_3$-$C_8$)cycloalkyl, or the divalent 3-8 membered heterocycle is optionally substituted with one or more (e.g. 1, 2, 3, or 4) substituents independently selected from the group consisting of ($C_1$-$C_6$)alkoxy, ($C_1$-$C_6$)alkanoyl, ($C_1$-$C_6$)alkanoyloxy, ($C_1$-$C_6$)alkoxycarbonyl, cyano, nitro, halo, hydroxy, oxo (═O), and carboxy; and wherein each $R^a$ is independently selected from H and ($C_1$-$C_6$)alkyl.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—$NR^a$—) or (a divalent 3-12 membered heterocycle); and wherein each $R^a$ is independently selected from ($C_1$-$C_6$) alkyl that is optionally substituted with one or more groups independently selected from halo, hydroxy, and ($C_1$-$C_6$) alkoxy.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—$NR^a$—) or (a divalent 3-8 membered heterocycle); and wherein each $R^a$ is independently selected from ($C_1$-$C_6$) alkyl.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is replaced by (—$NR^a$—); and wherein each $R^a$ is independently selected from ($C_1$-$C_6$)alkyl that is optionally substituted with one or more groups independently selected from halo, hydroxy, and ($C_1$-$C_6$)alkoxy.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is replaced by (—$NR^a$—); and wherein each $R^a$ is independently selected from ($C_1$-$C_6$)alkyl.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by a divalent 3-12 membered heterocycle.

In certain embodiments, X is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by a divalent 3-8 membered heterocycle.

In certain embodiments, X is a divalent, branched or unbranched, saturated or unsaturated, hydrocarbon chain, having from 6 to 12 carbon atoms, wherein one or more (e.g. 1, 2, 3, or 4) of the carbon atoms is optionally replaced by a piperazin-1,4-diyl.

In certain embodiments, X is selected from the group consisting of:

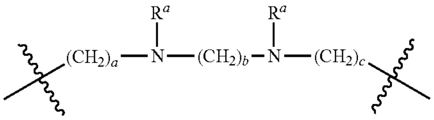

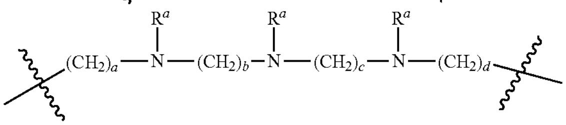

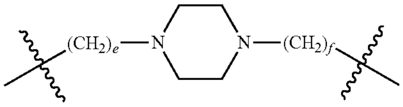

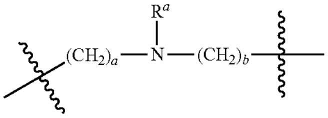

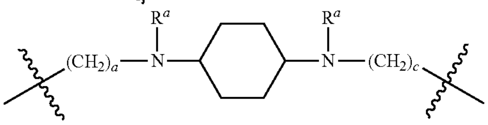

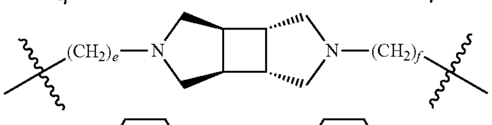

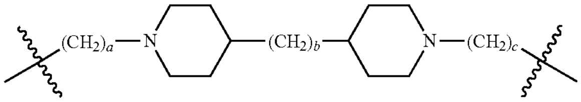

-continued

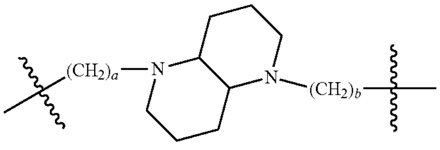

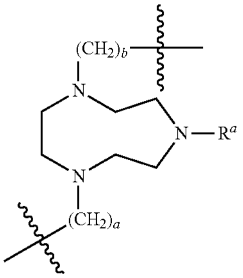

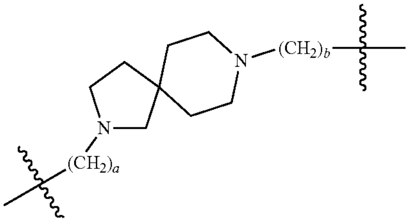

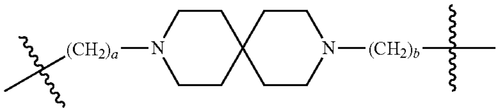

and

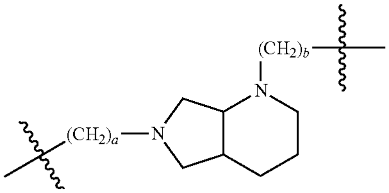

wherein:

a is 2, 3, 4, or 5;

b is 2, 3, 4, or 5;

c is 2, 3, 4, or 5;

d is 2, 3, 4, or 5;

e is 2, 3, 4, 5, 6, 7, or 8;

f is 2, 3, 4, 5, 6, 7, or 8; and each $R^a$ is independently selected from H and ($C_1$-$C_6$) alkyl that is optionally substituted with one of more groups independently selected from halo, hydroxy, and ($C_1$-$C_6$)alkoxy.

In certain embodiments, X is selected from the group consisting of:

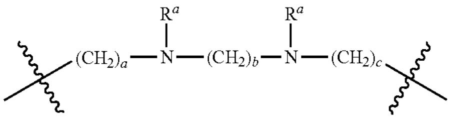

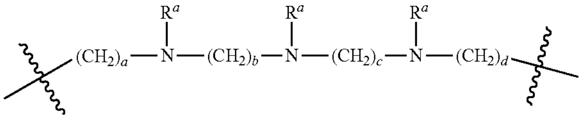

-continued
and 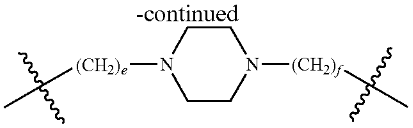
wherein:
a is 2, 3, 4, or 5;
b is 2, 3, 4, or 5;
c is 2, 3, 4, or 5;
d is 2, 3, 4, or 5;
e is 2, 3, 4, 5, 6, 7, or 8;
f is 2, 3, 4, 5, 6, 7, or 8; and
each $R^a$ is independently selected from H and ($C_1$-$C_6$) alkyl.
In certain embodiments, X is selected from the group consisting of:
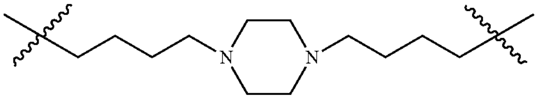
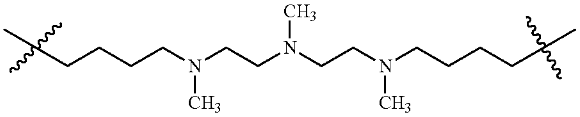
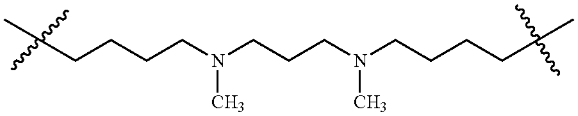
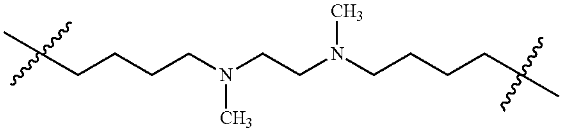
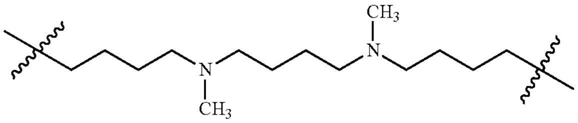
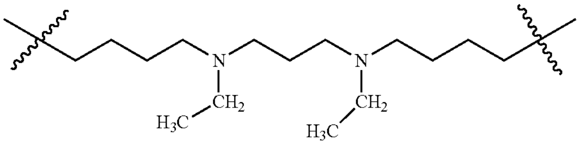
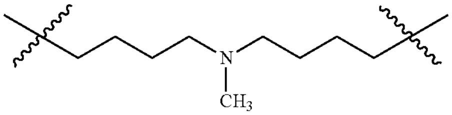
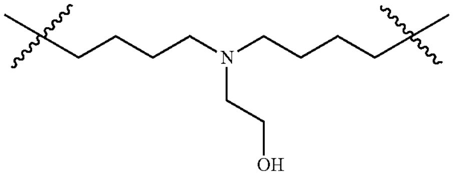
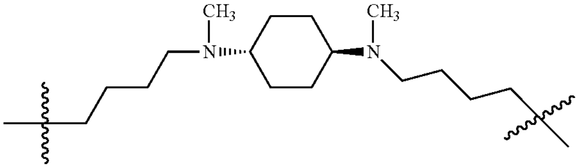
-continued
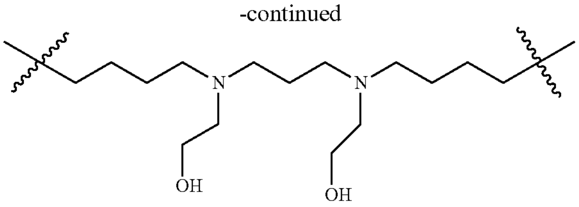
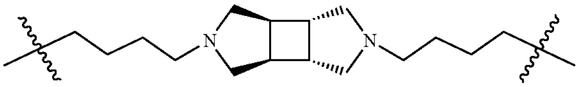
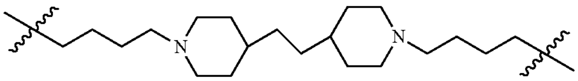
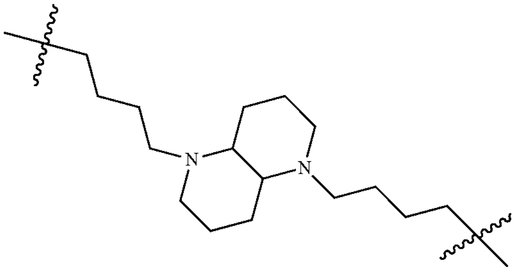
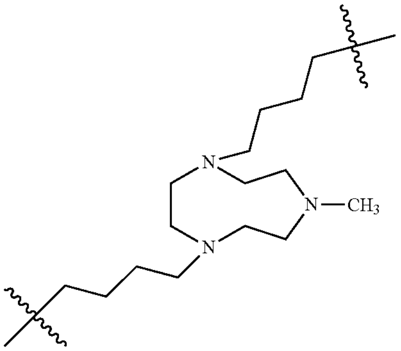
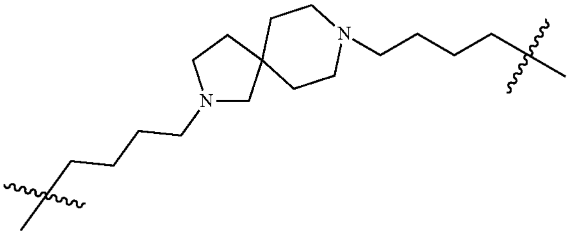
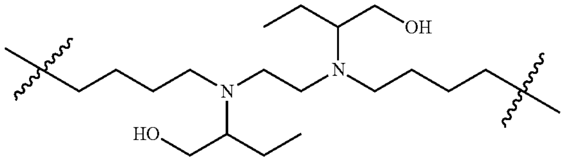
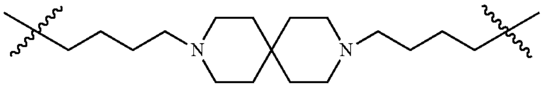
and
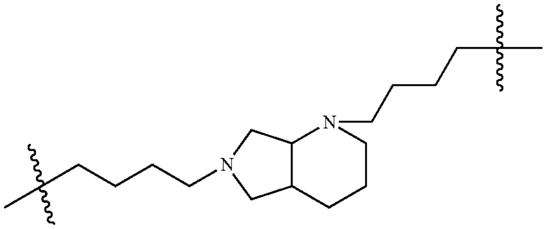
.

In certain embodiments, X is selected from the group consisting of:

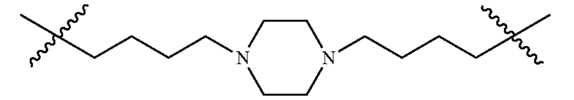

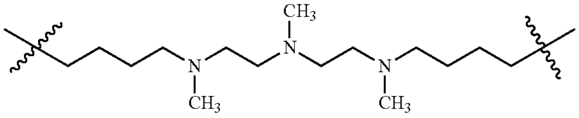

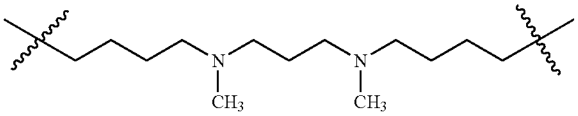

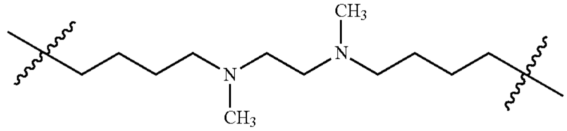

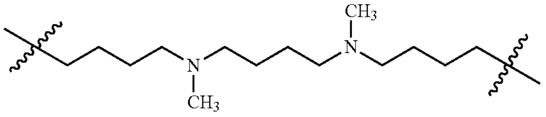

and

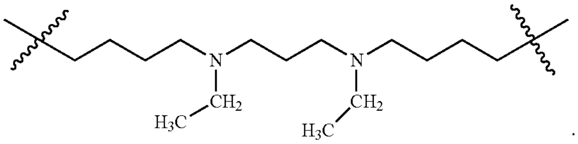

.

In certain embodiments, the compound is selected from a compound as described in the Examples, e.g., a compound of formula any one of compounds 2-42, e.g., 2-30.

Also provided herein are lipid particles comprising a compound as described herein.

In certain embodiments, the lipid particle further comprises a non-cationic lipid.

In certain embodiments, the lipid particle further comprises a conjugated lipid that inhibits aggregation of particles.

In certain embodiments, the lipid particle further comprises a therapeutic agent.

In certain embodiments, the therapeutic agent is a nucleic acid therapeutic agent.

In certain embodiments, the therapeutic agent is an interfering RNA agent.

In certain embodiments, the therapeutic agent is siRNA.

In certain embodiments, the therapeutic agent is mRNA.

In certain embodiments, the nucleic acid therapeutic agent comprises at least one modified nucleotide.

In certain embodiments, the nucleic acid comprises at least one 2'-O-methyl (2'OMe) nucleotide.

In certain embodiments, the non-cationic lipid is cholesterol or a derivative thereof.

In certain embodiments, the non-cationic lipid is cholesterol.

In certain embodiments, the non-cationic lipid comprises a phospholipid.

In certain embodiments, the non-cationic lipid comprises a mixture of a phospholipid and cholesterol.

In certain embodiments, the phospholipid is distearoylphosphatidylcholine (DSPC).

In certain embodiments, the conjugated lipid is a polyethyleneglycol (PEG)-lipid conjugate.

In certain embodiments, the PEG-lipid conjugate is a PEG-dimyristyloxypropyl (PEG-DMA) conjugate.

Also provided herein are compositions comprising a compound or lipid particle as described herein.

Also provided herein are pharmaceutical compositions comprising a compound or lipid particle as described herein, and a pharmaceutically acceptable carrier.

Also provided is a method for the in vivo delivery of a therapeutic agent, the method comprising: administering to a mammalian subject a lipid particle as described herein.

Also provided is a lipid particle as described herein for use in the in vivo delivery of a therapeutic agent to a mammal.

Also provided is the use of a lipid particle as described herein to prepare a medicament for the in vivo delivery of a therapeutic agent to a mammal.

Also provided is a method for treating a disease or disorder in a mammalian subject in need thereof, the method comprising administering to the mammalian subject a therapeutically effective amount of a lipid particle as described herein.

In certain embodiments, the disease or disorder is liver fibrosis.

In certain embodiments, the disease or disorder is non-alcoholic steatohepatitis (NASH).

In certain embodiments, the disease or disorder is alcoholic steatohepatitis (ASH).

In certain embodiments, the disease or disorder is liver fibrosis associated non-alcoholic steatohepatitis (NASH) or alcoholic steatohepatitis (ASH).

Also provided is a method of delivering a therapeutic agent to a hepatic stellate cell (HSC), in vivo or in vitro, comprising contacting the HSC with the lipid particle as described herein.

Liver fibrosis is caused by excessive accumulation of extracellular matrix during chronic liver injuries. Activation of hepatic stellate cells (HSCs) is a key step during liver fibrogenesis. Targeted delivery of therapeutic agents to HSCs, e.g., activated HSCs, may be important for the successful treatment of liver fibrosis. A number of protein markers have been found to be overexpressed in activated HSCs, and their ligands have been used to specifically deliver various antifibrotic agents. (see, e.g., Chen et al., Journal of Pharmacology and Experimental Therapeutics, 2019, 370 (3) 695-702). However, delivery of therapeutics using other systems, such as lipid nanoparticles (LNPs), is needed as other means for delivering therapeutic agents to HSCs.

Liver fibrosis is caused by the formation of an abnormally large amount of scar tissue in the liver. Liver fibrosis occurs when the liver attempts to repair and replace damaged cells. Various disorders and drugs can damage the liver and cause fibrosis.

Nonalcoholic fatty liver disease (NAFLD) is a condition in which triglycerides accumulate in the liver. Nonalcoholic steatohepatitis (NASH) is a type of NAFLD. NASH is associated with inflammatory changes and liver cell damage. NASH is a leading cause of liver disease and often progresses to liver fibrosis, cirrhosis and hepatocellular carcinoma (HCC). Non-alcoholic steatohepatitis (NASH) and alcoholic steatohepatitis (ASH) have a similar pathogenesis and histopathology but a different etiology and epidemiology. NASH and ASH are advanced stages of non-alcoholic fatty liver disease (NAFLD) and alcoholic fatty liver disease (AFLD). Alcoholic steatohepatitis (ASH) is a chronic, progressive liver disease characterized by fibrosis of the liver as well as possible necrosis of the liver tissue, brought on by excessive, prolonged alcohol use. Women are more susceptible to the disease because alcohol metabolism is lower in women than in men.

Liver fibrosis is an important underlying cause of liver dysfunction and predicts mortality. Progression to cirrhosis and HCC leads to ultimate liver failure and thus liver transplantation is required. The current US prevalence of NASH-related fibrosis (F2 and later) is about 3.8 million patients. Doctors typically recommend weight loss to treat NAFLD and NASH. While weight loss can reduce fat in the liver, inflammation, and fibrosis, no medicines have been approved to treat NAFLD and NASH. Specifically, no medicines have been approved to treat liver fibrosis. (Clin Liver Dis. 2008 November; 12(4):733-46, N Engl J Med. 2017 Nov. 23; 377(21):2063-2072, J Hepatol. 2017 December; 67(6):1265-127) Accordingly, new therapeutic treatment options, included delivery options, are needed for the treatment of liver fibrosis, e.g., in the context of NASH or ASH.

Definitions

As used herein, the following terms have the meanings ascribed to them unless specified otherwise.

Halo or halogen is fluoro, chloro, bromo, or iodo.

Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "hydrocarbyl", by itself or as part of another substituent, means, unless otherwise stated, a straight or branched chain hydrocarbon radical, having the number of carbon atoms designated (e.g., $C_{1-8}$ means one to eight carbons) and optionally having one or more double bonds and/or one or more triple bonds. Thus hydrocarbyl includes alkyl groups, alkenyl groups, and alkynyl groups.

The term "alkyl", by itself or as part of another substituent, means, unless otherwise stated, a straight or branched chain hydrocarbon radical, having the number of carbon atoms designated (e.g., $C_{1-20}$ means one to twenty carbons). Examples include ($C_1$-$C_{20}$)alkyl, ($C_2$-$C_{20}$)alkyl, ($C_5$-$C_{20}$)alkyl, ($C_5$-$C_{15}$)alkyl and ($C_{10}$-$C_{20}$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "cycloalkyl" refers to a saturated or partially unsaturated (non-aromatic) all carbon ring having 3 to 8 carbon atoms (e.g., ($C_3$-$C_8$)carbocycle).

The term "heterocycle" refers to a single saturated or partially unsaturated ring that has at least one atom other than carbon in the ring, wherein the atom is selected from the group consisting of oxygen, nitrogen and sulfur. Thus, the term includes single saturated or partially unsaturated rings (e.g., 3, 4, 5, 6, 7, or 8-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl, piperazinyl, and piperidinyl.

The term "alkoxycarbonyl" as used herein refers to a group (alkyl)-O—C(═O)—, wherein the term alkyl has the meaning defined herein.

The term "alkanoyloxy" as used herein refers to a group (alkyl)-C(═O)—O—, wherein the term alkyl has the meaning defined herein.

As used herein, the term "heteroatom" is meant to include oxygen (O), nitrogen (N), sulfur (S) and silicon (Si).

As used herein a wavy line "〰" that intersects a bond in a chemical structure indicates the point of attachment of the bond that the wavy bond intersects in the chemical structure to the remainder of a molecule.

The term "interfering RNA" or "RNAi" or "interfering RNA sequence" refers to single-stranded RNA (e.g., mature miRNA) or double-stranded RNA (i.e., duplex RNA such as siRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA,* 99:9942-9947 (2002); Calegari et al., *Proc. Natl. Acad. Sci. USA,* 99:14236 (2002); Byrom et al., *Ambion TechNotes,* 10(1):4-6 (2003); Kawasaki et al., *Nucleic Acids Res.,* 31:981-987 (2003); Knight et al., *Science,* 293:2269-2271 (2001); and Robertson et al., *J. Biol. Chem.,* 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA, aiRNA, miRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

An "effective amount" or "therapeutically effective amount" of an active agent or therapeutic agent such as a nucleic acid (e.g., an interfering RNA or mRNA) is an amount sufficient to produce the desired effect, e.g., an inhibition of expression of a target sequence in comparison to the normal expression level detected in the absence of an interfering RNA; or mRNA-directed expression of an amount of a protein that causes a desirable biological effect in the organism within which the protein is expressed. Inhibition of expression of a target gene or target sequence is achieved when the value obtained with an interfering RNA relative to the control is about 90%, 85%, 80%, 75%, 70%, 65%, 60%, 55%, 50%, 45%, 40%, 35%, 30%, 25%, 20%, 15%, 10%, 5%, or 0%. In other embodiments, the expressed protein is an active form of a protein that is normally expressed in a cell type within the body, and the therapeutically effective amount of the mRNA is an amount that produces an amount of the encoded protein that is at least 50% (e.g., at least 60%, or at least 70%, or at least 80%, or at least 90%) of the amount of the protein that is normally expressed in the cell type of a healthy individual. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, or IL-12) by a responder cell in vitro or a decrease in cytokine production in the sera of a mammalian subject after administration of the interfering RNA.

By "decrease," "decreasing," "reduce," or "reducing" of an immune response by an mRNA is intended to mean a detectable decrease of an immune response to a given mRNA (e.g., a modified mRNA). The amount of decrease of an immune response by a modified mRNA may be determined relative to the level of an immune response in the presence of an unmodified mRNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified mRNA. A decrease in the immune response to mRNA is typically measured by a decrease in cytokine production (e.g., IFNγ, IFNα, TNFα, IL-6, or IL-12) by a responder cell in vitro or a decrease in cytokine production in the sera of a mammalian subject after administration of the mRNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-10, IL-12, IL-13, TGF, and combinations thereof.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity.

Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications,* Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (e.g., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.,* 2:482 (1981), by the homology alignment algorithm of Needleman and Wunsch, *J. Mol. Biol.,* 48:443 (1970), by the search for similarity method of Pearson and Lipman, *Proc. Natl. Acad. Sci. USA,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

A preferred example of algorithms that are suitable for determining percent sequence identity and sequence similarity are the BLAST and BLAST 2.0 algorithms, which are described in Altschul et al., *Nuc. Acids Res.,* 25:3389-3402 (1977) and Altschul et al., *J. Mol. Biol.,* 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/).

The BLAST algorithm also performs a statistical analysis of the similarity between two sequences (see, e.g., Karlin and Altschul, *Proc. Natl. Acad. Sci. USA,* 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, tRNA, viral RNA (vRNA), self-amplifying RNA, and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.,* 19:5081 (1991); Ohtsuka et al., *J. Biol. Chem.,* 260:2605-2608 (1985); Rossolini et al., *Mol. Cell. Probes,* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

As used herein, the term "LNP" refers to a lipid-nucleic acid particle or a nucleic acid-lipid particle (e.g., a stable nucleic acid-lipid particle). A LNP represents a particle made from lipids (e.g., a cationic lipid, a non-cationic lipid, and a conjugated lipid that prevents aggregation of the particle), and a nucleic acid, wherein the nucleic acid (e.g., siRNA, aiRNA, miRNA, ssDNA, dsDNA, ssRNA, short hairpin RNA (shRNA), dsRNA, mRNA, self-amplifying RNA, or a plasmid, including plasmids from which an interfering RNA or mRNA is transcribed) is encapsulated within the lipid. In one embodiment, the nucleic acid is at least 50% encapsulated in the lipid; in one embodiment, the nucleic acid is at least 75% encapsulated in the lipid; in one embodiment, the nucleic acid is at least 90% encapsulated in the lipid; and in one embodiment, the nucleic acid is completely encapsulated in the lipid. LNPs typically contain a cationic lipid, a non-cationic lipid, and a lipid conjugate (e.g., a PEG-lipid conjugate). LNP are extremely useful for systemic applications, as they can exhibit extended circulation lifetimes following intravenous (i.v.) injection, they can accumulate at distal sites (e.g., sites physically separated from the administration site), and they can mediate expression of the transfected gene or silencing of target gene expression at these distal sites.

The lipid particles of the invention (e.g., LNP) typically have a mean diameter of from about 40 nm to about 150 nm, from about 50 nm to about 150 nm, from about 60 nm to about 130 nm, from about 70 nm to about 110 nm, or from about 70 to about 90 nm, and are substantially non-toxic. In addition, nucleic acids, when present in the lipid particles of the invention, are resistant in aqueous solution to degradation with a nuclease. Nucleic acid-lipid particles and their method of preparation are disclosed in, e.g., U.S. Patent Publication Nos. 20040142025 and 20070042031, disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA or mRNA), with full encapsulation, partial encapsulation, or both. In a preferred embodiment, the nucleic acid is fully encapsulated in the lipid particle (e.g., to form an SPLP, pSPLP, LNP, or other nucleic acid-lipid particle).

The term "lipid conjugate" refers to a conjugated lipid that inhibits aggregation of lipid particles. Such lipid conjugates include, but are not limited to, polyamide oligomers (e.g., ATTA-lipid conjugates), PEG-lipid conjugates, such as PEG coupled to dialkyloxypropyls, PEG coupled to diacylglycerols, PEG coupled to cholesterol, PEG coupled to phosphatidylethanolamines, PEG conjugated to ceramides (see, e.g., U.S. Pat. No. 5,885,613, the disclosure of which is herein incorporated by reference in its entirety for all purposes), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In preferred embodiments, non-ester containing linker moieties are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to a compound of Formula (I) as described herein.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a lipid particle, such as a LNP, to fuse with the membranes of a cell.

The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as LNP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent or therapeutic agent, such as an interfering RNA or mRNA, within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent or therapeutic agent, such as an interfering RNA or mRNA, directly to a target site within an organism. For example, an agent can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, lung cancer, colon cancer, rectal cancer, anal cancer, bile duct cancer, small intestine cancer, stomach (gastric) cancer, esophageal cancer; gallbladder cancer, liver cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

The term "anionic precursor group" includes groups that are capable of forming an ion at physiological pH. For Example, the term includes the groups $—CO_2H$, $—O—P(═O)(OH)_2$, $—OS(═O)_2(OH)$, $—O—S(═O)(OH)$, and $—B(OH)_2$. In one embodiment, the anionic precursor is $—CO_2H$.

In a particular embodiment, PEG-C-DMA has the following structure:

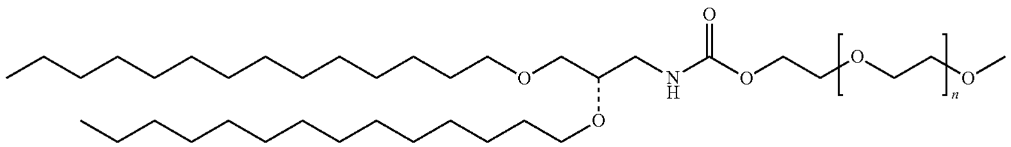

wherein n is selected so that the resulting polymer chain has a molecular weight of from about 1000 to about 3000. In another embodiment, n is selected so that the resulting polymer chain has a molecular weight of about 2000. PEG-C-DMA can be prepared as described by Heyes et al, Synthesis and Characterization of Novel Poly (Ethylene Glycol)-lipid Conjugates Suitable for use in Drug Delivery," *Journal of Controlled Release,* 2006, and in U.S. Pat. No. 8,936,942.

Description of the Embodiments

The present invention provides novel, serum-stable lipid particles comprising one or more active agents or therapeutic agents, methods of making the lipid particles, and methods of delivering and/or administering the lipid particles (e.g., for the treatment of a disease or disorder).

In one aspect, the present invention provides lipid particles comprising: (a) one or more active agents or therapeutic agents; (b) one or more cationic lipids comprising from about 30 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.1 mol % to about 10 mol % of the total lipid present in the particle.

In one aspect, the present invention provides lipid particles comprising: (a) one or more active agents or therapeutic agents; (b) one or more cationic lipids comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In certain embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In certain other embodiments, the lipid particles are substantially non-toxic to mammals such as humans.

In some embodiments, the active agent or therapeutic agent comprises a nucleic acid. In certain instances, the nucleic acid comprises an interfering RNA molecule such as, e.g., an siRNA, aiRNA, miRNA, or mixtures thereof. In certain other instances, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof. In certain instances, the nucleic acid comprises an mRNA molecule.

In other embodiments, the active agent or therapeutic agent comprises a peptide or polypeptide. In certain instances, the peptide or polypeptide comprises an antibody such as, e.g., a polyclonal antibody, a monoclonal antibody, an antibody fragment; a humanized antibody, a recombinant antibody, a recombinant human antibody, a Primatized™ antibody, or mixtures thereof. In certain other instances, the peptide or polypeptide comprises a cytokine, a growth factor, an apoptotic factor, a differentiation-inducing factor, a cell-surface receptor, a ligand, a hormone, a small molecule (e.g., small organic molecule or compound), or mixtures thereof.

In one embodiment, the active agent or therapeutic agent comprises an siRNA. In one embodiment, the siRNA molecule comprises a double-stranded region of about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). The siRNA molecules of the invention are capable of silencing the expression of a target sequence in vitro and/or in vivo.

In some embodiments, the siRNA molecule comprises at least one modified nucleotide. In certain preferred embodiments, the siRNA molecule comprises one, two, three, four, five, six, seven, eight, nine, ten, or more modified nucleotides in the double-stranded region. In certain instances, the siRNA comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region. In preferred embodiments, less than about 25% (e.g., less than about 25%, 20%, 15%, 10%, or 5%) or from about 1% to about 25% (e.g., from about 1%-25%, 5%-25%, 10%-25%, 15%-25%, 20%-25%, or 10%-20%) of the nucleotides in the double-stranded region comprise modified nucleotides.

In other embodiments, the siRNA molecule comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain instances, the siRNA does not comprise 2'OMe-cytosine nucleotides. In other embodiments, the siRNA comprises a hairpin loop structure.

The siRNA may comprise modified nucleotides in one strand (e.g., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some preferred embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the LNP delivery system disclosed herein).

In certain embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 80%, 85%, 90%, 95%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. Preferably, the siRNA has 3' overhangs of two nucleotides on each side of the double-stranded region. In certain instances, the 3' overhang on the antisense strand has complementarity to the target sequence and the 3' overhang on the sense strand has complementarity to a complementary strand of the target sequence. Alternatively, the 3' overhangs do not have complementarity to the target sequence or the complementary strand thereof. In some embodiments, the 3' overhangs comprise one, two, three, four, or more nucleotides such as 2'-deoxy (2'H) nucleotides. In certain preferred embodiments, the 3' overhangs comprise deoxythymidine (dT) and/or uridine nucleotides. In other embodiments, one or more of the nucleotides in the 3' overhangs on one or both sides of the double-stranded region comprise modified nucleotides. Non-limiting examples of modified nucleotides are described above and include 2'OMe nucleotides, 2'-deoxy-2'F nucleotides, 2'-deoxy nucleotides, 2'-O-2-MOE nucleotides, LNA nucleotides, and mixtures thereof. In preferred embodiments, one, two, three, four, or more nucleotides in the 3' overhangs present on the sense and/or antisense strand of the siRNA comprise 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof.

The siRNA may comprise at least one or a cocktail (e.g., at least two, three, four, five, six, seven, eight, nine, ten, or more) of unmodified and/or modified siRNA sequences that silence target gene expression. The cocktail of siRNA may comprise sequences which are directed to the same region or domain (e.g., a "hot spot") and/or to different regions or domains of one or more target genes. In certain instances, one or more (e.g., at least two, three, four, five, six, seven, eight, nine, ten, or more) modified siRNA that silence target gene expression are present in a cocktail. In certain other instances, one or more (e.g., at least two, three, four, five, six, seven, eight, nine, ten, or more) unmodified siRNA sequences that silence target gene expression are present in a cocktail.

In some embodiments, the antisense strand of the siRNA molecule comprises or consists of a sequence that is at least about 80%, 85%, 90%, 95%, 96%, 97%, 98%, or 99% complementary to the target sequence or a portion thereof. In other embodiments, the antisense strand of the siRNA molecule comprises or consists of a sequence that is 100% complementary to the target sequence or a portion thereof. In further embodiments, the antisense strand of the siRNA molecule comprises or consists of a sequence that specifically hybridizes to the target sequence or a portion thereof.

In further embodiments, the sense strand of the siRNA molecule comprises or consists of a sequence that is at least about 80%, 85%, 90%, 95%, 96%, 97%, 98%, or 99% identical to the target sequence or a portion thereof. In additional embodiments, the sense strand of the siRNA molecule comprises or consists of a sequence that is 100% identical to the target sequence or a portion thereof.

In the lipid nanoparticles of the invention, the cationic lipid can be selected from the compounds of Formula (I) as described herein.

In some embodiments, the cationic lipid may comprise from about 30 mol % to about 90 mol %, from about 30 mol % to about 85 mol %, from about 30 mol % to about 80 mol %, from about 30 mol % to about 75 mol %, from about 30 mol % to about 70 mol %, from about 30 mol % to about 65 mol %, or from about 30 mol % to about 60 mol % of the total lipid present in the particle.

In some embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

In other embodiments, the cationic lipid may comprise from about 55 mol % to about 90 mol %, from about 55 mol % to about 85 mol %, from about 55 mol % to about 80 mol %, from about 55 mol % to about 75 mol %, from about 55 mol % to about 70 mol %, or from about 55 mol % to about 65 mol % of the total lipid present in the particle.

In yet other embodiments, the cationic lipid may comprise from about 60 mol % to about 90 mol %, from about 60 mol % to about 85 mol %, from about 60 mol % to about 80 mol %, from about 60 mol % to about 75 mol %, or from about 60 mol % to about 70 mol % of the total lipid present in the particle.

In still yet other embodiments, the cationic lipid may comprise from about 65 mol % to about 90 mol %, from about 65 mol % to about 85 mol %, from about 65 mol % to about 80 mol %, or from about 65 mol % to about 75 mol % of the total lipid present in the particle.

In further embodiments, the cationic lipid may comprise from about 70 mol % to about 90 mol %, from about 70 mol % to about 85 mol %, from about 70 mol % to about 80 mol %, from about 75 mol % to about 90 mol %, from about 75 mol % to about 85 mol %, or from about 80 mol % to about 90 mol % of the total lipid present in the particle.

In additional embodiments, the cationic lipid may comprise (at least) about 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In the lipid particles of the invention, the non-cationic lipid may comprise, e.g., one or more anionic lipids and/or neutral lipids. In preferred embodiments, the non-cationic lipid comprises one of the following neutral lipid components: (1) cholesterol or a derivative thereof (2) a phospholipid; or (3) a mixture of a phospholipid and cholesterol or a derivative thereof.

Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The synthesis of cholesteryl-2'-hydroxyethyl ether is described herein.

The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain preferred embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

In other embodiments, the non-cationic lipid (e.g., one or more phospholipids and/or cholesterol) may comprise from about 10 mol % to about 49.5 mol %, from about 13 mol % to about 49.5 mol %, from about 15 mol % to about 49.5 mol %, from about 20 mol % to about 49.5 mol %, from about 25 mol % to about 49.5 mol %, from about 30 mol % to about 49.5 mol %, from about 35 mol % to about 49.5 mol %, or from about 40 mol % to about 49.5 mol % of the total lipid present in the particle.

In yet other embodiments, the non-cationic lipid (e.g., one or more phospholipids and/or cholesterol) may comprise from about 10 mol % to about 45 mol %, from about 13 mol % to about 45 mol %, from about 15 mol % to about 45 mol %, from about 20 mol % to about 45 mol %, from about 25 mol % to about 45 mol %, from about 30 mol % to about 45 mol %, or from about 35 mol % to about 45 mol % of the total lipid present in the particle.

In still yet other embodiments, the non-cationic lipid (e.g., one or more phospholipids and/or cholesterol) may comprise from about 10 mol % to about 40 mol %, from about 13 mol % to about 40 mol %, from about 15 mol % to about 40 mol %, from about 20 mol % to about 40 mol %, from about 25 mol % to about 40 mol %, or from about 30 mol % to about 40 mol % of the total lipid present in the particle.

In further embodiments, the non-cationic lipid (e.g., one or more phospholipids and/or cholesterol) may comprise from about 10 mol % to about 35 mol %, from about 13 mol % to about 35 mol %, from about 15 mol % to about 35 mol %, from about 20 mol % to about 35 mol or from about 25 mol % to about 35 mol % of the total lipid present in the particle.

In yet further embodiments, the non-cationic lipid (e.g., one or more phospholipids and/or cholesterol) may comprise from about 10 mol % to about 30 mol %, from about 13 mol % to about 30 mol %, from about 15 mol % to about 30 mol %, from about 20 mol % to about 30 mol %, from about 10 mol % to about 25 mol %, from about 13 mol % to about 25 mol %, or from about 15 mol % to about 25 mol % of the total lipid present in the particle.

In additional embodiments, the non-cationic lipid (e.g., one or more phospholipids and/or cholesterol) may comprise (at least) about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol % (or any fraction thereof or range therein) of the total lipid present in the particle.

In certain preferred embodiments, the non-cationic lipid comprises cholesterol or a derivative thereof of from about 31.5 mol % to about 42.5 mol % of the total lipid present in the particle. As a non-limiting example, a phospholipid-free lipid particle of the invention may comprise cholesterol or a derivative thereof at about 37 mol % of the total lipid present in the particle. In other preferred embodiments, a phospholipid-free lipid particle of the invention may comprise cholesterol or a derivative thereof of from about 30 mol % to about 45 mol %, from about 30 mol % to about 40 mol %, from about 30 mol % to about 35 mol %, from about 35 mol % to about 45 mol %, from about 40 mol % to about 45 mol %, from about 32 mol % to about 45 mol %, from about 32 mol % to about 42 mol %, from about 32 mol % to about 40 mol %, from about 34 mol % to about 45 mol %, from about 34 mol % to about 42 mol %, from about 34 mol % to about 40 mol %, or about 30, 31, 32, 33, 34, 35, 36, 37, 38, 39, 40, 41, 42, 43, 44, or 45 mol % (or any fraction thereof or range therein) of the total lipid present in the particle.

In certain other preferred embodiments, the non-cationic lipid comprises a mixture of: (i) a phospholipid of from about 4 mol % to about 10 mol % of the total lipid present in the particle; and (ii) cholesterol or a derivative thereof of from about 30 mol % to about 40 mol % of the total lipid present in the particle. As a non-limiting example, a lipid particle comprising a mixture of a phospholipid and cholesterol may comprise DPPC at about 7 mol % and cholesterol at about 34 mol % of the total lipid present in the particle. In other embodiments, the non-cationic lipid comprises a mixture of: (i) a phospholipid of from about 3 mol % to about 15 mol %, from about 4 mol % to about 15 mol %, from about 4 mol % to about 12 mol %, from about 4 mol % to about 10 mol %, from about 4 mol % to about 8 mol %, from about 5 mol % to about 12 mol %, from about 5 mol % to about 9 mol %, from about 6 mol % to about 12 mol %, from about 6 mol % to about 10 mol %, or about 3, 4, 5, 6, 7, 8, 9, 10, 11, 12, 13, 14, or 15 mol % (or any fraction thereof or range therein) of the total lipid present in the particle; and (ii) cholesterol or a derivative thereof of from about 25 mol % to about 45 mol %, from about 30 mol % to about 45 mol %, from about 25 mol % to about 40 mol %, from about 30 mol % to about 40 mol %, from about 25 mol % to about 35 mol %, from about 30 mol % to about 35 mol %, from about 35 mol % to about 45 mol %, from about 40 mol % to about 45 mol %, from about 28 mol % to about 40 mol %, from about 28 mol % to about 38 mol %, from about 30 mol % to about 38 mol %, from about 32 mol % to about 36 mol %, or about 25, 26, 27, 28, 29, 30, 31, 32, 33, 34, 35, 36, 37, 38, 39, 40, 41, 42, 43, 44, or 45 mol % (or any fraction thereof or range therein) of the total lipid present in the particle.

In further preferred embodiments, the non-cationic lipid comprises a mixture of: (i) a phospholipid of from about 10 mol % to about 30 mol % of the total lipid present in the particle; and (ii) cholesterol or a derivative thereof of from about 10 mol % to about 30 mol % of the total lipid present in the particle. As a non-limiting example, a lipid particle comprising a mixture of a phospholipid and cholesterol may comprise DPPC at about 20 mol % and cholesterol at about 20 mol % of the total lipid present in the particle. In other embodiments, the non-cationic lipid comprises a mixture of: (i) a phospholipid of from about 10 mol % to about 30 mol %, from about 10 mol % to about 25 mol %, from about 10 mol % to about 20 mol %, from about 15 mol % to about 30 mol %, from about 20 mol % to about 30 mol %, from about 15 mol % to about 25 mol %, from about 12 mol % to about 28 mol %, from about 14 mol % to about 26 mol %, or about 10, 11, 12, 13, 14, 15, 16, 17, 18, 19, 20, 21, 22, 23, 24, 25, 26, 27, 28, 29, or 30 mol % (or any fraction thereof or range therein) of the total lipid present in the particle; and (ii) cholesterol or a derivative thereof of from about 10 mol % to about 30 mol %, from about 10 mol % to about 25 mol %, from about 10 mol % to about 20 mol %, from about 15 mol % to about 30 mol %, from about 20 mol % to about 30 mol %, from about 15 mol % to about 25 mol %, from about 12 mol % to about 28 mol %, from about 14 mol % to about 26 mol %, or about 10, 11, 12, 13, 14, 15, 16, 17, 18, 19, 20, 21, 22, 23, 24, 25, 26, 27, 28, 29, or 30 mol % (or any fraction thereof or range therein) of the total lipid present in the particle.

Conjugated Lipid

In the lipid particles of the invention (e.g., LNP comprising, e.g., an interfering RNA such as siRNA, or mRNA), the conjugated lipid may comprise, e.g., one or more of the following: a polyethyleneglycol (PEG)-lipid conjugate, a polyamide (ATTA)-lipid conjugate, or mixtures thereof. In one preferred embodiment, the nucleic acid-lipid particles comprise either a PEG-lipid conjugate or an ATTA-lipid conjugate. The conjugated lipid s may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676, filed Dec. 31, 2008, the disclosure of which is herein incorporated by reference in its entirety for all purposes. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-w-methyl-poly(ethylene glycol) (2 KPEG-DMG). The synthesis of 2 KPEG-DMG is described in U.S. Pat. No. 7,404,969, the disclosure of which is herein incorporated by reference in its entirety for all purposes.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the conjugated lipid (e.g., PEG-lipid conjugate) may comprise from about 0.1 to about 10% (or any fraction thereof or range therein) of the total lipid present in the particle. In certain instances, the conjugated lipid (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle.

In the lipid particles of the invention, the active agent or therapeutic agent may be fully encapsulated within the lipid portion of the particle, thereby protecting the active agent or therapeutic agent from enzymatic degradation. In preferred embodiments, a LNP comprising a nucleic acid, such as an interfering RNA (e.g., siRNA) or mRNA, is fully encapsulated within the lipid portion of the particle, thereby protecting the nucleic acid from nuclease degradation. In certain instances, the nucleic acid in the LNP is not substantially degraded after exposure of the particle to a nuclease at 37° C. for at least about 20, 30, 45, or 60 minutes. In certain other instances, the nucleic acid in the LNP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the active agent or therapeutic agent (e.g., nucleic acid such as siRNA) is complexed with the lipid portion of the particle. One of the benefits of the formulations of the present invention is that the lipid particle compositions are substantially non-toxic to mammals such as humans.

The term "fully encapsulated" indicates that the active agent or therapeutic agent in the lipid particle is not significantly degraded after exposure to serum or a nuclease or protease assay that would significantly degrade free DNA, RNA, or protein. In a fully encapsulated system, preferably less than about 25% of the active agent or therapeutic agent in the particle is degraded in a treatment that would normally degrade 100% of free active agent or therapeutic agent, more preferably less than about 10%, and most preferably less than about 5% of the active agent or therapeutic agent in the particle is degraded. In the context of nucleic acid therapeutic agents, full encapsulation may be determined by an Oligreen® assay. Oligreen® is an ultra-sensitive fluorescent nucleic acid stain for quantitating oligonucleotides and single-stranded DNA or RNA in solution (available from Invitrogen Corporation; Carlsbad, Calif.). "Fully encapsulated" also indicates that the lipid particles are serum-stable, that is, that they do not rapidly decompose into their component parts upon in vivo administration.

In another aspect, the present invention provides a lipid particle (e.g., LNP) composition comprising a plurality of lipid particles. In preferred embodiments, the active agent or therapeutic agent (e.g., nucleic acid) is fully encapsulated within the lipid portion of the lipid particles (e.g., LNP), such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, %, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the lipid particles (e.g., LNP) have the active agent or therapeutic agent encapsulated therein.

Typically, the lipid particles (e.g., LNP) of the invention have a lipid:active agent (e.g., lipid:nucleic acid) ratio (mass/mass ratio) of from about 1 to about 100. In some instances, the lipid:active agent (e.g., lipid:nucleic acid) ratio (mass/mass ratio) ranges from about 1 to about 50, from about 2 to about 25, from about 3 to about 20, from about 4 to about 15, or from about 5 to about 10. In preferred embodiments, the lipid particles of the invention have a lipid:active agent (e.g., lipid:nucleic acid) ratio (mass/mass ratio) of from about 5 to about 15, e.g., about 5, 6, 7, 8, 9, 10, 11, 12, 13, 14, or 15 (or any fraction thereof or range therein).

Typically, the lipid particles (e.g., LNP) of the invention have a mean diameter of from about 40 nm to about 150 nm. In preferred embodiments, the lipid particles (e.g., LNP) of the invention have a mean diameter of from about 40 nm to about 130 nm, from about 40 nm to about 120 nm, from about 40 nm to about 100 nm, from about 50 nm to about 120 nm, from about 50 nm to about 100 nm, from about 60 nm to about 120 nm, from about 60 nm to about 110 nm, from about 60 nm to about 100 nm, from about 60 nm to about 90 nm, from about 60 nm to about 80 nm, from about 70 nm to about 120 nm, from about 70 nm to about 110 nm, from about 70 nm to about 100 nm, from about 70 nm to about 90 nm, from about 70 nm to about 80 nm, or less than about 120 nm, 110 nm, 100 nm, 90 nm, or 80 nm (or any fraction thereof or range therein).

In one specific embodiment of the invention, the LNP comprises: (a) one or more unmodified and/or modified nucleic acid molecules (e.g., interfering RNA that silence target gene expression, such as siRNA, aiRNA, miRNA; or mRNA that result in target protein expression); (b) a cationic lipid comprising from about 56.5 mol % to about 66.5 mol % of the total lipid present in the particle; (c) a non-cationic lipid comprising from about 31.5 mol % to about 42.5 mol % of the total lipid present in the particle; and (d) a conjugated lipid that inhibits aggregation of particles comprising from about 1 mol % to about 2 mol % of the total lipid present in the particle. This specific embodiment of LNP is generally referred to herein as the "1:62" formulation. In a preferred embodiment, the cationic lipid is DLinDMA or DLin-K-C2-DMA ("XTC2"), the non-cationic lipid is cholesterol, and the conjugated lipid is a PEG-DAA conjugate. Although these are preferred embodiments of the 1:62 formulation, those of skill in the art will appreciate that other cationic lipids, non-cationic lipids (including other cholesterol derivatives), and conjugated lipids can be used in the 1:62 formulation as described herein.

In another specific embodiment of the invention, the LNP comprises: (a) one or more unmodified and/or modified nucleic acid molecules (e.g., interfering RNA that silence target gene expression, such as siRNA, aiRNA, miRNA; or mRNA that result in target protein expression); (b) a cationic lipid comprising from about 52 mol % to about 62 mol % of the total lipid present in the particle; (c) a non-cationic lipid comprising from about 36 mol % to about 47 mol % of the total lipid present in the particle; and (d) a conjugated lipid that inhibits aggregation of particles comprising from about 1 mol % to about 2 mol % of the total lipid present in the particle. This specific embodiment of LNP is generally referred to herein as the "1:57" formulation. In one preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 5 mol % to about 9 mol % of the total lipid present in the particle (e.g., about 7.1 mol %) and the cholesterol (or cholesterol derivative) comprises from about 32 mol % to about 37 mol % of the total lipid present in the particle (e.g., about 34.3 mol %), and the PEG-lipid is a PEG-DAA (e.g., PEG-cDMA). In another preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 15 mol % to about 25 mol % of the total lipid present in the particle (e.g., about 20 mol %) and the cholesterol (or cholesterol derivative) comprises from about 15 mol % to about 25 mol % of the total lipid present in the particle (e.g., about 20 mol %), and the PEG-lipid is a PEG-DAA (e.g., PEG-cDMA). Although these are preferred embodiments of the 1:57 formulation, those of skill in the art will appreciate that other cationic lipids, non-cationic lipids (including other phospholipids and other cholesterol derivatives), and conjugated lipids can be used in the 1:57 formulation as described herein.

In preferred embodiments, the 1:62 LNP formulation is a three-component system which is phospholipid-free and comprises about 1.5 mol % PEG-cDMA (or PEG-IDSA), about 61.5 mol % DLinDMA (or XTC2), and about 36.9 mol % cholesterol (or derivative thereof). In other preferred embodiments, the 1:57 LNP formulation is a four-component system which comprises about 1.4 mol % PEG-cDMA (or PEG-cDSA), about 57.1 mol % DLinDMA (or XTC2), about 7.1 mol % DPPC, and about 34.3 mol % cholesterol (or derivative thereof). In yet other preferred embodiments, the 1:57 LNP formulation is a four-component system which comprises about 1.4 mol % PEG-cDMA (or PEG-cDSA), about 57.1 mol % DLinDMA (or XTC2), about 20 mol % DPPC, and about 20 mol % cholesterol (or derivative thereof). It should be understood that these LNP formulations are target formulations, and that the amount of lipid (both cationic and non-cationic) present and the amount of lipid conjugate present in the LNP formulations may vary.

The present invention also provides a pharmaceutical composition comprising a lipid particle (e.g., LNP) described herein and a pharmaceutically acceptable carrier.

In a further aspect, the present invention provides a method for introducing one or more active agents or therapeutic agents (e.g., nucleic acid) into a cell, comprising contacting the cell with a lipid particle (e.g., LNP) described herein. In one embodiment, the cell is in a mammal and the mammal is a human. In another embodiment, the present invention provides a method for the in vivo delivery of one or more active agents or therapeutic agents (e.g., nucleic acid), comprising administering to a mammalian subject a lipid particle (e.g., LNP) described herein. In a preferred embodiment, the mode of administration includes, but is not limited to, oral, intranasal, intravenous, intraperitoneal, intramuscular, intra-articular, intralesional, intratracheal, subcutaneous, and intradermal. Preferably, the mammalian subject is a human.

In one embodiment, at least about 5%, 10%, 15%, 20%, or 25% of the total injected dose of the lipid particles (e.g., LNP) is present in plasma about 8, 12, 24, 36, or 48 hours after injection. In other embodiments, more than about 20%, 30%, 40% and as much as about 60%, 70% or 80% of the total injected dose of the lipid particles (e.g., LNP) is present in plasma about 8, 12, 24, 36, or 48 hours after injection. In certain instances, more than about 10% of a plurality of the particles is present in the plasma of a mammal about 1 hour after administration. In certain other instances, the presence of the lipid particles (e.g., LNP) is detectable at least about 1 hour after administration of the particle. In certain embodiments, the presence of an active agent or therapeutic agent, such as an interfering RNA (e.g., siRNA) or mRNA is detectable in cells of the at about 8, 12, 24, 36, 48, 60, 72 or 96 hours after administration (e.g., lung, liver, tumor, or at a site of inflammation). In other embodiments, downregulation of expression of a target sequence by an active agent or therapeutic agent, such as an interfering RNA (e.g., siRNA) is detectable at about 8, 12, 24, 36, 48, 60, 72 or 96 hours after administration. In yet other embodiments, downregulation of expression of a target sequence by an active agent or therapeutic agent such as an interfering RNA (e.g., siRNA) occurs preferentially in tumor cells or in cells at a site of inflammation. In further embodiments, the presence or effect of an active agent or therapeutic agent such as an interfering RNA (e.g., siRNA) in cells at a site proximal or distal to the site of administration or in cells of the lung, liver, or a tumor is detectable at about 12, 24, 48, 72, or 96 hours, or at about 6, 8, 10, 12, 14, 16, 18, 19, 20, 22, 24, 26, or 28 days after administration. In other embodiments, upregulation of expression of a target sequence by an active agent or therapeutic agent, such as an mRNA or self-amplifying RNA is detectable at about 8, 12, 24, 36, 48, 60, 72 or 96 hours after administration. In yet other embodiments, upregulation of expression of a target sequence by an active agent or therapeutic agent such as an mRNA or self-amplifying RNA occurs preferentially in tumor cells or in cells at a site of inflammation. In further embodiments, the presence or effect of an active agent or therapeutic agent such as an mRNA or self-replicating RNA in cells at a site proximal or distal to the site of administration or in cells of the lung, liver, or a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., LNP) of the invention are administered parenterally or intraperitoneally.

In some embodiments, the lipid particles (e.g., LNP) of the invention are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest. As a non-limiting example, the methods of the invention are useful for in vivo delivery of interfering RNA (e.g., siRNA) to the liver and/or tumor of a mammalian subject. In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle (e.g., LNP) may be administered to the mammal. In some instances, an interfering RNA (e.g., siRNA) is formulated into a LNP, and the particles are administered to patients requiring such treatment. In other instances, cells are removed from a patient, the interfering RNA (e.g., siRNA) is delivered in vitro (e.g., using a LNP described herein), and the cells are reinjected into the patient.

In an additional aspect, the present invention provides lipid particles (e.g., LNP) comprising asymmetrical interfering RNA (aiRNA) molecules that silence the expression of a target gene and methods of using such particles to silence target gene expression.

In one embodiment, the aiRNA molecule comprises a double-stranded (duplex) region of about 10 to about 25 (base paired) nucleotides in length, wherein the aiRNA molecule comprises an antisense strand comprising 5' and 3' overhangs, and wherein the aiRNA molecule is capable of silencing target gene expression.

In certain instances, the aiRNA molecule comprises a double-stranded (duplex) region of about 12-20, 12-19, 12-18, 13-17, or 14-17 (base paired) nucleotides in length, more typically 12, 13, 14, 15, 16, 17, 18, 19, or 20 (base paired) nucleotides in length. In certain other instances, the 5' and 3' overhangs on the antisense strand comprise sequences that are complementary to the target RNA sequence, and may optionally further comprise nontargeting sequences. In some embodiments, each of the 5' and 3' overhangs on the antisense strand comprises or consists of one, two, three, four, five, six, seven, or more nucleotides.

In other embodiments, the aiRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the aiRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

In a related aspect, the present invention provides lipid particles (e.g., LNP) comprising microRNA (miRNA) molecules that silence the expression of a target gene and methods of using such compositions to silence target gene expression.

In one embodiment, the miRNA molecule comprises about 15 to about 60 nucleotides in length, wherein the miRNA molecule is capable of silencing target gene expression.

In certain instances, the miRNA molecule comprises about 15-50, 15-40, or 15-30 nucleotides in length, more typically about 15-25 or 19-25 nucleotides in length, and are preferably about 20-24, 21-22, or 21-23 nucleotides in length. In a preferred embodiment, the miRNA molecule is a mature miRNA molecule targeting an RNA sequence of interest.

In some embodiments, the miRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the miRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

In some embodiments, the lipid particles (e.g., LNP) of the invention are useful in methods for the therapeutic delivery of one or more mRNA molecules. In particular, it is one object of this invention to provide in vitro and in vivo methods for treatment of a disease or disorder in a mammal (e.g., a rodent such as a mouse or a primate such as a human, chimpanzee, or monkey) through the expression of one or more target proteins. As a non-limiting example, the methods of the invention are useful for in vivo delivery of one or more mRNA molecules to a mammalian subject. In certain other embodiments, a therapeutically effective amount of the lipid particle (e.g., LNP) may be administered to the mammal. In some instances, one or more mRNA molecules are formulated into a LNP, and the particles are administered to patients requiring such treatment. In other instances, cells are removed from a patient, one or more mRNA molecules are delivered in vitro (e.g., using a LNP described herein), and the cells are reinjected into the patient.

In other embodiments, the mRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a related aspect, the present invention provides lipid particles (e.g., LNP) comprising microRNA (miRNA) molecules that silence the expression of a target gene and methods of using such compositions to silence target gene expression.

As such, the lipid particles of the invention (e.g., LNP) are advantageous and suitable for use in the administration of active agents or therapeutic agents, such as nucleic acid (e.g., interfering RNA such as siRNA, aiRNA, and/or miRNA; or mRNA) to a subject (e.g., a mammal such as a human) because they are stable in circulation, of a size required for pharmacodynamic behavior resulting in access to extravascular sites, and are capable of reaching target cell populations.

Active Agents

Active agents (e.g., therapeutic agents) include any molecule or compound capable of exerting a desired effect on a cell, tissue, organ, or subject. Such effects may be, e.g., biological, physiological, and/or cosmetic. Active agents may be any type of molecule or compound including, but not limited to, nucleic acids, peptides, polypeptides, small molecules, and mixtures thereof. Non-limiting examples of nucleic acids include interfering RNA molecules (e.g., siRNA, aiRNA, miRNA), antisense oligonucleotides, mRNA, self-amplifying RNA, plasmids, ribozymes, immunostimulatory oligonucleotides, and mixtures thereof. Examples of peptides or polypeptides include, without limitation, antibodies (e.g., polyclonal antibodies, monoclonal antibodies, antibody fragments; humanized antibodies, recombinant antibodies, recombinant human antibodies, Primatized™ antibodies), cytokines, growth factors, apoptotic factors, differentiation-inducing factors, cell-surface receptors and their ligands, hormones, and mixtures thereof. Examples of small molecules include, but are not limited to, small organic molecules or compounds such as any conventional agent or drug known to those of skill in the art.

In some embodiments, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative is a prodrug that lacks therapeutic activity, but becomes active upon further modification.

Nucleic Acids

In certain embodiments, lipid particles of the present invention are associated with a nucleic acid, resulting in a nucleic acid-lipid particle (e.g., LNP). In some embodiments, the nucleic acid is fully encapsulated in the lipid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. Nucleic acid may be administered alone in the lipid particles of the invention, or in combination (e.g., co-administered) with lipid particles of the invention comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids. Examples of double-stranded DNA are described herein and include, e.g., structural genes, genes including control and termination regions, and self-replicating systems such as viral or plasmid DNA. Examples of double-stranded RNA are described herein and include, e.g., siRNA and other RNAi agents such as aiRNA and pre-miRNA. Single-stranded nucleic acids include, e.g., antisense oligonucleotides, ribozymes, mature miRNA, and triplex-forming oligonucleotides.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, e.g., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

siRNA

The siRNA component of the nucleic acid-lipid particles of the present invention is capable of silencing the expression of a target gene of interest. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. In preferred embodiments, one or more of the uridine and/or guanosine nucleotides are modified. The modified nucleotides can be present in one strand (e.g., sense or antisense) or both strands of the siRNA. The siRNA sequences may have overhangs (e.g., 3' or 5' overhangs as described in Elbashir et al., *Genes Dev.,* 15:188 (2001) or Nykänen et al., *Cell,* 107:309 (2001)), or may lack overhangs (i.e., have blunt ends).

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

In some embodiments, less than about 25% (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%) of the nucleotides in the double-stranded region of the siRNA comprise modified nucleotides.

In other embodiments, from about 1% to about 25% (e.g., from about 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, etc.) or from about 1% to about 20% (e.g., from about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, etc.) of the nucleotides in the double-stranded region of the siRNA comprise modified nucleotides.

In further embodiments, e.g., when one or both strands of the siRNA are selectively modified at uridine and/or guanosine nucleotides, the resulting modified siRNA can comprise less than about 30% modified nucleotides (e.g., less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or from about 1% to about 30% modified nucleotides (e.g., from about 1%-30%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, or 29%-30% modified nucleotides).

Selection of siRNA Sequences

Suitable siRNA sequences can be identified using any means known in the art. Typically, the methods described in Elbashir et al., *Nature,* 411:494-498 (2001) and Elbashir et al., *EMBO J.,* 20:6877-6888 (2001) are combined with rational design rules set forth in Reynolds et al., *Nature Biotech.,* 22(3):326-330 (2004).

Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., *EMBO J.,* 20:6877-6888 (2001)). The nucleotides immediately 3' to the dinucleotide sequences are identified as potential siRNA sequences (e.g., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (e.g., an antisense strand sequence) can be designed. A potential siRNA sequence can also be analyzed using a variety of criteria known in the art.

For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://boz094.ust.hk/RNAi/siRNA. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (e.g., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell,* 115:209-216 (2003); and Schwarz et al., *Cell,* 115:199-208 (2003). In other embodiments, potential siRNA sequences may be further analyzed based on secondary structure at the target site as described in, e.g., Luo et al., *Biophys. Res. Commun.,* 318:303-310 (2004). For example, secondary structure at the target site can be modeled using the Mfold algorithm (available at http://www.bioinfo.rpi.edu/applications/mfold/ma/form1.cgi) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.,* 255:4980-4983 (1980)); enzyme-linked immunosorbent assays (ELISA) as described, for example, by Raines et al., *J. Biol. Chem.,* 257:5154-5160 (1982); immunocytochemical techniques, including the use of fluorochromes (Brooks et al., *Clin. Exp. Immunol.,* 39:477 (1980)); and neutralization of activity (Bowen-Pope et al., *Proc. Natl. Acad. Sci. USA,* 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.,* 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature,* 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al.,

*Genes Dev.,* 15:188 (2001) or Nykänen et al., *Cell,* 107:309 (2001), or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202*; PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-0, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.,* 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.,* 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (e.g., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties, in Modern Synthetic Methods*, VCH, 331-417 (1995); Mesmaeker et al., *Novel Backbone Replacements for Oligonucleotides, in Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-β-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

Target Genes

In certain embodiments, the nucleic acid component (e.g., siRNA) of the nucleic acid-lipid particles described herein can be used to downregulate or silence the translation (i.e., expression) of a gene of interest. Genes of interest include, but are not limited to, genes associated with viral infection and survival, genes associated with metabolic diseases and disorders (e.g., liver diseases and disorders), genes associated with tumorigenesis and cell transformation (e.g., cancer), angiogenic genes, immunomodulator genes such as those associated with inflammatory and autoimmune responses, ligand receptor genes, and genes associated with neurodegenerative disorders. In certain embodiments, the gene of interest is expressed in hepatocytes.

Genes associated with viral infection and survival include those expressed by a virus in order to bind, enter, and replicate in a cell. Of particular interest are viral sequences associated with chronic viral diseases. Viral sequences of particular interest include sequences of Filoviruses such as Ebola virus and Marburg virus (see, e.g., Geisbert et al., *J. Infect. Dis.,* 193:1650-1657 (2006)); Arenaviruses such as Lassa virus, Junin virus, Machupo virus, Guanarito virus, and Sabia virus (Buchmeier et al., Arenaviridae: the viruses and their replication, In: FIELDS VIROLOGY, Knipe et al. (eds.), 4th ed., Lippincott-Raven, Philadelphia, (2001)); Influenza viruses such as Influenza A, B, and C viruses, (see, e.g., Steinhauer et al., *Annu Rev Genet.,* 36:305-332 (2002); and Neumann et al., *J Gen Virol.,* 83:2635-2662 (2002)); Hepatitis viruses (see, e.g., Hamasaki et al., *FEBS Lett.,* 543:51 (2003); Yokota et al., *EMBO Rep.,* 4:602 (2003); Schlomai et al., *Hepatology,* 37:764 (2003); Wilson et al.,

*Proc. Natl. Acad. Sci. USA,* 100:2783 (2003); Kapadia et al., *Proc. Natl. Acad. Sci. USA,* 100:2014 (2003); and FIELDS VIROLOGY, Knipe et al. (eds.), 4th ed., Lippincott-Raven, Philadelphia (2001)); Human Immunodeficiency Virus (HIV) (Banerjea et al., *Mol. Ther.,* 8:62 (2003); Song et al., *J. Virol.,* 77:7174 (2003); Stephenson, *JAMA,* 289:1494 (2003); Qin et al., *Proc. Natl. Acad. Sci. USA,* 100:183 (2003)); Herpes viruses (Jia et al., *J. Virol.,* 77:3301 (2003)); and Human Papilloma Viruses (HPV) (Hall et al., *J. Virol.,* 77:6066 (2003); Jiang et al., *Oncogene,* 21:6041 (2002)).

Exemplary Filovirus nucleic acid sequences that can be silenced include, but are not limited to, nucleic acid sequences encoding structural proteins (e.g., VP30, VP35, nucleoprotein (NP), polymerase protein (L-pol)) and membrane-associated proteins (e.g., VP40, glycoprotein (GP), VP24). Complete genome sequences for Ebola virus are set forth in, e.g., Genbank Accession Nos. NC-002549; AY769362; NC-006432; NC-004161; AY729654; AY354458; AY142960; AB050936; AF522874; AF499101; AF272001; and AF086833. Ebola virus VP24 sequences are set forth in, e.g., Genbank Accession Nos. U77385 and AY058897. Ebola virus L-pol sequences are set forth in, e.g., Genbank Accession No. X67110. Ebola virus VP40 sequences are set forth in, e.g., Genbank Accession No. AY058896. Ebola virus NP sequences are set forth in, e.g., Genbank Accession No. AY058895. Ebola virus GP sequences are set forth in, e.g., Genbank Accession No. AY058898; Sanchez et al., Virus Res., 29:215-240 (1993); Will et al., *J. Virol.,* 67:1203-1210 (1993); Volchkov et al., *FEBS Lett.,* 305:181-184 (1992); and U.S. Pat. No. 6,713, 069. Additional Ebola virus sequences are set forth in, e.g., Genbank Accession Nos. L11365 and X61274. Complete genome sequences for Marburg virus are set forth in, e.g., Genbank Accession Nos. NC-001608; AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132. Non-limiting examples of siRNA molecules targeting Ebola virus and Marburg virus nucleic acid sequences include those described in U.S. Patent Publication No. 20070135370, the disclosure of which is herein incorporated by reference in its entirety for all purposes.

Exemplary Influenza virus nucleic acid sequences that can be silenced include, but are not limited to, nucleic acid sequences encoding nucleoprotein (NP), matrix proteins (M1 and M2), nonstructural proteins (NS1 and NS2), RNA polymerase (PA, PB1, PB2), neuraminidase (NA), and haemagglutinin (HA). Influenza A NP sequences are set forth in, e.g., Genbank Accession Nos. NC-004522; AY818138; AB166863; AB188817; AB189046; AB189054; AB189062; AY646169; AY646177; AY651486; AY651493; AY651494; AY651495; AY651496; AY651497; AY651498; AY651499; AY651500; AY651501; AY651502; AY651503; AY651504; AY651505; AY651506; AY651507; AY651509; AY651528; AY770996; AY790308; AY818138; and AY818140. Influenza A PA sequences are set forth in, e.g., Genbank Accession Nos. AY818132; AY790280; AY646171; AY818132; AY818133; AY646179; AY818134; AY551934; AY651613; AY651610; AY651620; AY651617; AY651600; AY651611; AY651606; AY651618; AY651608; AY651607; AY651605; AY651609; AY651615; AY651616; AY651640; AY651614; AY651612; AY651621; AY651619; AY770995; and AY724786. Non-limiting examples of siRNA molecules targeting Influenza virus nucleic acid sequences include those described in U.S. Patent Publication No. 20070218122, the disclosure of which is herein incorporated by reference in its entirety for all purposes.

Exemplary hepatitis virus nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, supra). Exemplary Hepatitis C virus (HCV) nucleic acid sequences that can be silenced include, but are not limited to, the 5'-untranslated region (5'-UTR), the 3'-untranslated region (3'-UTR), the polyprotein translation initiation codon region, the internal ribosome entry site (IRES) sequence, and/or nucleic acid sequences encoding the core protein, the E1 protein, the E2 protein, the p7 protein, the NS2 protein, the NS3 protease/helicase, the NS4A protein, the NS4B protein, the NS5A protein, and/or the NS5B RNA-dependent RNA polymerase. HCV genome sequences are set forth in, e.g., Genbank Accession Nos. NC-004102 (HCV genotype 1a), AJ238799 (HCV genotype 1b), NC-009823 (HCV genotype 2), NC-009824 (HCV genotype 3), NC-009825 (HCV genotype 4), NC-009826 (HCV genotype 5), and NC-009827 (HCV genotype 6). Hepatitis A virus nucleic acid sequences are set forth in, e.g., Genbank Accession No. NC-001489; Hepatitis B virus nucleic acid sequences are set forth in, e.g., Genbank Accession No. NC-003977; Hepatitis D virus nucleic acid sequence are set forth in, e.g., Genbank Accession No. NC-001653; Hepatitis E virus nucleic acid sequences are set forth in, e.g., Genbank Accession No. NC-001434; and Hepatitis G virus nucleic acid sequences are set forth in, e.g., Genbank Accession No. NC-001710. Silencing of sequences that encode genes associated with viral infection and survival can conveniently be used in combination with the administration of conventional agents used to treat the viral condition. Non-limiting examples of siRNA molecules targeting hepatitis virus nucleic acid sequences include those described in U.S. Patent Publication Nos. 20060281175, 20050058982, and 20070149470; U.S. Pat. No. 7,348,314; and U.S. Provisional Application No. 61/162,127, filed Mar. 20, 2009, the disclosures of which are herein incorporated by reference in their entirety for all purposes.

Genes associated with metabolic diseases and disorders (e.g., disorders in which the liver is the target and liver diseases and disorders) include, for example, genes expressed in dyslipidemia (e.g., liver X receptors such as LXRα and LXRβ (Genback Accession No. NM-007121), farnesoid X receptors (FXR) (Genbank Accession No. NM-005123), sterol-regulatory element binding protein (SREBP), site-1 protease (SIP), 3-hydroxy-3-methylglutaryl coenzyme-A reductase (HMG coenzyme-A reductase), apolipoprotein B (ApoB) (Genbank Accession No. NM-000384), apolipoprotein CIII (ApoC3) (Genbank Accession Nos. NM-000040 and NG-008949 REGION: 5001.8164), and apolipoprotein E (ApoE) (Genbank Accession Nos. NM-000041 and NG-007084 REGION: 5001.8612)); and diabetes (e.g., glucose 6-phosphatase) (see, e.g., Forman et al., *Cell,* 81:687 (1995); Seol et al., *Mol. Endocrinol.,* 9:72 (1995), Zavacki et al., *Proc. Natl. Acad. Sci. USA,* 94:7909 (1997); Sakai et al., *Cell,* 85:1037-1046 (1996); Duncan et al., *J. Biol. Chem.,* 272:12778-12785 (1997); Willy et al., *Genes Dev.,* 9:1033-1045 (1995); Lehmann et al., *J. Biol. Chem.,* 272:3137-3140 (1997); Janowski et al., *Nature,* 383:728-731 (1996); and Peet et al., *Cell,* 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder. Non-limiting examples of siRNA molecules targeting the ApoB gene include those described in U.S. Patent Publication No. 20060134189, the disclosure of which is herein incorporated by reference in its entirety for all purposes. Non-limiting examples of siRNA molecules targeting the ApoC3 gene include those described in U.S. Provisional Application No. 61/147,235, filed Jan. 26, 2009, the disclosure of which is herein incorporated by reference in its entirety for all purposes.

Examples of gene sequences associated with tumorigenesis and cell transformation (e.g., cancer or other neoplasia) include mitotic kinesins such as Eg5 (KSP, KIF11; Genbank Accession No. NM-004523); serine/threonine kinases such as polo-like kinase 1 (PLK-1) (Genbank Accession No. NM-005030; Barr et al., *Nat. Rev. Mol. Cell. Biol.,* 5:429-440 (2004)); tyrosine kinases such as WEE1 (Genbank Accession Nos. NM-003390 and NM-001143976); inhibitors of apoptosis such as XIAP (Genbank Accession No. NM-001167); COP9 signalosome subunits such as CSN1, CSN2, CSN3, CSN4, CSN5 (JAB1; Genbank Accession No. NM-006837); CSN6, CSN7A, CSN7B, and CSN8; ubiquitin ligases such as COP1 (RFWD2; Genbank Accession Nos. NM-022457 and NM-001001740); and histone deacetylases such as HDAC1, HDAC2 (Genbank Accession No. NM-001527), HDAC3, HDAC4, HDAC5, HDAC6, HDAC7, HDAC8, HDAC9, etc. Non-limiting examples of siRNA molecules targeting the Eg5 and XIAP genes include those described in U.S. patent application Ser. No. 11/807,872, filed May 29, 2007, the disclosure of which is herein incorporated by reference in its entirety for all purposes. Non-limiting examples of siRNA molecules targeting the PLK-1 gene include those described in U.S. Patent Publication Nos. 20050107316 and 20070265438; and U.S. patent application Ser. No. 12/343,342, filed Dec. 23, 2008, the disclosures of which are herein incorporated by reference in their entirety for all purposes. Non-limiting examples of siRNA molecules targeting the CSN5 gene include those described in U.S. Provisional Application No. 61/045,251, filed Apr. 15, 2008, the disclosure of which is herein incorporated by reference in its entirety for all purposes.

Additional examples of gene sequences associated with tumorigenesis and cell transformation include translocation sequences such as MLL fusion genes, BCR-ABL (Wilda et al., *Oncogene,* 21:5716 (2002); Scherr et al., *Blood,* 101:1566 (2003)), TEL-AML1, EWS-FLI1, TLS-FUS, PAX3-FKHR, BCL-2, AML1-ETO, and AML1-MTG8 (Heidenreich et al., *Blood,* 101:3157 (2003)); overexpressed sequences such as multidrug resistance genes (Nieth et al., *FEBS Lett.,* 545:144 (2003); Wu et al, *Cancer Res.* 63:1515 (2003)), cyclins (Li et al., *Cancer Res.,* 63:3593 (2003); Zou et al., *Genes Dev.,* 16:2923 (2002)), beta-catenin (Verma et al., *Clin Cancer Res.,* 9:1291 (2003)), telomerase genes (Kosciolek et al., *Mol Cancer Ther.,* 2:209 (2003)), c-MYC, N-MYC, BCL-2, growth factor receptors (e.g., EGFR/ErbB1 (Genbank Accession Nos. NM-005228, NM-201282, NM-201283, and NM-201284; see also, Nagy et al. *Exp. Cell Res.,* 285:39-49 (2003), ErbB2/HER-2 (Genbank Accession Nos. NM-004448 and NM-001005862), ErbB3 (Genbank Accession Nos. NM-001982 and NM-001005915), and ErbB4 (Genbank Accession Nos. NM-005235 and NM-001042599); and mutated sequences such as RAS (reviewed in Tuschl and Borkhardt, *Mol. Interventions,* 2:158 (2002)). Non-limiting examples of siRNA molecules targeting the EGFR gene include those described in U.S. patent application Ser. No. 11/807,872, filed May 29, 2007, the disclosure of which is herein incorporated by reference in its entirety for all purposes.

Silencing of sequences that encode DNA repair enzymes find use in combination with the administration of chemotherapeutic agents (Collis et al., *Cancer Res.,* 63:1550 (2003)). Genes encoding proteins associated with tumor migration are also target sequences of interest, for example, integrins, selectins, and metalloproteinases. The foregoing examples are not exclusive. Those of skill in the art will understand that any whole or partial gene sequence that facilitates or promotes tumorigenesis or cell transformation, tumor growth, or tumor migration can be included as a template sequence.

Angiogenic genes are able to promote the formation of new vessels. Of particular interest is vascular endothelial growth factor (VEGF) (Reich et al., *Mol. Vis.,* 9:210 (2003)) or VEGFR. siRNA sequences that target VEGFR are set forth in, e.g., GB 2396864; U.S. Patent Publication No. 20040142895; and CA 2456444, the disclosures of which are herein incorporated by reference in their entirety for all purposes.

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see, e.g., U.S. Pat. No. 6,174,861), angiostatin (see, e.g., U U.S. Pat. No. 5,639,725), and VEGFR2 (see, e.g., Decaussin et al., *J. Pathol.,* 188: 369-377 (1999)), the disclosures of which are herein incorporated by reference in their entirety for all purposes.

Immunomodulator genes are genes that modulate one or more immune responses. Examples of immunomodulator genes include, without limitation, cytokines such as growth factors (e.g., TGF-α, TGF-β, EGF, FGF, IGF, NGF, PDGF, CGF, GM-CSF, SCF, etc.), interleukins (e.g., IL-2, IL-4, IL-12 (Hill et al., *J. Immunol.,* 171:691 (2003)), IL-15, IL-18, IL-20, etc.), interferons (e.g., IFN-α, IFN-β, IFN-γ, etc.) and TNF. Fas and Fas ligand genes are also immunomodulator target sequences of interest (Song et al., Nat. Med., 9:347 (2003)). Genes encoding secondary signaling molecules in hematopoietic and lymphoid cells are also included in the present invention, for example, Tec family kinases such as Bruton's tyrosine kinase (Btk) (Heinonen et al., *FEBS Lett.,* 527:274 (2002)).

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include, but are not limited to, cytokines, growth factors, interleukins, interferons, erythropoietin (EPO), insulin, glucagon, G-protein coupled receptor ligands, etc. Templates coding for an expansion of trinucleotide repeats (e.g., CAG repeats) find use in silencing pathogenic sequences in neurodegenerative disorders caused by the expansion of trinucleotide repeats, such as spinobulbular muscular atrophy and Huntington's Disease (Caplen et al., *Hum. Mol. Genet.,* 11:175 (2002)).

Certain other target genes, which may be targeted by a nucleic acid (e.g., by siRNA) to downregulate or silence the expression of the gene, include but are not limited to, Actin, Alpha 2, Smooth Muscle, Aorta (ACTA2), Alcohol dehydrogenase 1A (ADH1A), Alcohol dehydrogenase 4 (ADH4), Alcohol dehydrogenase 6 (ADH6), Afamin (AFM), Angiotensinogen (AGT), Serine-pyruvate aminotransferase (AGXT), Alpha-2-HS-glycoprotein (AHSG), Aldo-keto reductase family 1 member C4 (AKR1C4), Serum albumin (ALB), alpha-1-microglobulin/bikunin precursor (AMBP), Angiopoietin-related protein 3 (ANGPTL3), Serum amyloid P-component (APCS), Apolipoprotein A-II (APOA2), Apolipoprotein B-100 (APOB), Apolipoprotein C3 (APOC3), Apolipoprotein C—IV (APOC4), Apolipoprotein F (APOF), Beta-2-glycoprotein 1 (APOH), Aquaporin-9 (AQP9), Bile acid-CoA:amino acid N-acyltransferase (BAAT), C4b-binding protein beta chain (C4BPB), Putative uncharacterized protein encoded by LINC01554 (C5orf27), Complement factor 3 (C3), Complement Factor 5 (C5), Complement component C6 (C6), Complement component C8 alpha chain (C8A), Complement component C8 beta chain (C8B), Complement component C8 gamma chain (C8G), Complement component C9 (C9), Calmodulin Binding Transcription Activator 1 (CAMTA1), CD38 (CD38), Complement Factor B (CFB), Complement factor H-related protein 1 (CFHR1), Complement factor H-related protein 2 (CFHR2), Complement factor H-related protein 3 (CFHR3), Cannabinoid receptor 1 (CNR1), ceruloplasmin (CP), carboxypeptidase B2 (CPB2), Connective tissue growth factor (CTGF), C—X—C motif chemokine 2 (CXCL2), Cytochrome P450 1A2 (CYP1A2), Cytochrome P450 2A6 (CYP2A6), Cytochrome P450 2C8 (CYP2C8), Cytochrome P450 2C9 (CYP2C9), Cytochrome P450 Family 2 Subfamily D Member 6 (CYP2D6), Cytochrome P450 2E1 (CYP2E1), Phylloquinone omega-hydroxylase CYP4F2 (CYP4F2), 7-alpha-hydroxycholest-4-en-3-one 12-alpha-hydroxylase (CYP8B1), Dipeptidyl peptidase 4 (DPP4), coagulation factor 12 (F12), coagulation factor II (thrombin) (F2), coagulation factor IX (F9), fibrinogen alpha chain (FGA), fibrinogen beta chain (FGB), fibrinogen gamma chain (FGG), fibrinogen-like 1 (FGL1), flavin containing monooxygenase 3 (FMO3), flavin containing monooxygenase 5 (FMO5), group-specific component (vitamin D binding protein) (GC), Growth hormone receptor (GHR), glycine N-methyltransferase (GNMT), hyaluronan binding protein 2 (HABP2), hepcidin antimicrobial peptide (HAMP), hydroxyacid oxidase (glycolate oxidase) 1 (HAO1), HGF activator (HGFAC), haptoglobin-related protein; haptoglobin (HPR), hemopexin (HPX), histidine-rich glycoprotein (HRG), hydroxysteroid (11-beta) dehydrogenase 1 (HSD11B1), hydroxysteroid (17-beta) dehydrogenase 13 (HSD17B13), Inter-alpha-trypsin inhibitor heavy chain H1 (ITIH1), Inter-alpha-trypsin inhibitor heavy chain H2 (ITIH2), Inter-alpha-trypsin inhibitor heavy chain H3 (ITIH3), Inter-alpha-trypsin inhibitor heavy chain H4 (ITIH4), Prekallikrein (KLKB1), Lactate dehydrogenase A (LDHA), liver expressed antimicrobial peptide 2 (LEAP2), leukocyte cell-derived chemotaxin 2 (LECT2), Lipoprotein (a) (LPA), mannan-binding lectin serine peptidase 2 (MASP2), S-adenosylmethionine synthase isoform type-1 (MAT1A), NADPH Oxidase 4 (NOX4), Poly [ADP-ribose]polymerase 1 (PARP1), paraoxonase 1 (PON1), paraoxonase 3 (PON3), Vitamin K-dependent protein C (PROC), Retinol dehydrogenase 16 (RDH16), serum amyloid A4, constitutive (SAA4), serine dehydratase (SDS), Serpin Family A Member 1 (SERPINA1), Serpin A11 (SERPINA11), Kallistatin (SERPINA4), Corticosteroid-binding globulin (SERPINA6), Antithrombin-III (SERPINC1), Heparin cofactor 2 (SERPIND1), Serpin Family H Member 1 (SERPINH1), Solute Carrier Family 5 Member 2 (SLC5A2), Sodium/bile acid cotransporter (SLC10A1), Solute carrier family 13 member 5 (SLC13A5), Solute carrier family 22 member 1 (SLC22A1), Solute carrier family 25 member 47 (SLC25A47), Solute carrier family 2, facilitated glucose transporter member 2 (SLC2A2), Sodium-coupled neutral amino acid transporter 4 (SLC38A4), Solute carrier organic anion transporter family member 1B1 (SLCO1B1), Sphingomyelin Phosphodiesterase 1 (SMPD1), Bile salt sulfotransferase (SULT2A1), tyrosine aminotransferase (TAT), tryptophan 2,3-dioxygenase (TDO2), UDP glucuronosyltransferase 2 family, polypeptide B10 (UGT2B10), UDP glucuronosyltransferase 2 family, polypeptide B15 (UGT2B15), UDP glucuronosyltransferase 2 family, polypeptide B4 (UGT2B4) and vitronectin (VTN).

In addition to its utility in silencing the expression of any of the above-described genes for therapeutic purposes, certain nucleic acids (e.g., siRNA) described herein are also useful in research and development applications as well as diagnostic, prophylactic, prognostic, clinical, and other healthcare applications. As a non-limiting example, certain nucleic acids (e.g., siRNA) can be used in target validation studies directed at testing whether a gene of interest has the potential to be a therapeutic target. Certain nucleic acids (e.g., siRNA) can also be used in target identification studies aimed at discovering genes as potential therapeutic targets.

CRISPR

Targeted genome editing has progressed from being a niche technology to a method used by many biological researchers. This progression has been largely fueled by the emergence of the clustered, regularly interspaced, short palindromic repeat (CRISPR) technology (see, e.g., Sander et al., *Nature Biotechnology,* 32(4), 347-355, including Supplementary Information (2014) and International Publication Numbers WO 2016/197132 and WO 2016/197133). Accordingly, provided herein are improvements (e.g., lipid nanoparticles and formulations thereof) that can be used in combination with CRISPR technology to treat diseases, such as HBV. Regarding the targets for using CRISPR, the guide RNA (gRNA) utilized in the CRISPR technology can be designed to target specifically identified sequences, e.g., target genes, e.g., of the HBV genome. Examples of such target sequences are provided in International Publication Number WO 2016/197132. Further, International Publication Number WO 2013/151665 (e.g., see Table 6; which document is specifically incorporated by reference, particularly including Table 6, and the associated Sequence Listing) describes about 35,000 mRNA sequences, claimed in the context of an mRNA expression construct. Certain embodiments of the present invention utilize CRISPR technology to target the expression of any of these sequences. Certain embodiments of the present invention may also utilize CRISPR technology to target the expression of a target gene discussed herein.

aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.,* 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., “AA”, “UU”, “dTdT”, etc.). In other embodiments, the 3' antisense overhang contains one, two, three, four, or more nontargeting nucleotides (e.g., “AA”, “UU”, “dTdT”, etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In other embodiments, aiRNA molecules may be used to silence the expression of any of the target genes set forth above, such as, e.g., genes associated with viral infection and survival, genes associated with metabolic diseases and disorders, genes associated with tumorigenesis and cell transformation, angiogenic genes, immunomodulator genes such as those associated with inflammatory and autoimmune responses, ligand receptor genes, and genes associated with neurodegenerative disorders.

miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science,* 294:853-858; Lau et al., *Science,* 294:858-862; and Lee et al., *Science,* 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature,* 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., Cell, 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNA molecules may be used to silence the expression of any of the target genes set forth above, such as, e.g., genes associated with viral infection and survival, genes associated with metabolic diseases and disorders, genes associated with tumorigenesis and cell transformation, angiogenic genes, immunomodulator genes such as those associated with inflammatory and autoimmune responses, ligand receptor genes, and genes associated with neurodegenerative disorders.

In other embodiments, one or more agents that block the activity of a miRNA targeting an mRNA of interest are administered using a lipid particle of the invention (e.g., a nucleic acid-lipid particle). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

Antisense Oligonucleotides

In one embodiment, the nucleic acid is an antisense oligonucleotide directed to a target gene or sequence of interest. The terms "antisense oligonucleotide" or "antisense" include oligonucleotides that are complementary to a targeted polynucleotide sequence. Antisense oligonucleotides are single strands of DNA or RNA that are complementary to a chosen sequence. Antisense RNA oligonucleotides prevent the translation of complementary RNA strands by binding to the RNA. Antisense DNA oligonucleotides can be used to target a specific, complementary (coding or non-coding) RNA. If binding occurs, this DNA/RNA hybrid can be degraded by the enzyme RNase H. In a particular embodiment, antisense oligonucleotides comprise from about 10 to about 60 nucleotides, more preferably from about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (see, U.S. Pat. Nos. 5,739,119 and 5,759,829). Furthermore, examples of antisense inhibition have been demonstrated with the nuclear protein cyclin, the multiple drug resistance gene (MDR1), ICAM-1, E-selectin, STK-1, striatal GABAA receptor, and human EGF (see, Jaskulski et al., *Science,* 240:1544-6 (1988); Vasanthakumar et al., *Cancer Commun.,* 1:225-32 (1989); Penis et al., *Brain Res Mol Brain Res.,* 15; 57:310-20 (1998); and U.S. Pat. Nos. 5,801,154; 5,789,573; 5,718,709 and 5,610,288). Moreover, antisense constructs have also been described that inhibit and can be used to treat a variety of abnormal cellular proliferations, e.g., cancer (see, U.S. Pat. Nos. 5,747,470; 5,591,317; and 5,783,683). The disclosures of these references are herein incorporated by reference in their entirety for all purposes.

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.,* 25:3389-402 (1997)).

Ribozymes

According to another embodiment of the invention, nucleic acid-lipid particles are associated with ribozymes. Ribozymes are RNA-protein complexes having specific catalytic domains that possess endonuclease activity (see, Kim et al., *Proc. Natl. Acad. Sci. USA.,* 84:8788-92 (1987); and Forster et al., *Cell,* 49:211-20 (1987)). For example, a large number of ribozymes accelerate phosphoester transfer reactions with a high degree of specificity, often cleaving only one of several phosphoesters in an oligonucleotide substrate (see, Cech et al., *Cell,* 27:487-96 (1981); Michel et al., *J. Mol. Biol.,* 216:585-610 (1990); Reinhold-Hurek et al., *Nature,* 357:173-6 (1992)). This specificity has been attributed to the requirement that the substrate bind via specific base-pairing interactions to the internal guide sequence ("IGS") of the ribozyme prior to chemical reaction.

At least six basic varieties of naturally-occurring enzymatic RNA molecules are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, hepatitis δ virus, group I intron or RNaseP RNA (in association with an RNA guide sequence), or *Neurospora* VS RNA motif, for example. Specific examples of hammerhead motifs are described in, e.g., Rossi et al., *Nucleic Acids Res.,* 20:4559-65 (1992). Examples of hairpin motifs are described in, e.g., EP 0360257, Hampel et al., *Biochemistry,* 28:4929-33 (1989); Hampel et al., *Nucleic Acids Res.,* 18:299-304 (1990); and U.S. Pat. No. 5,631,359. An example of the hepatitis δ virus motif is described in, e.g., Perrotta et al., *Biochemistry,* 31:11843-52 (1992). An example of the RNaseP motif is described in, e.g., Guerrier-Takada et al., *Cell,* 35:849-57 (1983). Examples of the *Neurospora* VS RNA ribozyme motif is described in, e.g., Saville et al., *Cell,* 61:685-96 (1990); Saville et al., *Proc. Natl. Acad. Sci. USA,* 88:8826-30 (1991); Collins et al., *Biochemistry,* 32:2795-9 (1993). An example of the Group I intron is described in, e.g., U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus, the ribozyme constructs need not be limited to specific motifs mentioned herein. The disclosures of these references are herein incorporated by reference in their entirety for all purposes.

Methods of producing a ribozyme targeted to any polynucleotide sequence are known in the art. Ribozymes may be designed as described in, e.g., PCT Publication Nos. WO 93/23569 and WO 94/02595, and synthesized to be tested in vitro and/or in vivo as described therein. The disclosures of these PCT publications are herein incorporated by reference in their entirety for all purposes.

Ribozyme activity can be optimized by altering the length of the ribozyme binding arms or chemically synthesizing ribozymes with modifications that prevent their degradation by serum ribonucleases (see, e.g., PCT Publication Nos. WO 92/07065, WO 93/15187, WO 91/03162, and WO 94/13688; EP 92110298.4; and U.S. Pat. No. 5,334,711, which describe various chemical modifications that can be made to the sugar moieties of enzymatic RNA molecules, the disclosures of which are each herein incorporated by reference in their entirety for all purposes), modifications which enhance their efficacy in cells, and removal of stem II bases to shorten RNA synthesis times and reduce chemical requirements.

Immunostimulatory Oligonucleotides

Nucleic acids associated with lipid particles of the present invention may be immunostimulatory, including immunostimulatory oligonucleotides (ISS; single- or double-stranded) capable of inducing an immune response when administered to a subject, which may be a mammal such as a human. ISS include, e.g., certain palindromes leading to hairpin secondary structures (see, Yamamoto et al., *J. Immunol.,* 148:4072-6 (1992)), or CpG motifs, as well as other known ISS features (such as multi-G domains; see; PCT Publication No. WO 96/11266, the disclosure of which is herein incorporated by reference in its entirety for all purposes).

Immunostimulatory nucleic acids are considered to be non-sequence specific when it is not required that they specifically bind to and reduce the expression of a target sequence in order to provoke an immune response. Thus, certain immunostimulatory nucleic acids may comprise a sequence corresponding to a region of a naturally-occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in the CpG dinucleotide is methylated. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of the CpG dinucleotides comprises a methylated cytosine. Examples of immunostimulatory oligonucleotides suitable for use in the compositions and methods of the present invention are described in PCT Application No. PCT/US08/88676, filed Dec. 31, 2008, PCT Publication Nos. WO 02/069369 and WO 01/15726, U.S. Pat. No. 6,406,705, and Raney et al., *J. Pharm. Exper. Ther.,* 298: 1185-92 (2001), the disclosures of which are each herein incorporated by reference in their entirety for all purposes. In certain embodiments, the oligonucleotides used in the compositions and methods of the invention have a phosphodiester ("PO") backbone or a phosphorothioate ("PS") backbone, and/or at least one methylated cytosine residue in a CpG motif.

mRNA

In certain embodiments, the nucleic acid is one or more mRNA molecules (e.g., a cocktail of mRNA molecules).

Modifications to mRNA mRNA used in the practice of the present invention can include one, two, or more than two nucleoside modifications. In some embodiments, the modified mRNA exhibits reduced degradation in a cell into which the mRNA is introduced, relative to a corresponding unmodified mRNA.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methy 1-pseudouridine, 4-thio-1-methy 1-pseudouridine, 2-thio-1-methy 1-pseudouridine, 1-methy 1-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In specific embodiments, a modified nucleoside is 5'-0-(1-Thiophosphate)-Adenosine, 5'-0-(1-Thiophosphate)-Cytidine, 5'-0-(1-Thiophosphate)-Guanosine, 5'-0-(1-Thiophosphate)-Uridine or 5'-0-(1-Thiophosphate)-Pseudouridine. The $\alpha$-thio substituted phosphate moiety is provided to confer stability to RNA polymers through the unnatural phosphorothioate backbone linkages. Phosphorothioate RNA have increased nuclease resistance and subsequently a longer half-life in a cellular environment. Phosphorothioate linked nucleic acids are expected to also reduce the innate immune response through weaker binding/activation of cellular innate immune molecules.

In certain embodiments it is desirable to intracellularly degrade a modified nucleic acid introduced into the cell, for example if precise timing of protein production is desired. Thus, the invention provides a modified nucleic acid containing a degradation domain, which is capable of being acted on in a directed manner within a cell.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxoguanosine, 7-methyl-8-oxo-guanosine, 1-methyl-6-thio-guanosine, N2-methyl-6-thio-guanosine, and N2,N2-dimethyl-6-thio-guanosine.

Optional Components of the Modified Nucleic Acids

In further embodiments, the modified nucleic acids may include other optional components, which can be beneficial in some embodiments. These optional components include, but are not limited to, untranslated regions, kozak sequences, intronic nucleotide sequences, internal ribosome entry site (IRES), caps and polyA tails. For example, a 5' untranslated region (UTR) and/or a 3' UTR may be provided, wherein either or both may independently contain one or more different nucleoside modifications. In such embodiments, nucleoside modifications may also be present in the translatable region. Also provided are nucleic acids containing a Kozak sequence.

Additionally, provided are nucleic acids containing one or more intronic nucleotide sequences capable of being excised from the nucleic acid.

Untranslated Regions (UTRs)

Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the mRNA used in the present invention to increase the stability of the molecule. The specific features can also be incorporated to ensure controlled down-regulation of the transcript in case they are misdirected to undesired organs sites.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue. The ribose sugars of the terminal and/or anteterminal transcribed nucleotides of the 5' end of the mRNA may optionally also be 2-0-methylated. 5'-decapping through hydrolysis and cleavage of the guanylate cap structure may target a nucleic acid molecule, such as an mRNA molecule, for degradation.

IRES Sequences mRNA containing an internal ribosome entry site (IRES) are also useful in the practice of the present invention. An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When mRNA are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (S1V) or cricket paralysis viruses (CrPV).

Poly-A Tails

During RNA processing, a long chain of adenine nucleotides (poly-A tail) may be added to a polynucleotide such as an mRNA molecules in order to increase stability. Immediately after transcription, the 3' end of the transcript may be cleaved to free a 3' hydroxyl. Then poly-A polymerase adds a chain of adenine nucleotides to the RNA. The process, called polyadenylation, adds a poly-A (SEQ ID NO: 5) tail that can be between 100 and 250 residues long.

Generally, the length of a poly-A (SEQ ID NO: 6) tail is greater than 30 nucleotides in length. In another embodiment, the poly-A (SEQ ID NO: 7) tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1000, 1100, 1200, 1300, 1400, 1500, 1600, 1700, 1800, 1900, 2,000, 2,500, and 3,000 nucleotides).

In this context the poly-A tail may be 10, 20, 30, 40, 50, 60, 70, 80, 90, or 100% greater in length than the modified mRNA. The poly-A tail may also be designed as a fraction of modified nucleic acids to which it belongs. In this context, the poly-A tail may be 10, 20, 30, 40, 50, 60, 70, 80, or 90% or more of the total length of the modified mRNA or the total length of the modified mRNA minus the poly-A tail.

Generating mRNA Molecules

Methods for isolating RNA, synthesizing RNA, hybridizing nucleic acids, making and screening cDNA libraries, and performing PCR are well known in the art (see, e.g., Gubler and Hoffman, Gene, 25:263-269 (1983); Sambrook et al., *Molecular Cloning, A Laboratory Manual* (2nd ed. 1989)); as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Encoded Polypeptides

The mRNA component of a nucleic acid-lipid particle described herein can be used to express a polypeptide of interest. Certain diseases in humans are caused by the absence or impairment of a functional protein in a cell type where the protein is normally present and active. The functional protein can be completely or partially absent due, e.g., to transcriptional inactivity of the encoding gene or due to the presence of a mutation in the encoding gene that renders the protein completely or partially non-functional. Examples of human diseases that are caused by complete or partial inactivation of a protein include X-linked severe combined immunodeficiency (X-SCID) and adrenoleukodystrophy (X-ALD). X-SCID is caused by one or more mutations in the gene encoding the common gamma chain protein that is a component of the receptors for several interleukins that are involved in the development and maturation of B and T cells within the immune system. X-ALD is caused by one or more mutations in a peroxisomal membrane transporter protein gene called ABCD1. Individuals afflicted with X-ALD have very high levels of long chain fatty acids in tissues throughout the body, which causes a variety of symptoms that may lead to mental impairment or death.

Attempts have been made to use gene therapy to treat some diseases caused by the absence or impairment of a functional protein in a cell type where the protein is normally present and active. Gene therapy typically involves introduction of a vector that includes a gene encoding a functional form of the affected protein, into a diseased person, and expression of the functional protein to treat the disease. Thus far, gene therapy has met with limited success. Additionally, certain aspects of delivering mRNA using LNPs have been described, e.g., in International Publication Numbers WO 2018/006052 and WO 2015/011633.

As such, there is a continuing need for improvement for expressing a functional form of a protein within a human who suffers from a disease caused by the complete or partial absence of the functional protein, and there is a need for improved delivery of nucleic acids (e.g., mRNA) via a methods and compositions, e.g., that can trigger less of an immune response to the therapy. Certain embodiments of the present invention are useful in this context. Thus, in certain embodiments, expression of the polypeptide ameliorates one or more symptoms of a disease or disorder. Certain compositions and methods of the invention may be useful for treating human diseases caused by the absence, or reduced levels, of a functional polypeptide within the human body. In other embodiments, certain LNP, compositions and methods of the invention may be useful for delivering or expressing a vaccine antigen, e.g., for treating cancer.

Self-Amplifying RNA

In certain embodiments, the nucleic acid is one or more self-amplifying RNA molecules. Self-amplifying RNA (sa-RNA) may also be referred to as self-replicating RNA, replication-competent RNA, replicons or RepRNA. RepRNA, referred to as self-amplifying mRNA when derived from positive-strand viruses, is generated from a viral genome lacking at least one structural gene; it can translate and replicate (hence "self-amplifying") without generating infectious progeny virus. In certain embodiments, the RepRNA technology may be used to insert a gene cassette encoding a desired antigen of interest. For example, the alphaviral genome is divided into two open reading frames (ORFs): the first ORF encodes proteins for the RNA dependent RNA polymerase (replicase), and the second ORF encodes structural proteins. In sa-RNA vaccine constructs, the ORF encoding viral structural proteins may be replaced with any antigen of choice, while the viral replicase remains an integral part of the vaccine and drives intracellular amplification of the RNA after immunization.

Other Active Agents

In certain embodiments, the active agent associated with the lipid particles of the invention may comprise one or more therapeutic proteins, polypeptides, or small organic molecules or compounds. Non-limiting examples of such therapeutically effective agents or drugs include oncology drugs (e.g., chemotherapy drugs, hormonal therapeutic agents, immunotherapeutic agents, radiotherapeutic agents, etc.), lipid-lowering agents, anti-viral drugs, anti-inflammatory compounds, antidepressants, stimulants, analgesics, antibiotics, birth control medication, antipyretics, vasodilators, anti-angiogenics, cytovascular agents, signal transduction inhibitors, cardiovascular drugs such as anti-arrhythmic agents, hormones, vasoconstrictors, and steroids. These active agents may be administered alone in the lipid particles of the invention, or in combination (e.g., co-administered) with lipid particles of the invention comprising nucleic acid, such as interfering RNA or mRNA.

Non-limiting examples of chemotherapy drugs include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan (CPT-11; Camptosar), topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), etc.), pharmaceutically acceptable salts thereof, stereoisomers thereof, derivatives thereof, analogs thereof, and combinations thereof.

Examples of conventional hormonal therapeutic agents include, without limitation, steroids (e.g., dexamethasone), finasteride, aromatase inhibitors, tamoxifen, and goserelin as well as other gonadotropin-releasing hormone agonists (GnRH).

Examples of conventional immunotherapeutic agents include, but are not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

Examples of conventional radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Additional oncology drugs that may be used according to the invention include, but are not limited to, alkeran, allopurinol, altretamine, amifostine, anastrozole, araC, arsenic trioxide, bexarotene, biCNU, carmustine, CCNU, celecoxib, cladribine, cyclosporin A, cytosine arabinoside, cytoxan, dexrazoxane, DTIC, estramustine, exemestane, FK506, gemtuzumab-ozogamicin, hydrea, hydroxyurea, idarubicin, interferon, letrozole, leustatin, leuprolide, litretinoin, megastrol, L-PAM, mesna, methoxsalen, mithramycin, nitrogen mustard, pamidronate, Pegademase, pentostatin, porfimer sodium, prednisone, rituxan, streptozocin, STI-571, taxotere, temozolamide, VM-26, toremifene, tretinoin, ATRA, valrubicin, and velban. Other examples of oncology drugs that may be used according to the invention are ellipticin and ellipticin analogs or derivatives, epothilones, intracellular kinase inhibitors, and camptothecins.

Non-limiting examples of lipid-lowering agents for treating a lipid disease or disorder associated with elevated triglycerides, cholesterol, and/or glucose include statins, fibrates, ezetimibe, thiazolidinediones, niacin, beta-blockers, nitroglycerin, calcium antagonists, fish oil, and mixtures thereof.

Examples of anti-viral drugs include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, immunovir, idoxuridine, imiquimod, indinavir, inosine, integrase inhibitors, interferon type III (e.g., IFN-λ molecules such as IFN-λ1, IFN-λ2, and IFN-λ3), interferon type II (e.g., IFN-γ), interferon type I (e.g., IFN-α such as PEGylated IFN-α, IFN-β, IFN-κ, IFN-δ, IFN—ε, IFN-τ, IFN-ω, and IFN-ζ), interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, pharmaceutically acceptable salts thereof, stereoisomers thereof, derivatives thereof, analogs thereof, and mixtures thereof.

Lipid Particles

The lipid particles of the invention typically comprise an active agent or therapeutic agent, a cationic lipid, a non-cationic lipid, and a conjugated lipid that inhibits aggregation of particles. In some embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In other embodiments, the lipid particles described herein are substantially non-toxic to mammals such as humans. The lipid particles of the invention typically have a mean diameter of from about 40 nm to about 150 nm, from about 50 nm to about 150 nm, from about 60 nm to about 130 nm, from about 70 nm to about 110 nm, or from about 70 to about 90 nm.

In preferred embodiments, the lipid particles of the invention are serum-stable nucleic acid-lipid particles (LNP) which comprise one or more nucleic acid molecules, such as an interfering RNA (e.g., siRNA, aiRNA, and/or miRNA) or mRNA; a cationic lipid (e.g., a cationic lipid of Formulas I, II, and/or III); a non-cationic lipid (e.g., cholesterol alone or mixtures of one or more phospholipids and cholesterol); and a conjugated lipid that inhibits aggregation of the particles (e.g., one or more PEG-lipid conjugates). The LNP may comprise at least 1, 2, 3, 4, 5, 6, 7, 8, 9, 10, or more unmodified and/or modified nucleic acid molecules. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

Non-Cationic Lipids

The non-cationic lipids used in the lipid particles of the invention (e.g., LNP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof such as cholestanol, cholestanone, cholestenone, coprostanol, cholesteryl-2'-hydroxyethyl ether, cholesteryl-4'-hydroxybutyl ether, and mixtures thereof.

In some embodiments, the non-cationic lipid present in the lipid particles (e.g., LNP) comprises or consists of cholesterol or a derivative thereof, e.g., a phospholipid-free lipid particle formulation. In other embodiments, the non-cationic lipid present in the lipid particles (e.g., LNP) comprises or consists of one or more phospholipids, e.g., a cholesterol-free lipid particle formulation. In further embodiments, the non-cationic lipid present in the lipid particles (e.g., LNP) comprises or consists of a mixture of one or more phospholipids and cholesterol or a derivative thereof.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 13 mol % to about 49.5 mol %, from about 20 mol % to about 45 mol %, from about 25 mol % to about 45 mol %, from about 30 mol % to about 45 mol %, from about 35 mol % to about 45 mol %, from about 20 mol % to about 40 mol %, from about 25 mol % to about 40 mol %, or from about 30 mol % to about 40 mol % of the total lipid present in the particle.

In certain embodiments, the cholesterol present in phospholipid-free lipid particles comprises from about 30 mol % to about 45 mol %, from about 30 mol % to about 40 mol %, from about 35 mol % to about 45 mol %, or from about 35 mol % to about 40 mol % of the total lipid present in the particle. As a non-limiting example, a phospholipid-free lipid particle may comprise cholesterol at about 37 mol % of the total lipid present in the particle.

In certain other embodiments, the cholesterol present in lipid particles containing a mixture of phospholipid and cholesterol comprises from about 30 mol % to about 40 mol %, from about 30 mol % to about 35 mol %, or from about 35 mol % to about 40 mol % of the total lipid present in the particle. As a non-limiting example, a lipid particle comprising a mixture of phospholipid and cholesterol may comprise cholesterol at about 34 mol % of the total lipid present in the particle.

In further embodiments, the cholesterol present in lipid particles containing a mixture of phospholipid and cholesterol comprises from about 10 mol % to about 30 mol %, from about 15 mol % to about 25 mol %, or from about 17 mol % to about 23 mol % of the total lipid present in the particle. As a non-limiting example, a lipid particle comprising a mixture of phospholipid and cholesterol may comprise cholesterol at about 20 mol % of the total lipid present in the particle.

In embodiments where the lipid particles contain a mixture of phospholipid and cholesterol or a cholesterol derivative, the mixture may comprise up to about 40, 45, 50, 55, or 60 mol % of the total lipid present in the particle. In certain instances, the phospholipid component in the mixture may comprise from about 2 mol % to about 12 mol %, from about 4 mol % to about 10 mol %, from about 5 mol % to about 10 mol %, from about 5 mol % to about 9 mol %, or from about 6 mol % to about 8 mol % of the total lipid present in the particle. As a non-limiting example, a lipid particle comprising a mixture of phospholipid and cholesterol may comprise a phospholipid such as DPPC or DSPC at about 7 mol % (e.g., in a mixture with about 34 mol % cholesterol) of the total lipid present in the particle. In certain other instances, the phospholipid component in the mixture may comprise from about 10 mol % to about 30 mol %, from about 15 mol % to about 25 mol %, or from about 17 mol % to about 23 mol % of the total lipid present in the particle. As another non-limiting example, a lipid particle comprising a mixture of phospholipid and cholesterol may comprise a phospholipid such as DPPC or DSPC at about 20 mol % (e.g., in a mixture with about 20 mol % cholesterol) of the total lipid present in the particle.

Lipid Conjugate

In addition to cationic and non-cationic lipids, the lipid particles of the invention (e.g., LNP) comprise a lipid conjugate. The conjugated lipid is useful in that it prevents the aggregation of particles. Suitable conjugated lipids include, but are not limited to, PEG-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes. Additional PEG-lipids include, without limitation, PEG-C-DOMG, 2 KPEG-DMG, and a mixture thereof.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-$NH_2$), monomethoxypolyethylene glycol-tresylate (MePEG-TRES), and monomethoxypolyethylene glycol-imidazolyl-carbonyl (MePEG-IM). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycolacetic acid (MePEG-$CH_2COOH$) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)C$CH_2CH_2$C(O)—), succinamidyl (—NHC(O)$CH_2CH_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Additional PEG-lipid conjugates suitable for use in the invention include, but are not limited to, compounds of formula:

A-B—C or a salt thereof, wherein:

A is ($C_1$-$C_6$)alkyl, ($C_3$-$C_8$)cycloalkyl, ($C_3$-$C_8$)cycloalkyl($C_1$-$C_6$)alkyl, ($C_1$-$C_6$)alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkylthio, or ($C_2$-$C_6$)alkanoyloxy, wherein any ($C_1$-

$C_6$)alkyl, ($C_3$-$C_8$)cycloalkyl, ($C_3$-$C_8$)cycloalkyl($C_1$-$C_6$) alkyl, ($C_1$-$C_6$)alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkylthio, and ($C_2$-$C_6$)alkanoyloxy is substituted with one or more anionic precursor groups, and wherein any ($C_1$-$C_6$)alkyl, ($C_3$-$C_8$)cycloalkyl, ($C_3$-$C_8$)cycloalkyl ($C_1$-$C_6$)alkyl, ($C_1$-$C_6$)alkoxy, ($C_2$-$C_6$)alkenyl, ($C_2$-$C_6$) alkynyl, ($C_1$-$C_6$)alkanoyl, ($C_1$-$C_6$)alkoxycarbonyl, ($C_1$-$C_6$)alkylthio, and ($C_2$-$C_6$)alkanoyloxy is optionally substituted with one or more groups independently selected from the group consisting of halo, hydroxyl, ($C_1$-$C_3$)alkoxy, ($C_1$-$C_6$)alkanoyl, ($C_1$-$C_3$)alkoxycarbonyl, ($C_1$-$C_3$)alkylthio, or ($C_2$-$C_3$)alkanoyloxy;

B is a polyethylene glycol chain having a molecular weight of from about 550 daltons to about 10,000 daltons;

C is -L-$R^a$

L is selected from the group consisting of a direct bond, —C(O)O—, —C(O)$NR^b$—, —$NR^b$—, —C(O)—, —$NR^b$C(O)O—, —$NR^b$C(O)$NR^b$—, —S—S—, —O—, —(O)C$CH_2CH_2$C(O)—, and —NHC(O) $CH_2CH_2$C(O)NH—;

$R^a$ is a branched ($C_{10}$-$C_{50}$)alkyl or branched ($C_{10}$-$C_{50}$) alkenyl wherein one or more carbon atoms of the branched ($C_{10}$-$C_{50}$)alkyl or branched ($C_{10}$-$C_{50}$)alkenyl have been replaced with —O—; and each $R^b$ is independently H or ($C_1$-$C_6$)alkyl.

The conjugated lipids may comprise a PEG-lipid including, e.g., a compound of formula A-PEG-diacylglycerol (DAG), A-PEG dialkyloxypropyl (DAA), A-PEG-phospholipid, A-PEG-ceramide (Cer), or mixtures thereof, wherein A is ($C_1$-$C_6$)alkyl, ($C_3$-$C_8$)cycloalkyl, ($C_3$-$C_8$)cycloalkyl ($C_1$-$C_6$)alkyl, ($C_1$-$C_6$)alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkylthio, or ($C_2$-$C_6$)alkanoyloxy, wherein any ($C_1$-$C_6$)alkyl, ($C_3$-$C_8$)cycloalkyl, ($C_3$-$C_8$)cycloalkyl($C_1$-$C_6$)alkyl, ($C_1$-$C_6$) alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkylthio, and ($C_2$-$C_6$)alkanoyloxy is substituted with one or more anionic precursor groups, and wherein any ($C_1$-$C_6$)alkyl, ($C_3$-$C_8$)cycloalkyl, ($C_3$-$C_8$)cycloalkyl($C_1$-$C_6$)alkyl, ($C_1$-$C_6$)alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkylthio, and ($C_2$-$C_6$)alkanoyloxy is optionally substituted with one or more groups independently selected from the group consisting of halo, hydroxyl, ($C_1$-$C_3$)alkoxy, ($C_1$-$C_6$)alkanoyl, ($C_1$-$C_3$)alkoxycarbonyl, ($C_1$-$C_3$)alkylthio, or ($C_2$-$C_3$)alkanoyloxy. The A-PEG-DAA conjugate may be A-PEG-dilauryloxypropyl (C12), A-PEG-dimyristyloxypropyl (C14), A-PEG-dipalmityloxypropyl (C16), or A-PEG-distearyloxypropyl (C18), or mixtures thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTR" or "polyamide" refers to, without limitation, compounds described in U.S. Pat. Nos. 6,320,017 and 6,586,559, the disclosures of which are herein incorporated by reference in their entirety for all purposes. These compounds include a compound having the formula:

(IV)

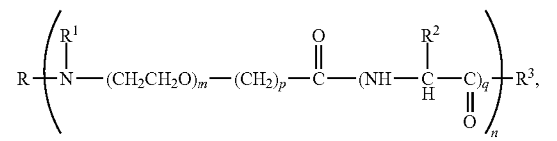

wherein R is a member selected from the group consisting of hydrogen, alkyl and acyl; $R^1$ is a member selected from the group consisting of hydrogen and alkyl; or optionally, R and R' and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, e.g., $R^1$ and $R^2$ are both myristyl (e.g., dimyristyl), $R^1$ and $R^2$ are both stearyl (e.g., distearyl), etc. Diacylglycerols have the following general formula:

(V)

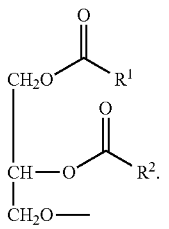

The term "dialkyloxypropyl" refers to a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(VI)

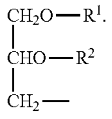

In a preferred embodiment, the PEG-lipid is a PEG-DAA conjugate having the following formula:

(VII)

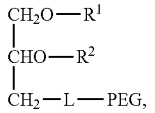

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, e.g., $R^1$ and $R^2$ are both myristyl (e.g., dimyristyl), R and $R^2$ are both stearyl (e.g., distearyl), etc.

In Formula VII above, the PEG has an average molecular weight ranging from about 550 daltons to about 10,000 daltons. In certain instances, the PEG has an average molecular weight of from about 500 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (e.g., a PEG-C-DAA conjugate). In another preferred embodiment, the non-ester containing linker moiety is an amido linker moiety (e.g., a PEG-A-DAA conjugate). In yet another preferred embodiment, the non-ester containing linker moiety is a succinamidyl linker moiety (e.g., a PEG-S-DAA conjugate).

In particular embodiments, the PEG-lipid conjugate is selected from:

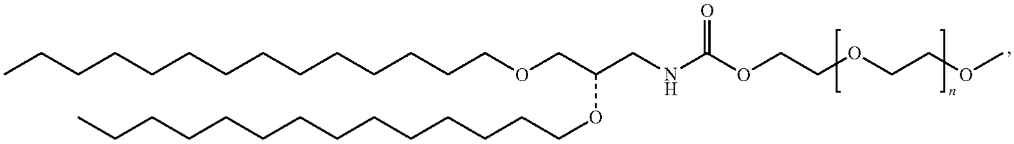

, and (PEG-C-DMA)

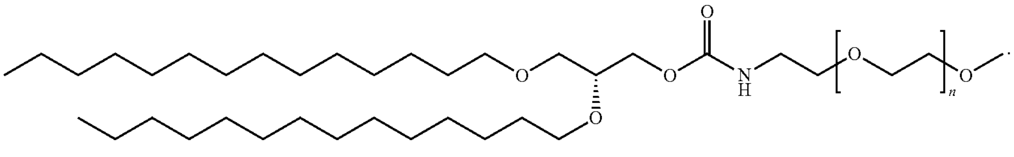

(PEG-C-DOMG)

In one embodiment, n is selected so that the resulting polymer chain has a molecular weight of about 2000.

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a dilauryloxypropyl ($C_{12}$)-PEG conjugate, dimyristyloxypropyl ($C_{14}$)-PEG conjugate, a dipalmityloxypropyl ($C_{16}$)-PEG conjugate, or a distearyloxypropyl ($C_{18}$)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W."

Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

The lipid conjugate (e.g., PEG-lipid) typically comprises from about 0.1 mol % to about 10 mol %, from about 0.5 mol % to about 10 mol %, from about 1 mol % to about 10 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % of the total lipid present in the particle.

One of ordinary skill in the art will appreciate that the concentration of the lipid conjugate can be varied depending on the lipid conjugate employed and the rate at which the nucleic acid-lipid particle is to become fusogenic.

By controlling the composition and concentration of the lipid conjugate, one can control the rate at which the lipid conjugate exchanges out of the nucleic acid-lipid particle and, in turn, the rate at which the nucleic acid-lipid particle becomes fusogenic. For instance, when a PEG-phosphatidylethanolamine conjugate or a PEG-ceramide conjugate is used as the lipid conjugate, the rate at which the nucleic acid-lipid particle becomes fusogenic can be varied, for example, by varying the concentration of the lipid conjugate, by varying the molecular weight of the PEG, or by varying the chain length and degree of saturation of the acyl chain groups on the phosphatidylethanolamine or the ceramide. In addition, other variables including, for example, pH, temperature, ionic strength, etc. can be used to vary and/or control the rate at which the nucleic acid-lipid particle becomes fusogenic. Other methods which can be used to control the rate at which the nucleic acid-lipid particle becomes fusogenic will become apparent to those of skill in the art upon reading this disclosure.

Preparation of Lipid Particles

The lipid particles of the present invention, e.g., LNP, in which an active agent or therapeutic agent such as a nucleic acid molecule is encapsulated in a lipid bilayer and is protected from degradation, can be formed by any method known in the art including, but not limited to, a continuous mixing method or a direct dilution process.

In preferred embodiments, the cationic lipids are lipids of Formula I, II, and III, or combinations thereof. In other preferred embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, or combinations thereof.

In certain embodiments, the present invention provides for LNP produced via a continuous mixing method, e.g., a process that includes providing an aqueous solution comprising a nucleic acid, such as an interfering RNA or mRNA, in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., interfering RNA or mRNA). This process and the apparatus for carrying this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (e.g., aqueous solution) to produce a nucleic acid-lipid particle.

The LNP formed using the continuous mixing method typically have a size of from about 40 nm to about 150 nm, from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In another embodiment, the present invention provides for LNP produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As a non-limiting example, a liposome solution in 45% ethanol when introduced into the collection vessel containing an equal volume of dilution buffer will advantageously yield smaller particles.

In yet another embodiment, the present invention provides for LNP produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 1800 flows; however, connectors providing shallower angles can be used, e.g., from about 270 to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes are described in detail in U.S. Patent Publication No. 20070042031, the disclosure of which is herein incorporated by reference in its entirety for all purposes.

The LNP formed using the direct dilution process typically have a size of from about 40 nm to about 150 nm, from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

If needed, the lipid particles of the invention (e.g., LNP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids in the LNP are precondensed as described in, e.g., U.S. patent application Ser. No. 09/744,103, the disclosure of which is herein incorporated by reference in its entirety for all purposes.

In other embodiments, the methods will further comprise adding non-lipid polycations which are useful to effect the lipofection of cells using the present compositions. Examples of suitable non-lipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed LNP will range from about 0.01 to about 0.2, from about 0.02 to about 0.1, from about 0.03 to about 0.1, or from about 0.01 to about 0.08. The ratio of the starting materials also falls within this range. In other embodiments, the LNP preparation uses about 400 pg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed LNP will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), about 5 (5:1), 6 (6:1), 7 (7:1), 8 (8:1), 9 (9:1), (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), 25 (25:1), 26 (26:1), 27 (27:1), 28 (28:1), 29 (29:1) or 30 (30:1). The ratio of the starting materials also typically falls within this range.

As previously discussed, the conjugated lipid may further include a CPL. A variety of general methods for making LNP-CPLs (CPL-containing LNP) are discussed herein. Two general techniques include "post-insertion" technique, that is, insertion of a CPL into, for example, a pre-formed LNP, and the "standard" technique, wherein the CPL is included in the lipid mixture during, for example, the LNP formation steps. The post-insertion technique results in LNP having CPLs mainly in the external face of the LNP bilayer membrane, whereas standard techniques provide LNP having CPLs on both internal and external faces. The method is especially useful for vesicles made from phospholipids (which can contain cholesterol) and also for vesicles containing PEG-lipids (such as PEG-DAAs and PEG-DAGs). Methods of making LNP-CPL, are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

Other methods for generating LNP may be found, for example, in U.S. Pat. No. 9,005,654 and PCT Publication No. WO 2007/012191, the disclosures of which are herein incorporated by reference in their entirety for all purposes.

Kits

The present invention also provides lipid particles (e.g., LNP) in kit form. The kit may comprise a container which is compartmentalized for holding the various elements of the lipid particles (e.g., the active agents or therapeutic agents such as nucleic acids and the individual lipid components of the particles). In some embodiments, the kit may further comprise an endosomal membrane destabilizer (e.g., calcium ions). The kit typically contains the lipid particle compositions of the present invention, preferably in dehydrated form, with instructions for their rehydration and administration.

As explained herein, the lipid particles of the invention (e.g., LNP) can be tailored to preferentially target particular tissues, organs, or tumors of interest. In certain instances, preferential targeting of lipid particles such as LNP may be carried out by controlling the composition of the particle itself. For instance, as set forth in Example 11, it has been found that the 1:57 PEG-cDSA LNP formulation can be used to preferentially target tumors outside of the liver, whereas the 1:57 PEG-cDMA LNP formulation can be used to preferentially target the liver (including liver tumors).

In certain other instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

Administration of Lipid Particles

Once formed, the lipid particles of the invention (e.g., LNP) are useful for the introduction of active agents or therapeutic agents (e.g., nucleic acids, such as interfering RNA or mRNA) into cells. Accordingly, the present invention also provides methods for introducing an active agent or therapeutic agent such as a nucleic acid (e.g., interfering RNA or mRNA) into a cell. The methods are carried out in vitro or in vivo by first forming the particles as described above and then contacting the particles with the cells for a period of time sufficient for delivery of the active agent or therapeutic agent to the cells to occur.

The lipid particles of the invention (e.g., LNP) can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles of the invention (e.g., LNP) can be administered either alone or in a mixture with a pharmaceutically-acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically-acceptable carrier. Lipids may also be frozen to stabilize. For example, lipids may be stored in −20 C in a high salt concentration (e.g., 500 mM NaCl) in Tris buffer at pH 8. As a further example, lipids may also be stored in −80C storage in a mixture of sucrose and maltose in Tris buffer at pH 8.Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human.

The pharmaceutically-acceptable carrier is generally added following particle formation. Thus, after the particle is formed, the particle can be diluted into pharmaceutically-acceptable carriers such as normal buffered saline.

The concentration of particles in the pharmaceutical formulations can vary widely, e.g., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are nonimmunogenic, are small in size, and are suitable for repeat dosing.

For in vivo administration, administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, e.g., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

The compositions of the present invention, either alone or in combination with other suitable components, can be made into aerosol formulations (e.g., they can be "nebulized") to be administered via inhalation (e.g., intranasally or intratracheally) (see, Brigham et al., *Am. J. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroethylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent such as nucleic acid (e.g., interfering RNA or mRNA) suspended in diluents such as water, saline, or PEG 400; (b) capsules, sachets, or tablets, each containing a predetermined amount of a therapeutic agent such as nucleic acid (e.g., interfering RNA or mRNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA or mRNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing nucleic acid-lipid particles such as LNP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic agent (e.g., nucleic acid) to lipid, the particular therapeutic agent (e.g., nucleic acid) used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

In Vitro Administration

For in vitro applications, the delivery of therapeutic agents such as nucleic acids (e.g., interfering RNA or mRNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 pg/ml, more preferably about 0.1 pg/ml.

Using an Endosomal Release Parameter (ERP) assay, the delivery efficiency of the LNP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of LNP based on their relative effect on binding/uptake or fusion with/destabilization of the endosomal membrane. This assay allows one to determine quantitatively how each component of the LNP or other lipid particle affects delivery efficiency, thereby optimizing the LNP or other lipid particle. Usually, an ERP assay measures expression of a reporter protein (e.g., luciferase, β-galactosidase, green fluorescent protein (GFP), etc.), and in some instances, a LNP formulation optimized for an expression plasmid will also be appropriate for encapsulating an interfering RNA or mRNA. In other instances, an ERP assay can be adapted to measure downregulation of transcription or translation of a target sequence in the presence or absence of an interfering RNA (e.g., siRNA). In other instances, an ERP assay can be adapted to measure the expression of a target protein in the presence or absence of an mRNA. By comparing the ERPs for each of the various LNP or other lipid particles, one can readily determine the optimized system, e.g., the LNP or other lipid particle that has the greatest uptake in the cell.

Cells for Delivery of Lipid Particles

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like. In preferred embodiments, an active agent or therapeutic agent such as one or more nucleic acid molecules (e.g, an interfering RNA (e.g., siRNA) or mRNA) is delivered to cancer cells such as, e.g., lung cancer cells, colon cancer cells, rectal cancer cells, anal cancer cells, bile duct cancer cells, small intestine cancer cells, stomach (gastric) cancer cells, esophageal cancer cells, gallbladder cancer cells, liver cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of lipid particles such as LNP encapsulating one or more nucleic acid molecules (e.g., interfering RNA (e.g., siRNA) or mRNA) is suited for targeting cells of any cell type. The methods and compositions can be employed with cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Detection of Lipid Particles

In some embodiments, the lipid particles of the present invention (e.g., LNP) are detectable in the subject at about 1, 2, 3, 4, 5, 6, 7, 8 or more hours. In other embodiments, the lipid particles of the present invention (e.g., LNP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid, such as an interfering RNA (e.g., siRNA) sequence or mRNA sequence, detection of the target sequence of interest (e.g., by detecting expression or reduced expression of the sequence of interest), or a combination thereof.

Detection of Particles

Lipid particles of the invention such as LNP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^{3}H$, $^{25}I$, $^{3}S$, $^{14}C$, $^{32}P$, $^{33}P$, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

Detection of Nucleic Acids

Nucleic acids (e.g., interfering RNA or mRNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; The *Journal Of NIH Research,* 3:81 (1991); Kwoh et al., *Proc. Natl. Acad. Sci. USA,* 86:1173 (1989); Guatelli et al., *Proc. Natl. Acad. Sci. USA,* 87:1874 (1990); Lomell et al., *J. Clin. Chem.,* 35:1826 (1989); Landegren et al., *Science,* 241:1077 (1988); Van Brunt, *Biotechnology,* 8:291 (1990); Wu and Wallace, *Gene,* 4:560 (1989); Barringer et al., *Gene,* 89:117 (1990); and Sooknanan and Malek, *Biotechnology,* 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.,* 22:1859 1862 (1981), e.g., using an automated synthesizer, as described in Needham VanDevanter et al., *Nucleic Acids Res.,* 12:6159 (1984). Purification of polynucleotides, where necessary, is typically performed by either native acrylamide gel electrophoresis or by anion exchange HPLC as described in Pearson et al., *J. Chrom.,* 255:137 149 (1983). The sequence of the synthetic polynucleotides can be verified using the chemical degradation method of Maxam and Gilbert (1980) in Grossman and Moldave (eds.) Academic Press, New York, *Methods in Enzymology,* 65:499.

An alternative means for determining the level of transcription is in situ hybridization. In situ hybridization assays are well-known and are generally described in Angerer et al., *Methods Enzymol.,* 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

EXAMPLES

The present invention will be described in greater detail by way of specific examples. The following examples are offered for illustrative purposes and are not intended to limit the invention in any manner. Those of skill in the art will readily recognize a variety of noncritical parameters which can be changed or modified to yield essentially the same results.

Example 1 Synthesis of (4-bromobutyl)tris[(4Z)-dec-4-en-1-yloxy]silane (3)

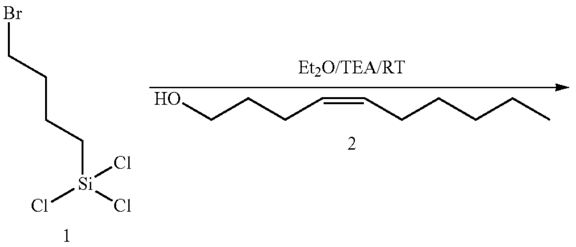

1 2

-continued

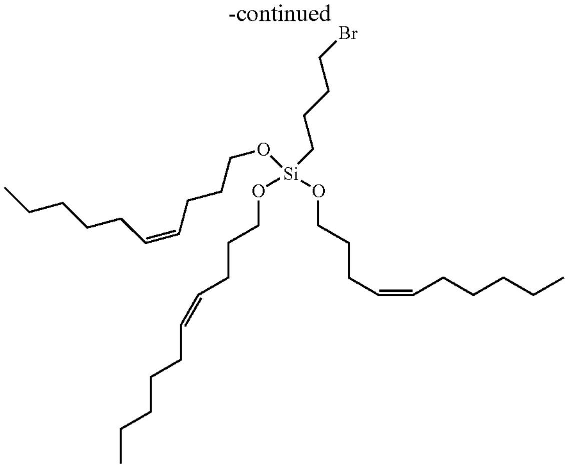

3

(4-Bromobutyl)trichlorosilane (1) (21.77 g, 80.5 mmol) was stirred in $Et_2O$ at 0° C. (4Z)-Dec-4-en-1-ol (2) (41.5 g, 265.6 mmol) and TEA (36.9 mL, 265.6 mmol) in $Et_2O$ was added dropwise with stirring. After complete addition the flask was stopped, shaken well and allowed to stand at RT O/N. The resultant precipitate was removed by filtration and the cake washed with additional $Et_2O$. The filtrate was concentrated in-vacuo and the residue purified by automated flash purification (1% EtOAc/Hex) to give (4-bromobutyl) tris[(4Z)-dec-4-en-1-yloxy]silane (36.18 g, 71.4%). $^1H$ NMR (400 MHz, $CDCl_3$) δ 5.38 (m, 6H), 3.74 (t, 6H, J=4 Hz), 2.22 (m 8H), 2-2.12 (m, 12H), 1.61 (m, 6H), 1.24-1.52 (m, 28H), 0.89 (t, 9H, J=4 Hz), J=0.64 (m, 2H).

Example 2 Synthesis of Compounds 4 and 5

4

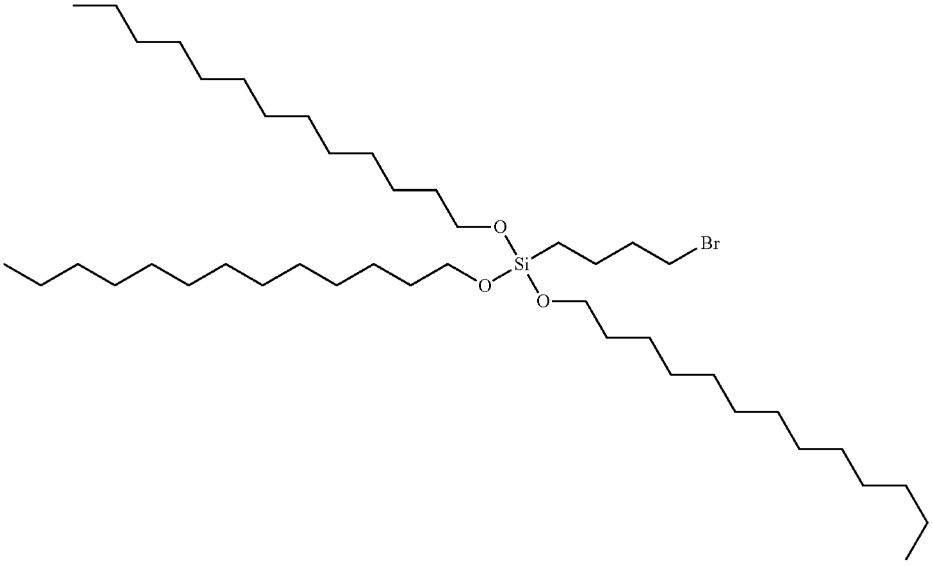

5

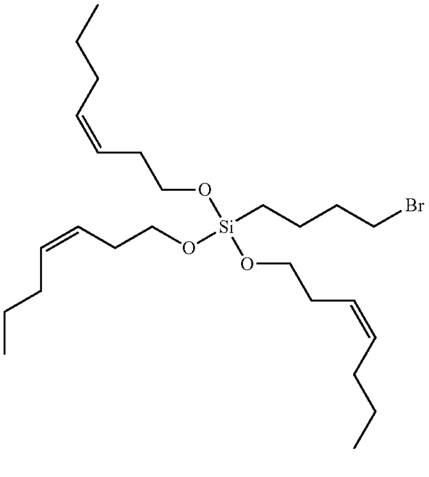

Compounds (4 and 5) were synthesized in an analogous fashion to (4-bromobutyl)tris[(4Z)-dec-4-en-1-yloxy]silane (3) using the appropriate alcohol.

Example 3 Synthesis of (4-bromobutyl)bis(((Z)-dec-4-en-1-yl)oxy)(methyl)silane (7)

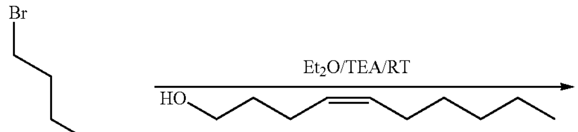

6

2

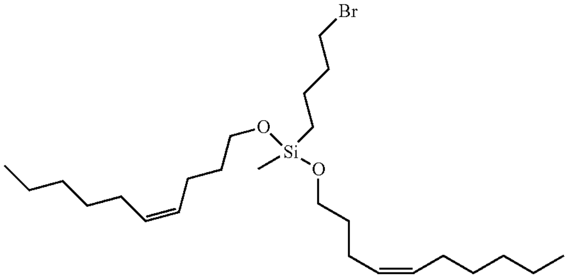

7

Compound (7) was prepared in an analogous fashion to compound (3) using (4-bromobutyl)dichloro(methyl)silane (6). Gave (9.5 g, 51%). $^1$H NMR (400 MHz, $CDCl_3$) δ 5.36 (m, 4H), 3.68 (4H, t, J=8 Hz), 3.41 (t, 2H, J=8 Hz), 1.99-2.11 (m, 8H), 1.49-1.64 (m, 6H), 1.31 (m, 12H), 0.89 (t, 6H, J=4 Hz), 0.61 (m, 2H), 0.11 (s, 3H).

Example 4 Synthesis of Compounds 8, 9, and 10

8

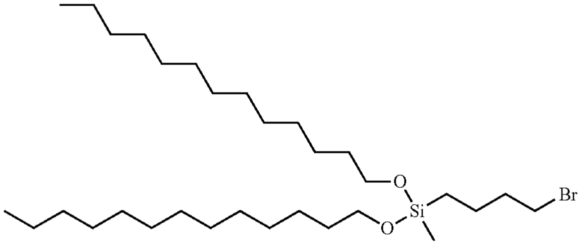

9

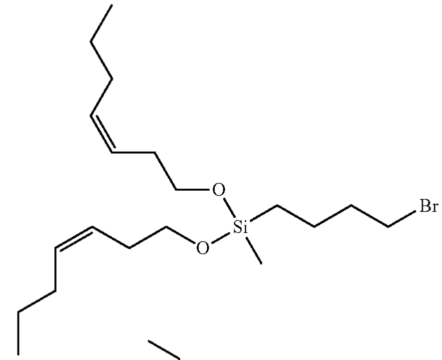

10

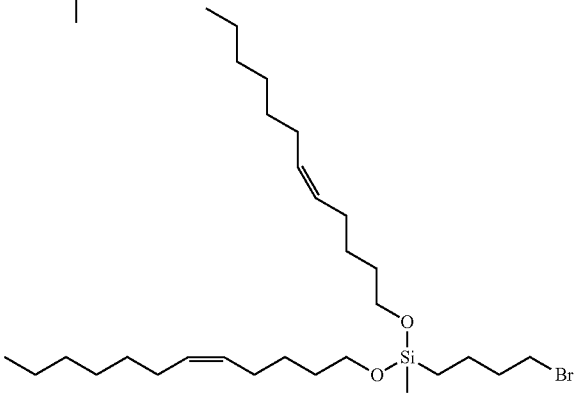

Compounds (8, 9 and 10) were synthesized in an analogous fashion to (4-bromobutyl)bis(((Z)-dec-4-en-1-yl)oxy)(methyl)silane (7) using the appropriate alcohol.

Example 5 General Synthesis of Compounds 13-43 in Table 1 are Exemplified by the Synthesis of Compound 12

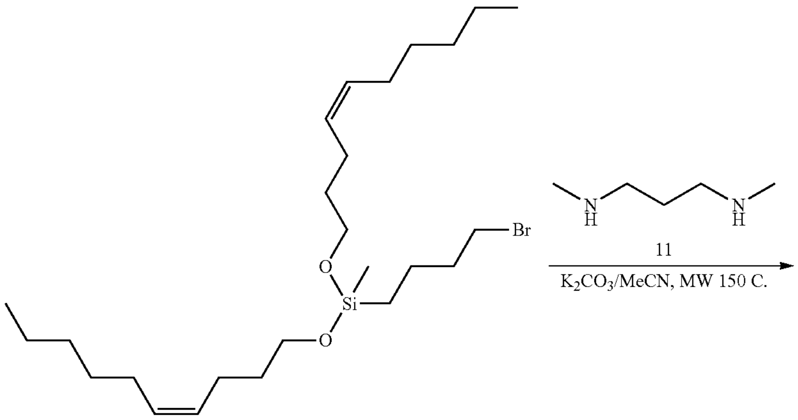

7

-continued

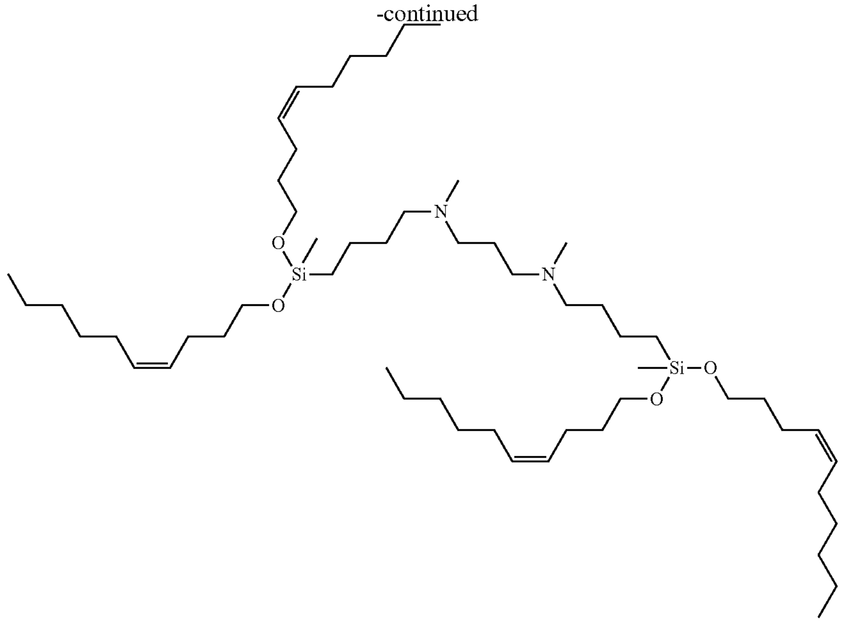

12

Synthesis of N1,N3-bis(4-(bis(((Z)-dec-4-en-1-yl)oxy)(methyl)silyl)butyl)-N1,N3-dimethylpropane-1,3-diamine (12) (4-bromobutyl)bis(((Z)-dec-4-en-1-yl)oxy)(methyl)silane (7) (0.72 g, 1.47 mmol), N1,N3-dimethylpropane-1,3-diamine (11) (50 mg, 0.49 mmol) and $K_2CO_3$ (138 mg, 1.22 mmol) were heated in a microwave at 150° C. for 25 mins. The reaction was diluted with EtOAc, washed with $H_2O$ and saturated NaCl solution, separated, dried (MgSO4) and concentrated in-vacuo. The residue was purified by automated flash chromatography (5% MeOH/DCM) to give N1,N3-bis(4-(bis(((Z)-dec-4-en-1-yl)oxy)(methyl)silyl)butyl)-N1,N3-dimethylpropane-1,3-diamine (12) (96 mg, 21.3%). $^1H$ NMR (400 MHz, $CDCl_3$) δ 5.38 (m, 8H), 3.66 (t, 8H, J=4 Hz), 2.8 (m, 2H), 2.68 (m, 2H), 2.49 (s, 6H), (1.98-2.11) (m, 18H), 1.56-1.72 (m, 30H), 0.88 (t, 12H, J=4 Hz), 0.62 (m, 4H), 0.1 (s, 6H)

Compounds (13-43) in Table 1 were synthesized using analogous synthetic methodologies using the appropriate diamine and silicon halide starting materials.

TABLE 1

| Compound | Structure | Formulation | Dose (mg/kg) | Percent knock-down |
|---|---|---|---|---|
| 13 | 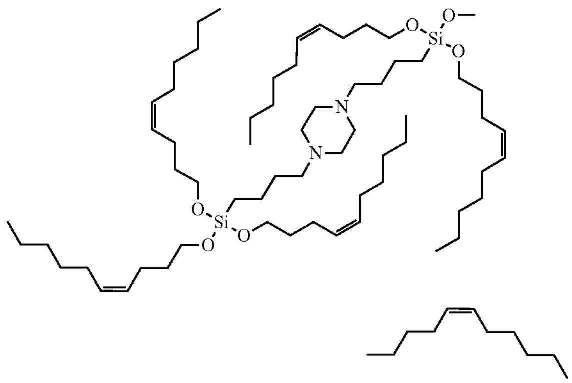 [SMILES: CCCCC/C=C\CCCO[Si](CCCCN1CCN(CCCC[Si](OCCC/C=C\CCCCC)(OCCC/C=C\CCCCC)OCCC/C=C\CCCCC)CC1)(OC)OCCC/C=C\CCCCC ; CCCC/C=C\CCCCC] | 1.1:55 (DOPE) | DNF | N/A |

TABLE 1-continued
| Compound | Structure | Formulation | Dose (mg/kg) | Percent knock-down |
|---|---|---|---|---|
| 14 | 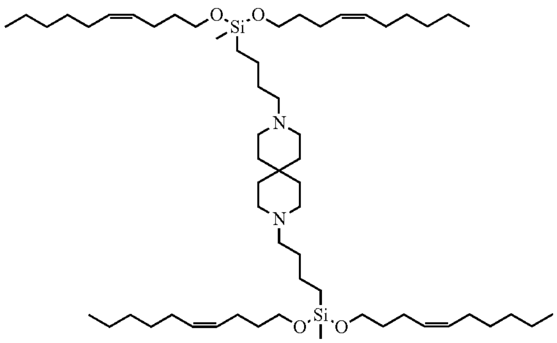 [SMILES: CCCCC/C=C\CCCO[Si](C)(CCCCN1CCC2(CC1)CCN(CCCC[Si](C)(OCCC/C=C\CCCCC)OCCC/C=C\CCCCC)CC2)OCCC/C=C\CCCCC] | 1.1:55 (DOPE) | 0.025 | 18% |
| 15 | 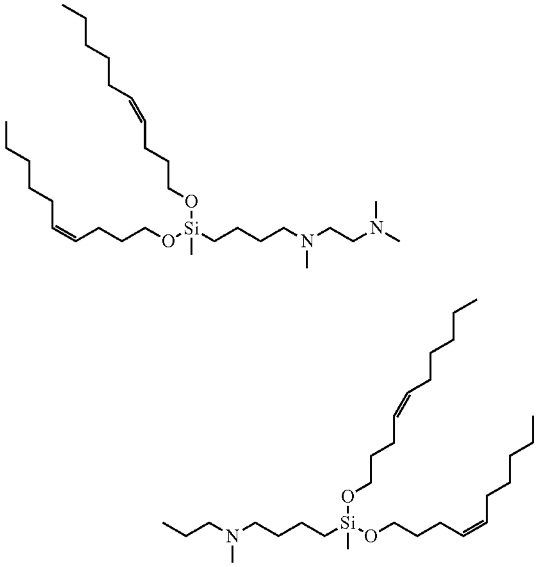 | 1.1:55 (DOPE) | 0.025 | 18% |

TABLE 1-continued
| Compound | Structure | Formulation | Dose (mg/kg) | Percent knockdown |
|---|---|---|---|---|
| 16 | 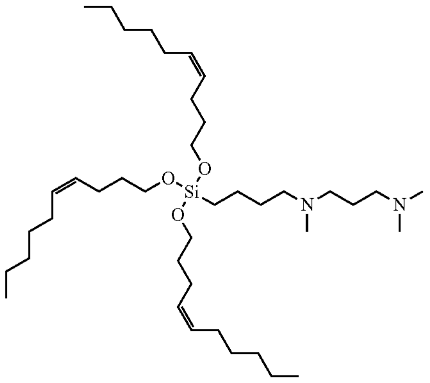 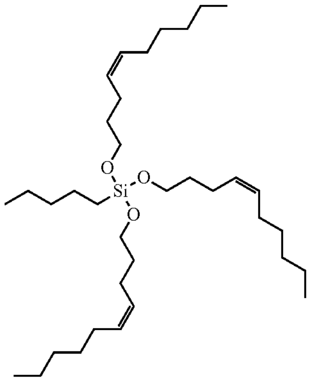 | 1.1:55 (DOPE) | 0.025 | 23% |
| 17 | 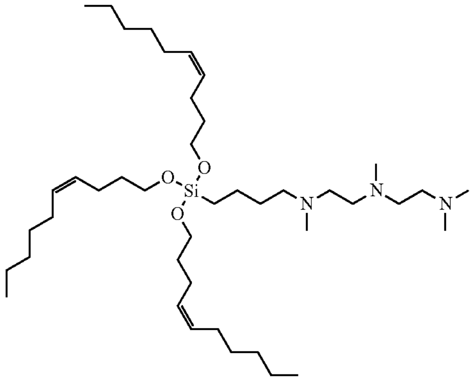 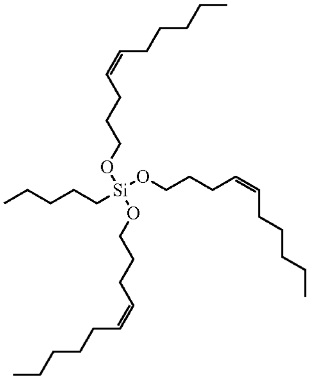 | 1.1:55 (DOPE) | 0.025 | 37% |

TABLE 1-continued
| Compound | Structure | Formulation | Dose (mg/kg) | Percent knockdown |
|---|---|---|---|---|
| 18 | 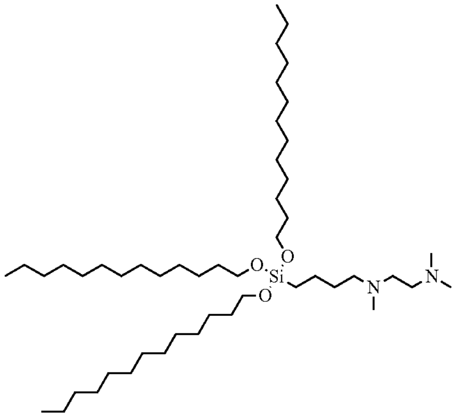 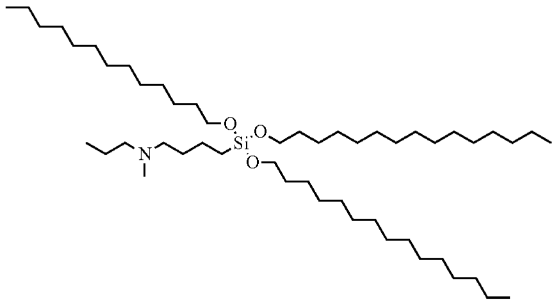 | 1.1:55 (DSPC) | DNF | N/A |
| 19 | 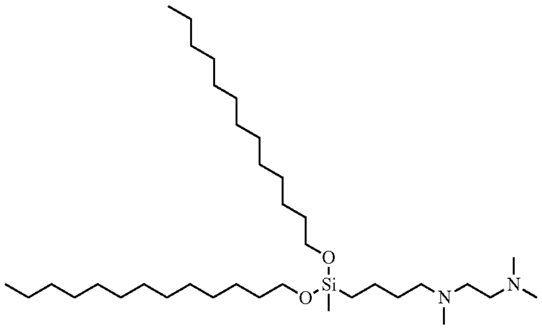 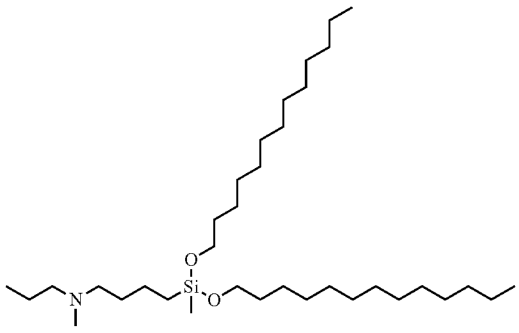 | 1.1:55 (DSPC) | DNF | N/A |

TABLE 1-continued
| Compound | Structure | Formulation | Dose (mg/kg) | Percent knockdown |
|---|---|---|---|---|
| 20 | 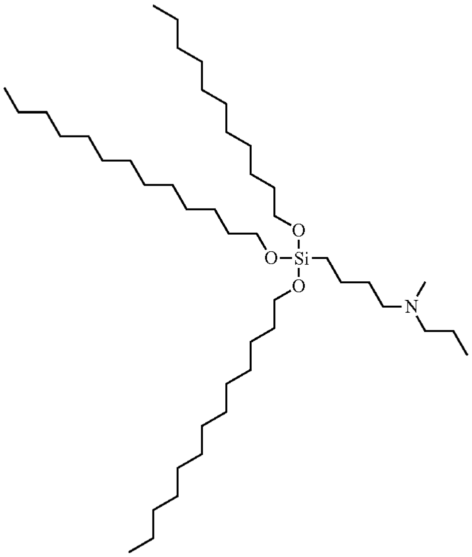 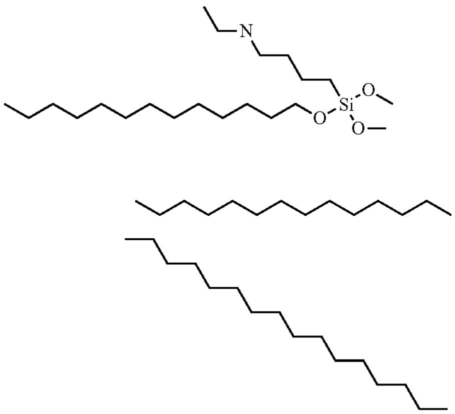 | N/A | N/A | N/A |

TABLE 1-continued
| Compound | Structure | Formulation | Dose (mg/kg) | Percent knock-down |
|---|---|---|---|---|
| 21 | 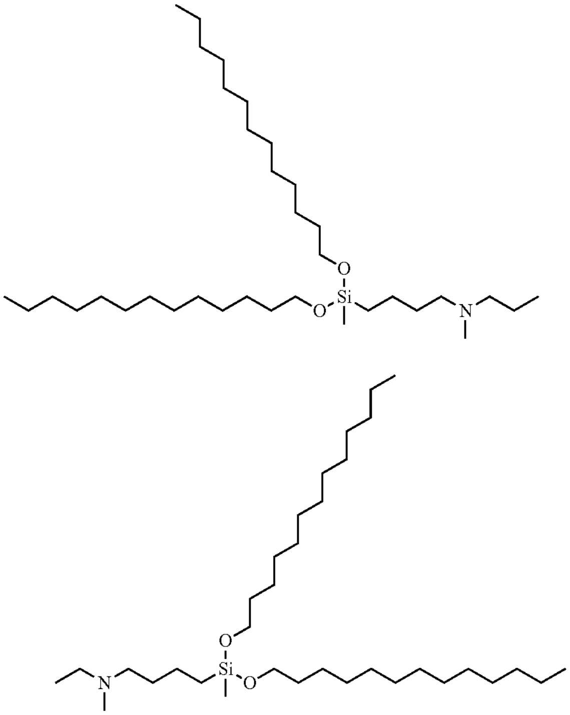 | 1.1:55 (DSPC) | DNF | N/A |
| 22 | 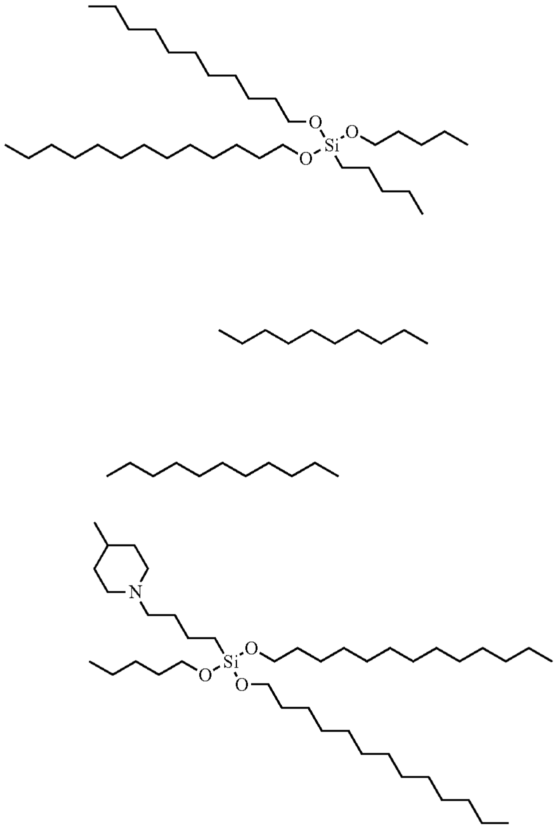 | N/A | N/A | N/A |

TABLE 1-continued
| Compound | Structure | Formulation | Dose (mg/kg) | Percent knockdown |
| --- | --- | --- | --- | --- |
| 23 | 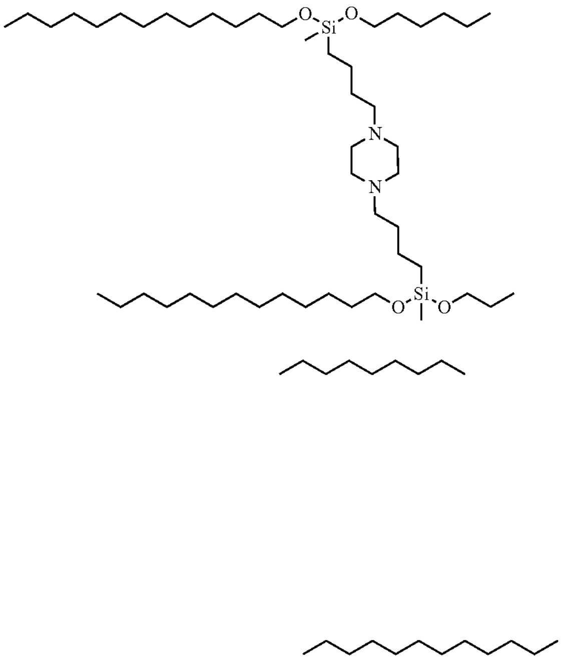 | N/A | N/A | N/A |
| 24 | 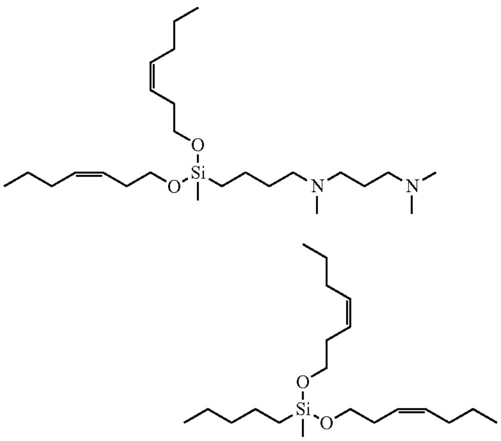 | 1.1:55 (DSPC) | 0.025 | 14% |

TABLE 1-continued
| Compound | Structure | Formulation | Dose (mg/kg) | Percent knock-down |
| --- | --- | --- | --- | --- |
| 25 | 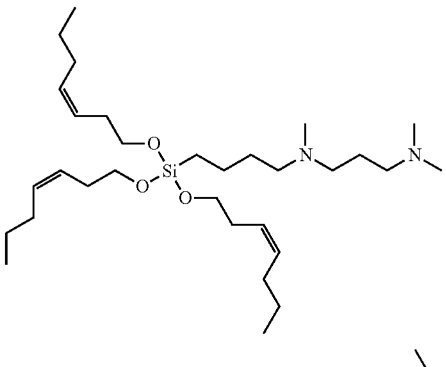 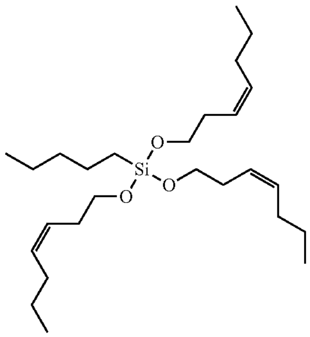 | 1.1:55 (DSPC) | 0.025 | 79% |
| 26 | 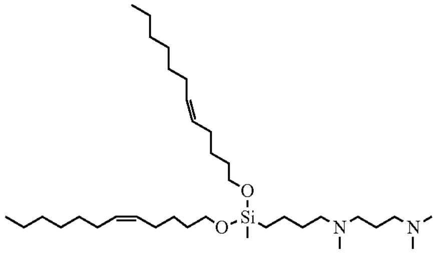 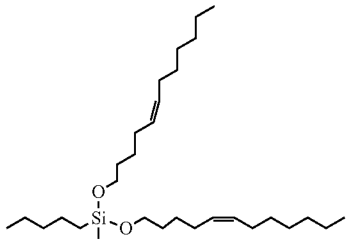 | 1.1:55 (DSPC) | 0.025 | 6% |

TABLE 1-continued
| Compound | Structure | Formulation | Dose (mg/kg) | Percent knockdown |
| --- | --- | --- | --- | --- |
| 27 | 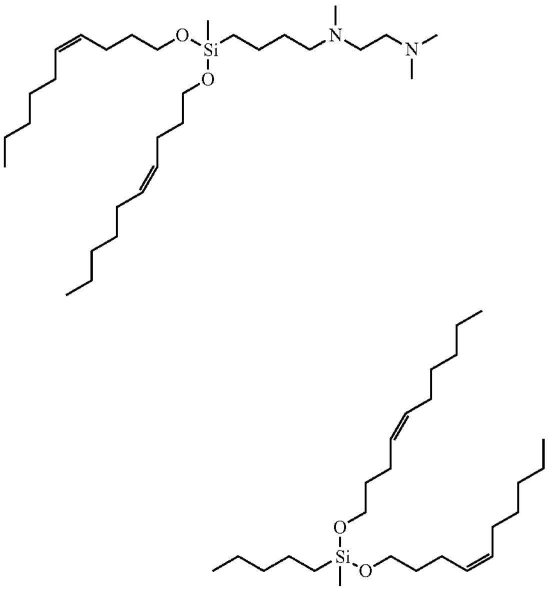 | 1.1:55 (DSPC) | 0.025 | 20% |
| 28 | 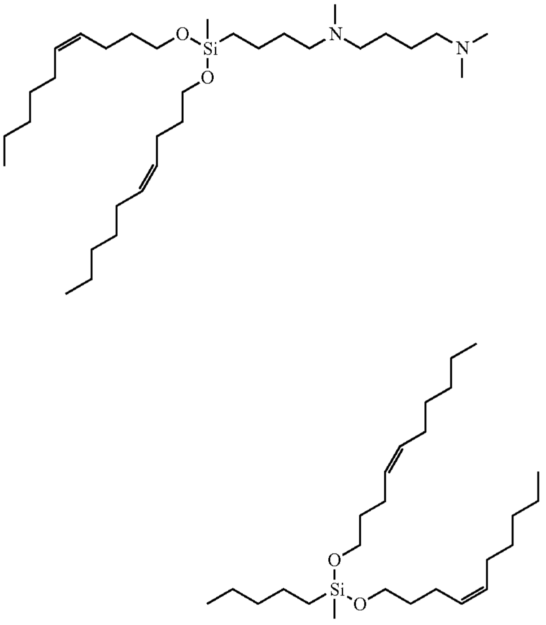 | 1.1:55 (DSPC) | 0.025 | 20% |

TABLE 1-continued
| Compound | Structure | Formulation | Dose (mg/kg) | Percent knockdown |
| --- | --- | --- | --- | --- |
| 29 | 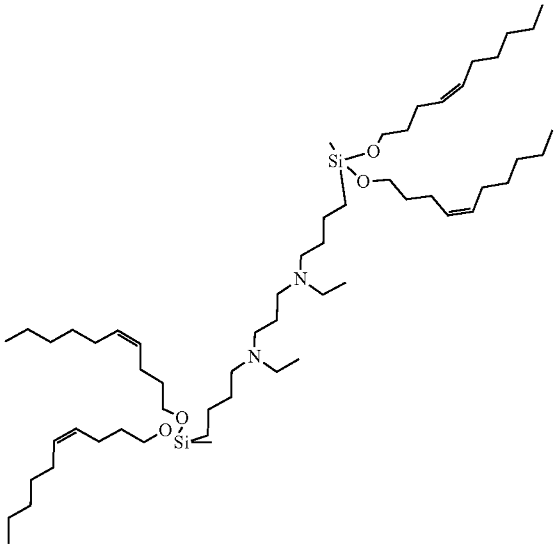 [SMILES: CCCCC/C=C\CCCO[Si](C)(CCCCN(CC)CCCN(CC)CCCC[Si](C)(OCCC/C=C\CCCCC)OCCC/C=C\CCCCC)OCCC/C=C\CCCCC] | 1.1:55 (DSPC) | 0.025 | 29% |
| 30 | 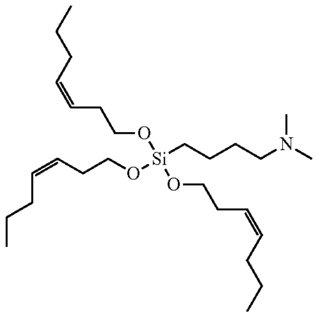 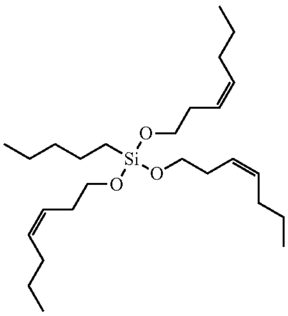 | 1.5:50 (DSPC) | 0.025 | 5% |

TABLE 1-continued
| Compound | Structure | Formulation | Dose (mg/kg) | Percent knock-down |
|---|---|---|---|---|
| 31 | 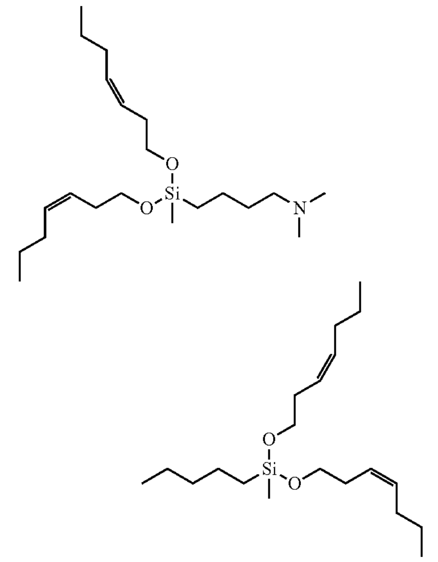 | 1.5:50 (DSPC) | 0.025 | 0% |
| 32 | 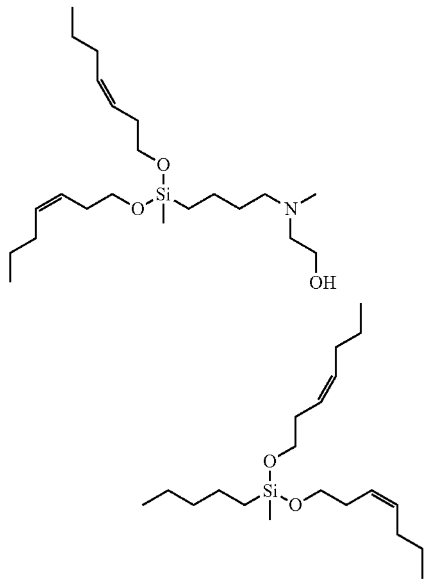 [SMILES: CCC/C=C\CCO[Si](C)(CCCCN(C)CCO)OCC/C=C\CCC ; CCC/C=C\CCO[Si](C)(CCCCC)OCC/C=C\CCC] | 1.5:50 (DSPC) | 0.025 | 2% |
| 33 | 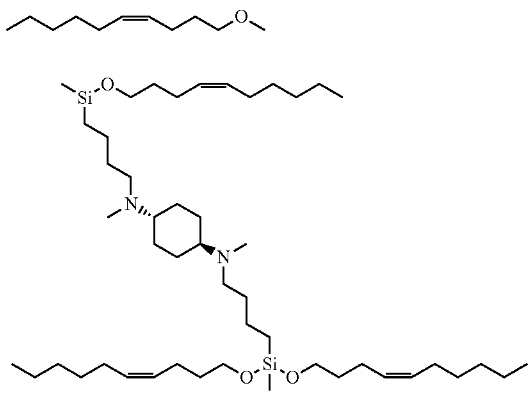 | 1.5:50 (DSPC) | 0.025 | 75% |

TABLE 1-continued
| Compound | Structure | Formulation | Dose (mg/kg) | Percent knockdown |
|---|---|---|---|---|
| 34 | 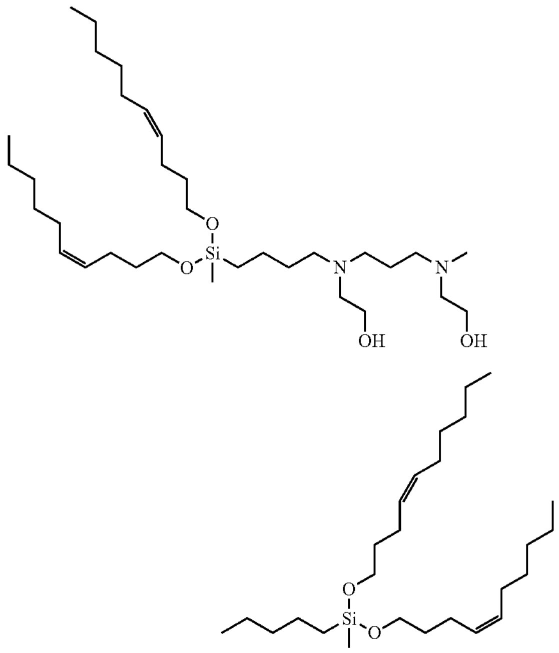 | 1.5:50 (DSPC) | 0.025 | 29% |
| 35 | 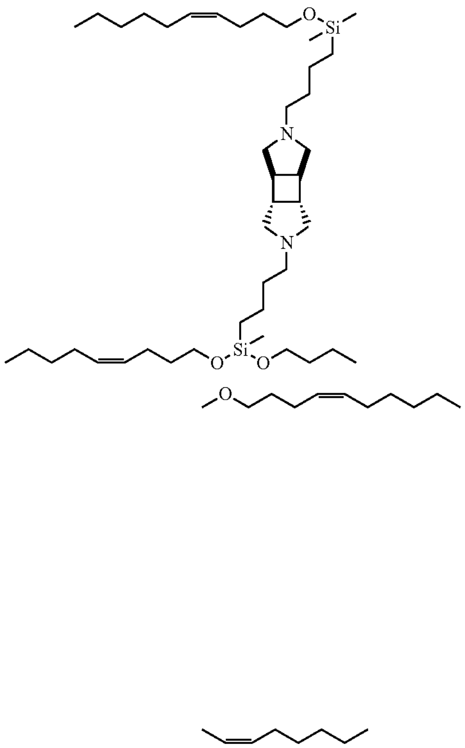 | 1.5:50 (DSPC) | 0.025 | 3% |

TABLE 1-continued
| Compound | Structure | Formulation | Dose (mg/kg) | Percent knockdown |
|---|---|---|---|---|
| 36 | 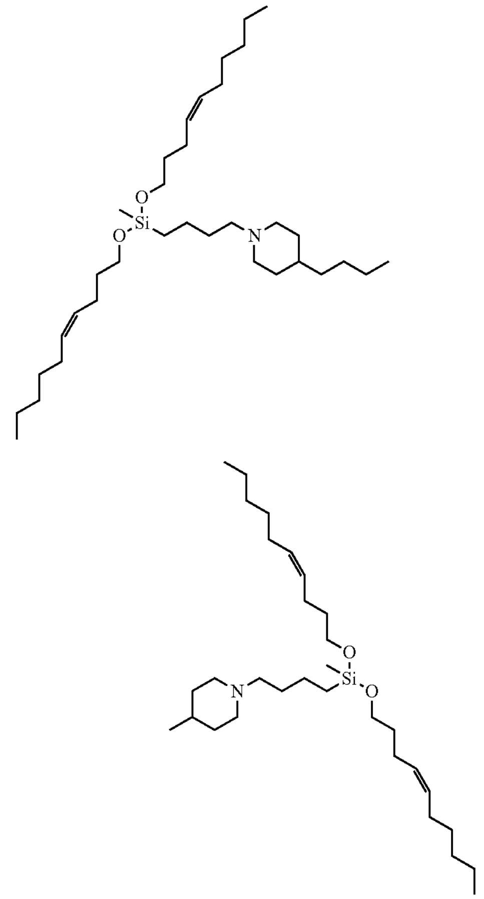 | 1.5:50 (DSPC) | DNF | N/A |
| 37 | 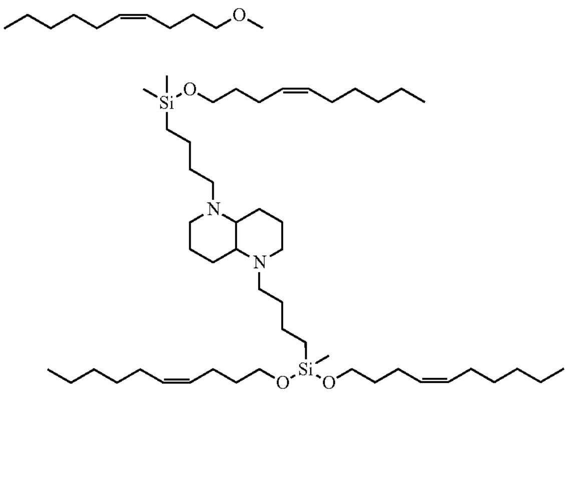 [SMILES: CCCCC/C=C\CCCOC ; CCCCC/C=C\CCCO[Si](C)(C)CCCCN1CCCC2C1CCCN2CCCC[Si](C)(OCCC/C=C\CCCCC)OCCC/C=C\CCCCC] | 1.5:50 (DSPC) | 0.025 | 7% |

TABLE 1-continued
| Compound | Structure | Formulation | Dose (mg/kg) | Percent knockdown |
|---|---|---|---|---|
| 38 | 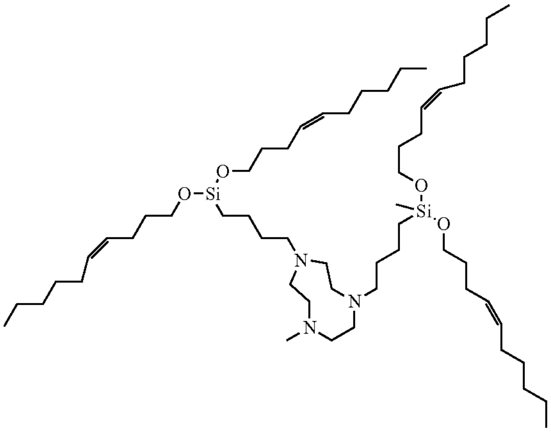 | 1.5:50 (DSPC) | 0.025 | 1% |
| 39 | 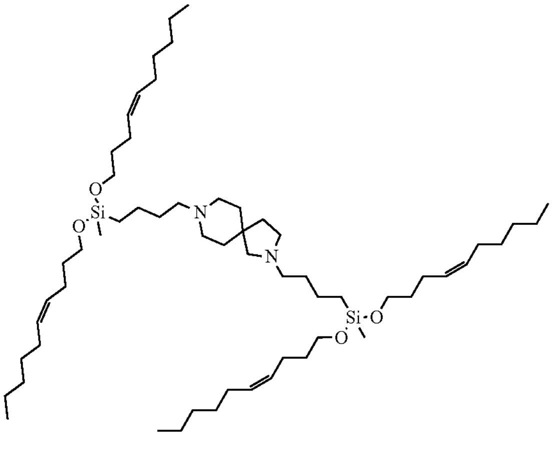 [SMILES: CCCCC/C=C\CCCO[Si](C)(CCCCN1CCC2(CC1)CCN(CCCC[Si](C)(OCCC/C=C\CCCCC)OCCC/C=C\CCCCC)C2)OCCC/C=C\CCCCC] | 1.5:50 (DSPC) | 0.025 | 81% |
| 40 | 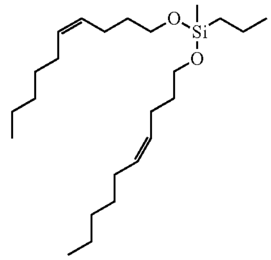 | 1.5:50 (DSPC) | DNF | N/A |
| | 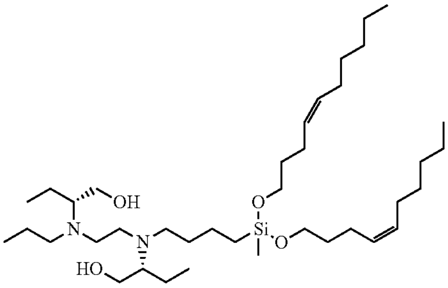 | | | |

TABLE 1-continued
| Compound | Structure | Formulation | Dose (mg/kg) | Percent knock-down |
|---|---|---|---|---|
| 41 | 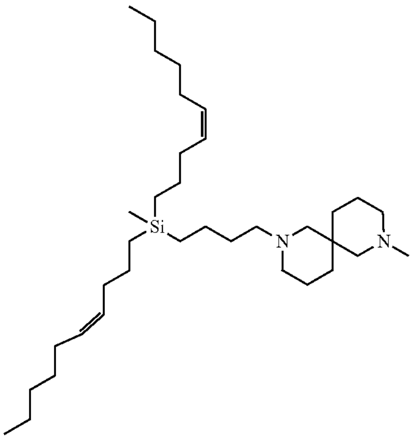 | 1.5:50 (DSPC) | 0.025 | 0 |
| | 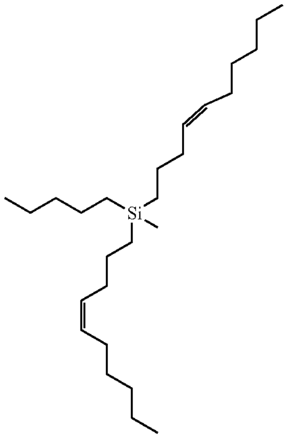 | | | |
| 42 | | 1.5:50 (DSPC) | 0.025 | 28% |
| | 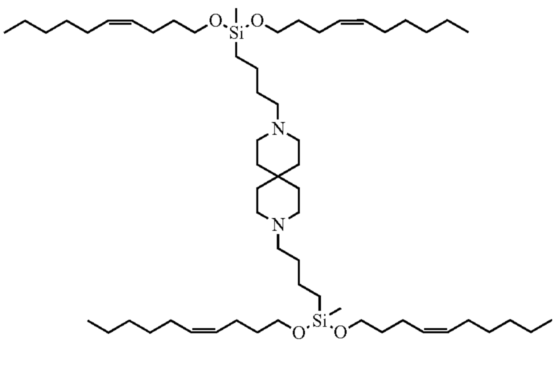 [SMILES: CCCCC/C=C\CCCO[Si](C)(CCCCN1CCC2(CC1)CCN(CCCC[Si](C)(OCCC/C=C\CCCCC)OCCC/C=C\CCCCC)CC2)OCCC/C=C\CCCCC] | | | |

TABLE 1-continued

| Compound | Structure | Formulation | Dose (mg/kg) | Percent knock-down |
|---|---|---|---|---|
| 43 | 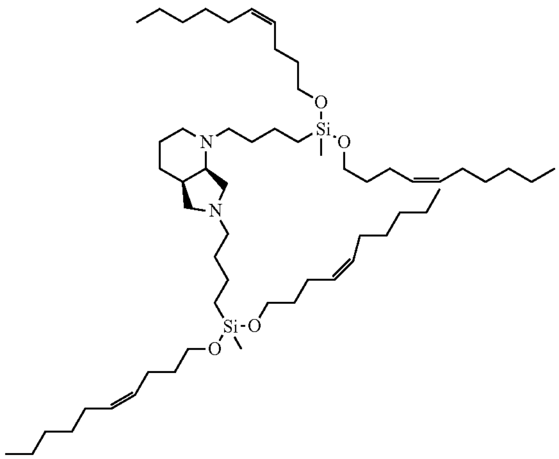 [SMILES: CCCCC/C=C\CCCO[Si](C)(CCCCN1C[C@H]2CCCN(CCCC[Si](C)(OCCC/C=C\CCCCC)OCCC/C=C\CCCCC)[C@H]2C1)OCCC/C=C\CCCCC] | 1.5:50 (DSPC) | 0.025 | 0 |

Accordingly, certain embodiments of the invention are directed to any one of compounds depicted herein, including any one of compounds 12-43, and to salts thereof.

Example 6

General Formulation Procedure

The lipid solution contained 4 components: a PEG-conjugated lipid, an ionizable lipid (e.g., a silicon lipid), cholesterol, and a phospholipid (e.g., DSPC). Lipid stocks were prepared using the lipid identities and molar ratios as described. The siRNA was diluted in 100 mM acetate, pH 4 buffer to prepare lipid nanoparticles (LNP) at a total lipid to siRNA weight ratio of approximately 10:1 to 20:1. Equal volumes of the lipid and nucleic acid solutions were blended at a flow rate of 400 mL/min through a T-connector, and diluted into PBS, pH 7.4. The ethanol was then removed and the external buffer replaced with Tris/NaCl buffer by dialysis. Following dialysis, the formulations were concentrated using VivaSpin concentrator units (MWCO 100,000) and filtered through a 0.2 μm pore sterile filter. Nucleic acid concentration was determined by the RiboGreen assay. Particle size and polydispersity were determined using a Malvern Nano Series Zetasizer.

Activity Assessment

Generally, the LNP formulations were injected intravenously at 0.025 mg/kg to female Balb/C mice (5-8 weeks old) to measure activity of the HSC-LNP. Just prior to injection, the siRNA LNP stocks were filtered and diluted down to the required dosing concentration. At 48h post-dose (terminal timepoint), the animals were euthanized with a lethal dose of ketamine/xylazine. Half the left lateral lobe of the liver was collected into 1.5 mL RNALater and stored at 2-8° C. overnight. The next day, an approximately 20-25 mg piece of liver was homogenized and the liver lysate used in a QuantiGene Assay, testing for relative levels of mouse target mRNA and GAPDH expression. Data from each animal was normalized to the liver weight used in the assay, and then relative to the GAPDH signal; data is reported as the average % knock-down of each group (where the PBS control group is 100% gene expression, 0% knock-down).

Tolerability Assessment

Generally, the LNP formulations were injected intravenously at ~0.03 to 3 mg/kg to female Balb/C mice (5-8 weeks old) to assess tolerability of the HSC-LNP. Just prior to injection, the siRNA LNP stocks were filtered and diluted down to the required dosing concentration. At 2h post-treatment, blood was collected via tail nicks and processed to plasma (for cytokine analysis by ELISA). At the terminal timepoint (24 h post-dose), blood was collected by cardiac puncture (target ≥800 μL) and sent to IDEXX for CRES 15 panel analysis (CBC/Diff & Clin Chem analysis).

Briefly, blood (~300 uL) was collected into EDTA microtainer tubes, inverted 10× to mix the K2EDTA whole blood sample, and immediately stored at 4° C. to await same-day shipment to for hematology analysis. The remaining blood volume (~500 uL) was collected into serum separator tubes and inverted 5× to mix the SST sample, then allowed to clot for 1-1.5h at room temp. The blood samples were centrifuged, and serum was collected for clinical chemistry analysis.

The following siRNA sequences were used, 5' to 3':

```
RELN:
S: GGucucAAGccAcucGuuudTsdT (SEQ ID NO: 1)

AS: AAACGAGUGGCUUGAGACCdTsdT (SEQ ID NO: 2)

HSP47:
S: GAgACACAUGGgUGCuAUUGU (SEQ ID NO: 3)

AS: AAUAGCACCCAUgUgUCuCAG (SEQ ID NO: 4)
Legend: Upper case: unmodified nucleotide
Lower case: 2'-OMe modification
s: PS (phosphorothioate linkage)
```

The following compounds were used in the experiments.

Compound (100)

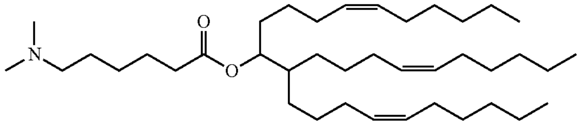

-continued

Compound (101)

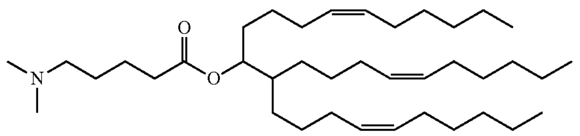

The following compound (12) was used as the representative compound of the invention in the experiments described herein and in the Figures.

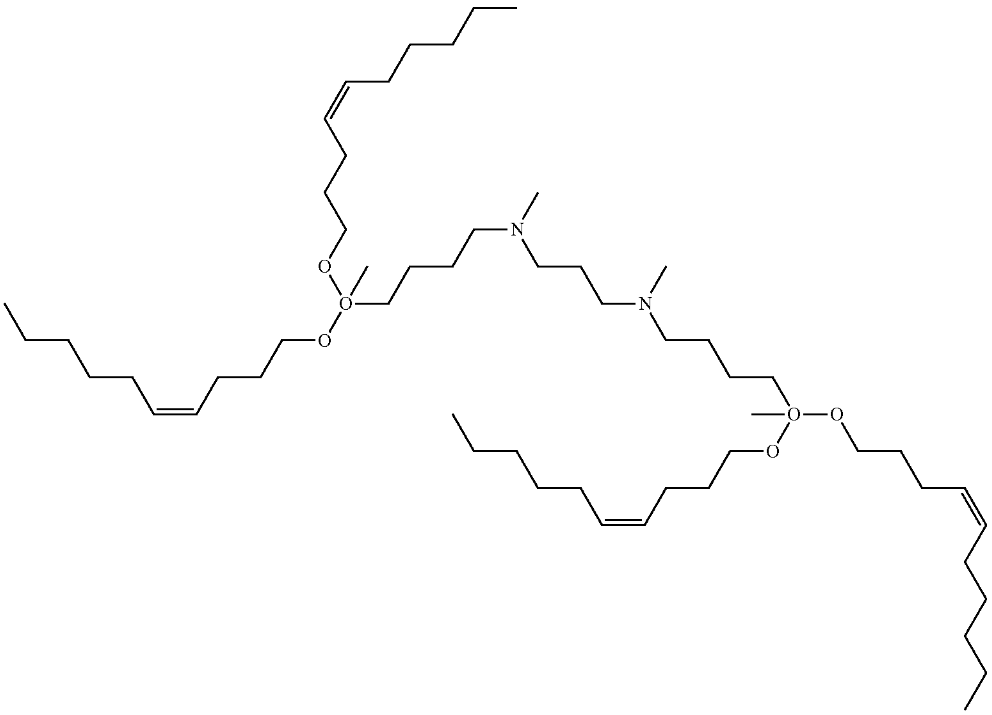

As depicted in FIG. 1, an LNP with a representative compound of the invention has equivalent potency to a benchmark, but at 4-times lower dose (0.025 mg/kg instead of 0.1 mg/kg).

Figure 2:
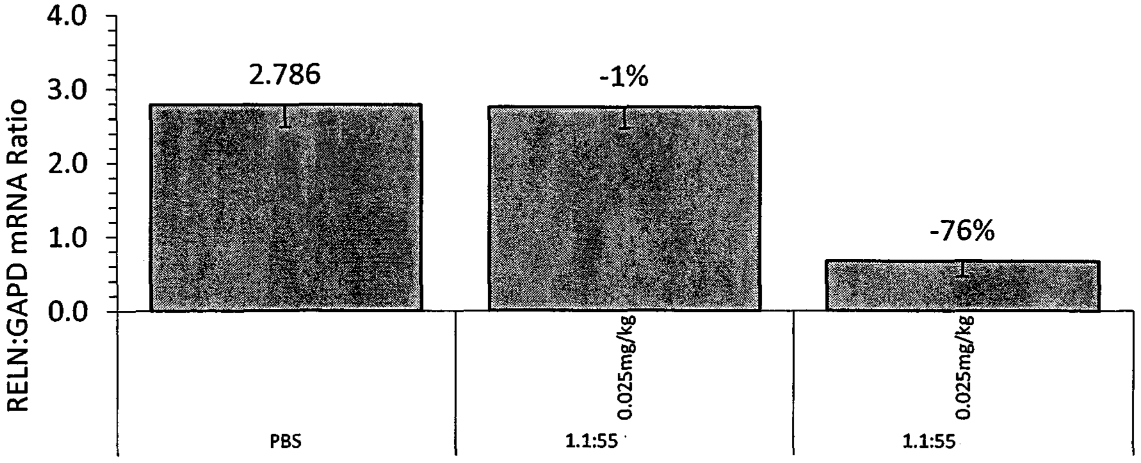
FIG. 2 depicts reelin mRNA knock-down 48 hours following IV administration of the LNP formulations in Balb/C Mice (n=4). An LNP with a representative compound of the invention (presented in column 3) has high specificity for HSCs, whereas an LNP with a benchmark compound (101; presented in column 2) designed for delivery to hepatocytes demonstrates no knock-down in HSCs. This comparative data demonstrates that lipids of the invention possess the desired quality of enabling LNP-delivery of therapeutic agents to HSCs.
Figure 3:
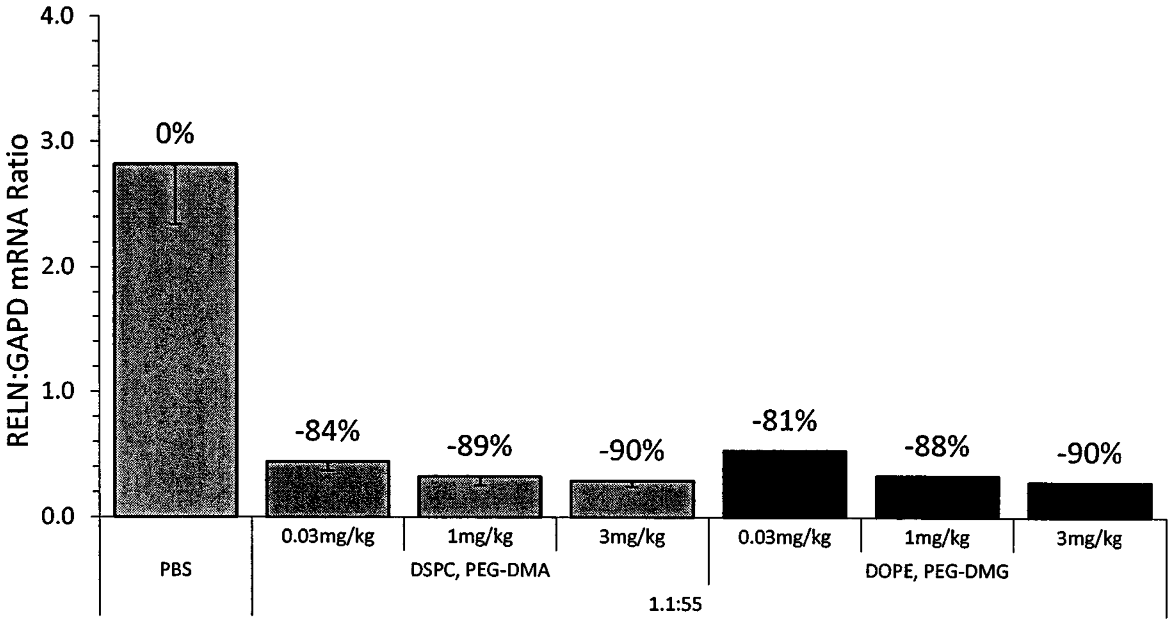
FIG. 3 depicts reelin mRNA knock-down 24 hours following IV administration of the LNP formulations in Balb/C Mice (n=4). LNP with a representative compound of the invention demonstrate that at about 0.03 mg/kg, maximum knock-down in HSCs is achieved.
Figure 4:
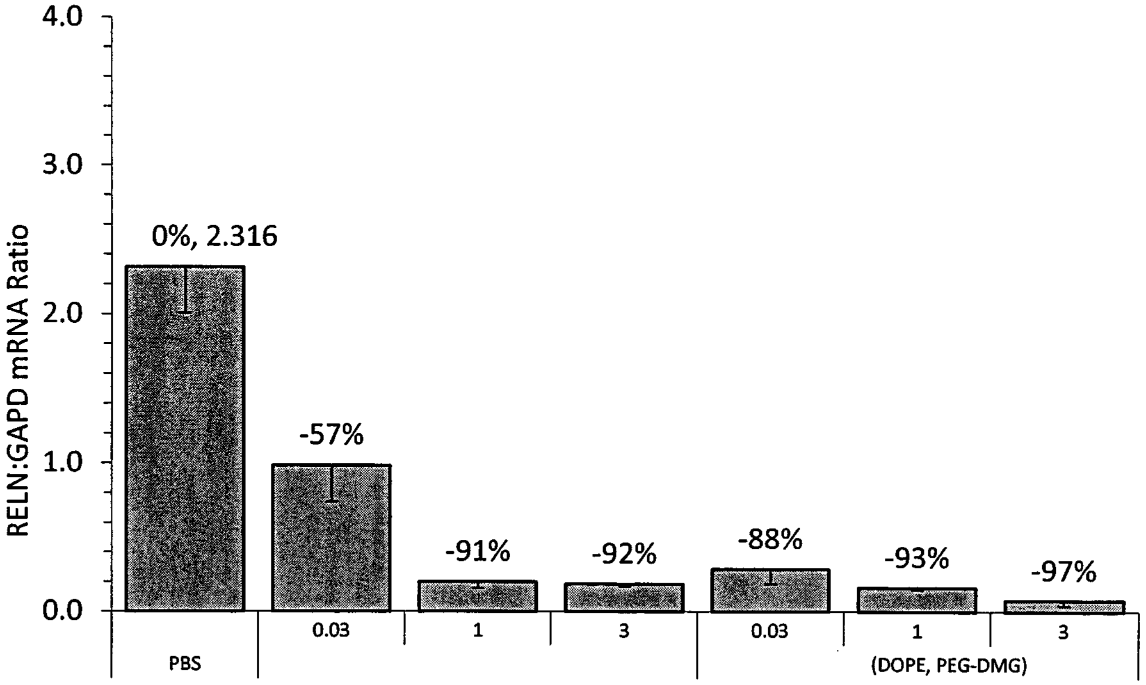
FIG. 4 depicts reelin mRNA knock-down 24 hours following IV administration of the LNP formulations in Balb/C Mice (n=4). A benchmark LNP (with compound 100; presented in columns 2-4) requires higher doses (~1 mg/kg) to achieve equivalent knock-down to a representative lipid of the invention (presented in columns 5-7) (0.03 mg/kg).

FIG. 2 demonstrates that an LNP with a representative compound of the invention has high specificity for HSCs, whereas an LNP with a comparison lipid designed for delivery to hepatocytes demonstrates no knock-down in HSCs. This comparative data demonstrates that lipids of the invention possess the desired quality of enabling LNP-delivery of therapeutic agents to HSCs. LNP with a representative compound of the invention demonstrate that at about 0.03 mg/kg, maximum knock-down in HSCs is achieved (FIG. 3). Further, an LNP with a comparison lipid designed for delivery to hepatocytes requires higher doses (~1 mg/kg) to achieve equivalent knock-down to a representative lipid of the invention. (0.03 mg/kg). (FIG. 4).

Figure 5A:
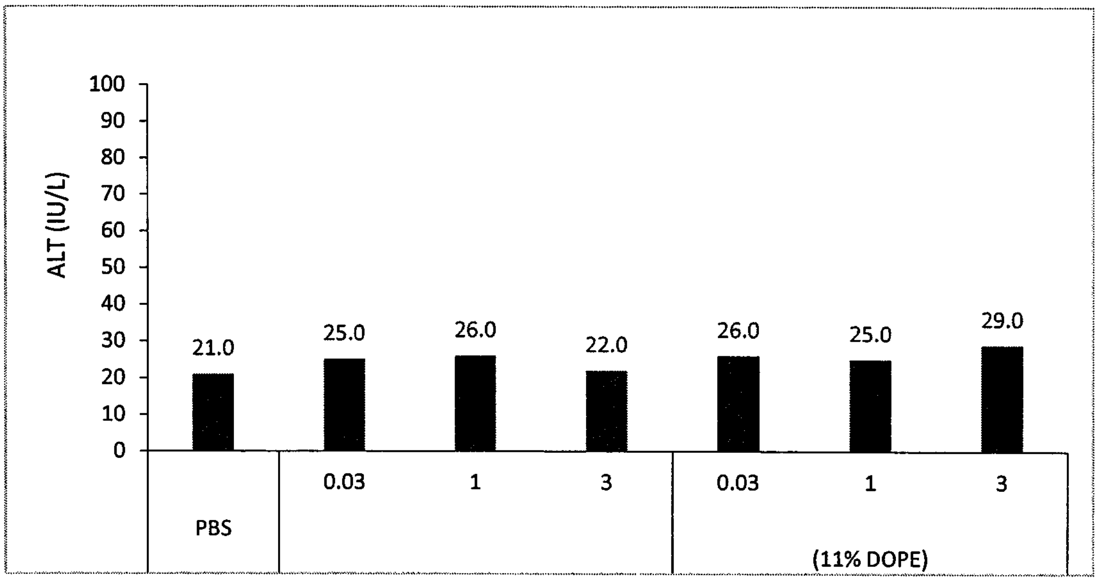
FIGS. 5A-5B demonstrate that LNP formulated with a representative lipid of the invention (presented in columns 5-7) demonstrate tolerability as no significant increases in liver enzyme levels over a dose range, up to 3 mg/kg in this study, were evident. LNP with compound 100 are also included as the first set of data in FIG. 5A (presented in columns 2-4).
Figure 5B:
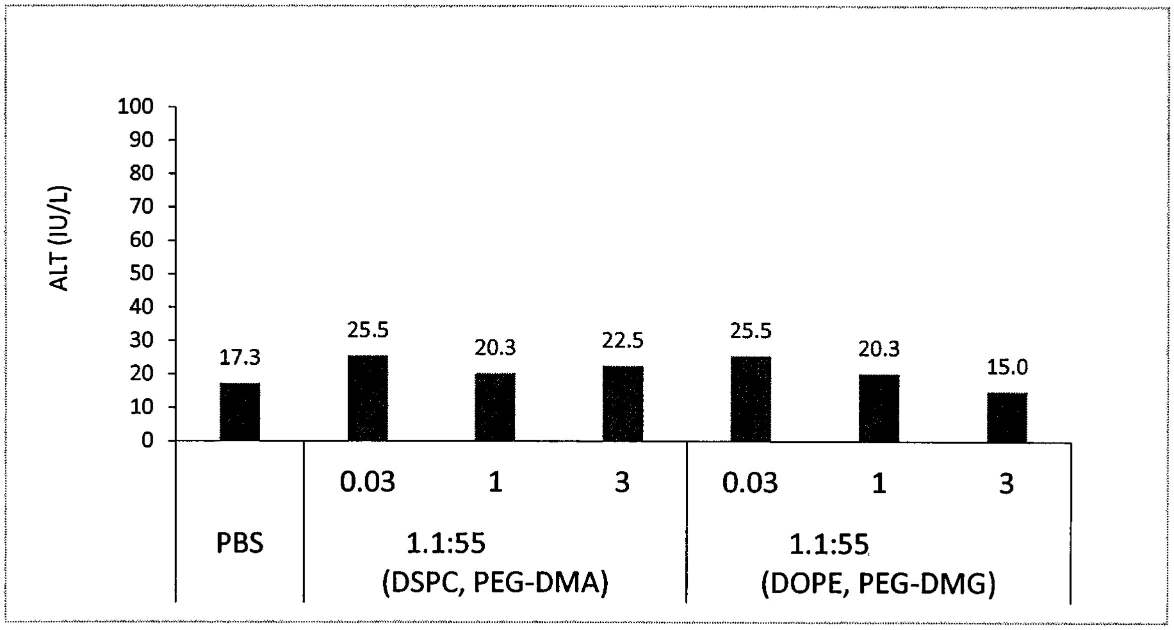

Further, LNP formulated with a representative lipid of the invention demonstrate tolerability as no significant increases in liver enzyme levels over a dose range, up to 3 mg/kg in this study, were evident (FIGS. 5A and 5B).

Figure 6:
FIG. 6 demonstrates that LNP formulated with a representative lipid of the invention and with minimally modified siRNA show good duration of action (presented in the final columns 7-11). LNP with compound 100 are also included as the first set of data in columns 2-6 in FIG. 6.

LNP formulated with a representative lipid of the invention, and with minimally modified siRNA, show good duration of action (FIG. 6).

Figure 7:
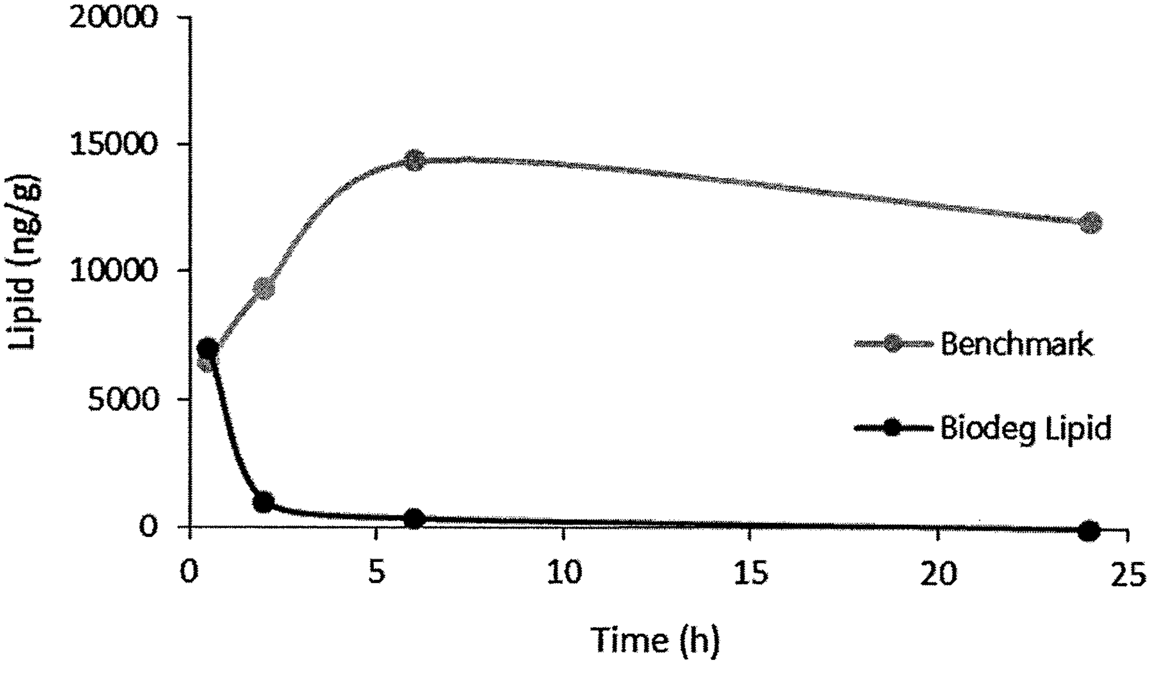
FIG. 7 demonstrates that LNP formulated with a representative lipid of the invention exhibit biodegradable functionality, and the LNP is cleared rapidly from mouse liver.

Further, LNP formulated with a representative lipid of the invention exhibit biodegradable functionality, as the LNP is cleared rapidly from mouse liver (FIG. 7).

Table 1 provides additional data regarding various lipids of the invention.

In summary, as demonstrated by the results presented herein, the lipids described herein exhibit several qualities important for delivering therapeutics to hepatic stellate cells that can be used, e.g., for the treatment of liver fibrosis, including being able to deliver therapeutics to HSC, being well tolerated, and being functionally biodegradable.

What is claimed is:

1. A compound of formula (I):

(I)

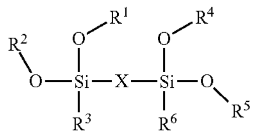

wherein:

$R^1$ is a $C_7$-$C_{30}$ hydrocarbyl;

$R^2$ is a $C_2$-$C_{30}$ hydrocarbyl;

$R^3$ is $C_1$-$C_4$ alkyl or —O—$C_2$-$C_{30}$ hydrocarbyl;

$R^4$ is a $C_2$-$C_{30}$ hydrocarbyl;

$R^5$ is a $C_2$-$C_{30}$ hydrocarbyl;

$R^6$ is $C_1$-$C_4$ alkyl or —O—$C_2$-$C_{30}$ hydrocarbyl; and

X is

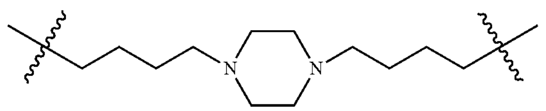

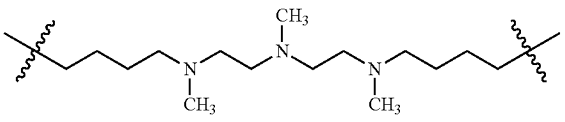

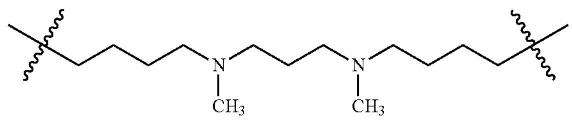

-continued

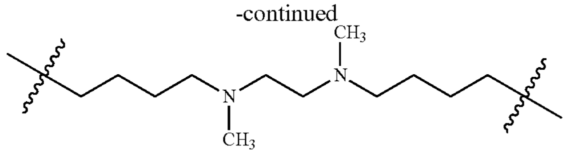

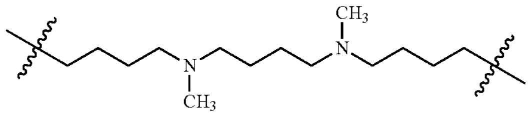

, or

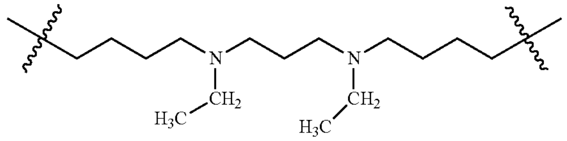

2. The compound of claim 1, wherein $R^1$ is ($C_7$-$C_{20}$)alkyl, ($C_7$-$C_{20}$)alkenyl, or ($C_7$-$C_{20}$)alkynyl.

3. The compound of claim 1, wherein $R^1$ is ($C_7$-$C_{15}$) alkenyl, having only one double bond.

4. The compound of claim 1, wherein $R^2$ is ($C_2$-$C_{20}$)alkyl, ($C_2$-$C_{20}$)alkenyl, or ($C_2$-$C_{20}$)alkynyl.

5. The compound of claim 1, wherein $R^2$ is a ($C_7$-$C_{15}$) alkenyl, having only one double bond.

6. The compound of claim 1, wherein $R^3$ is methyl.

7. The compound of claim 1, wherein $R^4$ is ($C_2$-$C_{20}$)alkyl, ($C_2$-$C_{20}$)alkenyl, or ($C_2$-$C_{20}$)alkynyl.

8. The compound of claim 1, wherein $R^4$ is ($C_7$-$C_{15}$) alkenyl, having only one double bond.

9. The compound of claim 1, wherein $R^5$ is ($C_2$-$C_{20}$)alkyl, ($C_2$-$C_{20}$)alkenyl, or ($C_2$-$C_{20}$)alkynyl.

10. The compound of claim 1, wherein $R^5$ is a ($C_7$-$C_{15}$) alkenyl, having only one double bond.

11. The compound of claim 1, wherein $R^6$ is methyl.

12. A compound selected from the group consisting of:
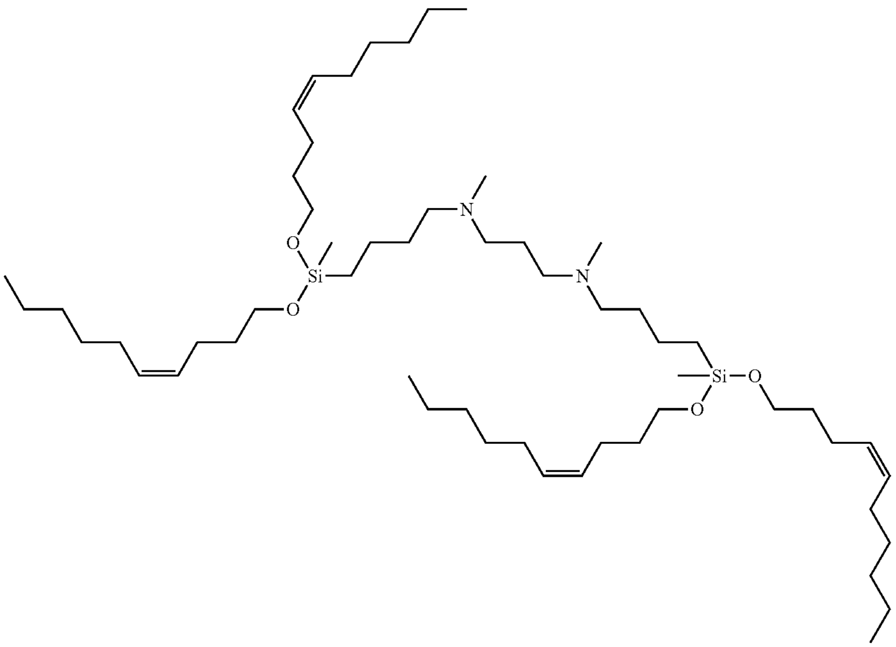
,
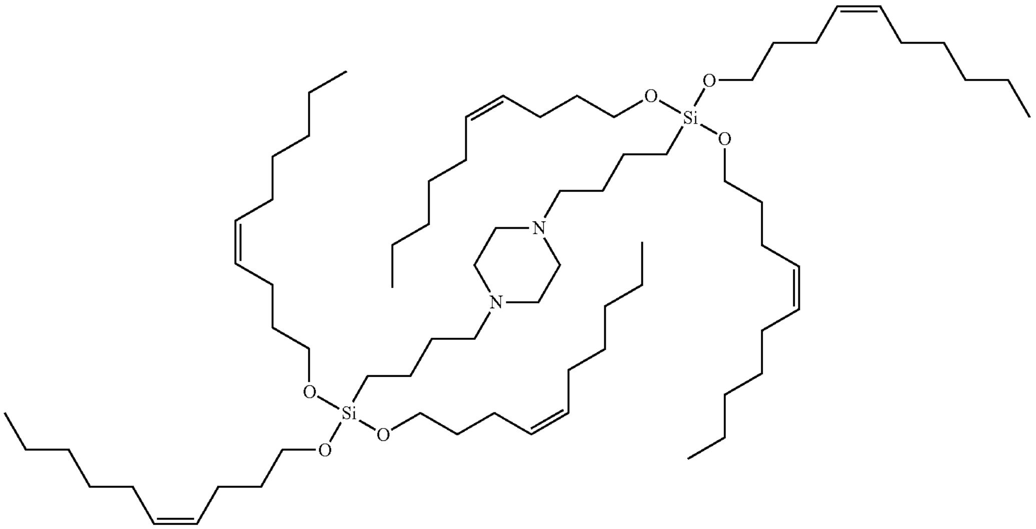
,
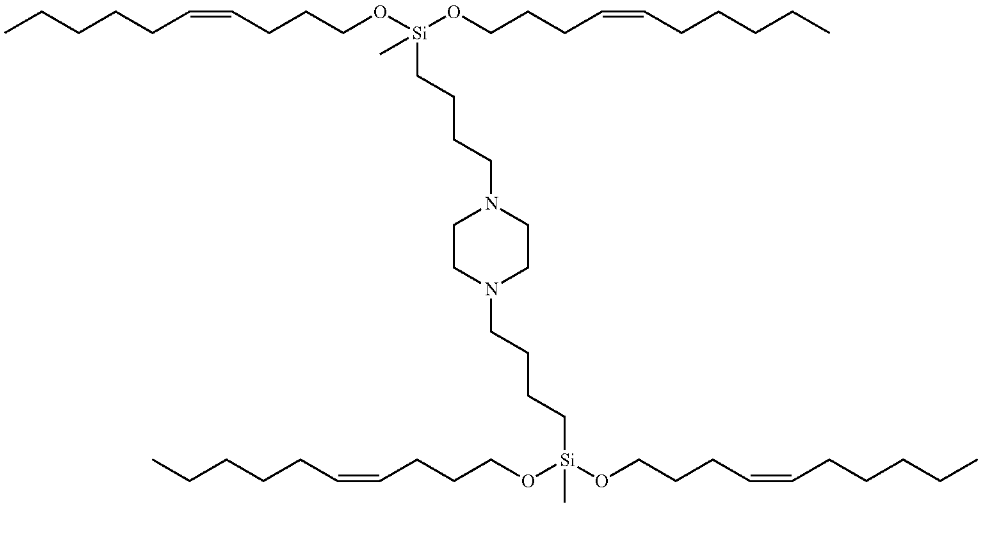
, -continued
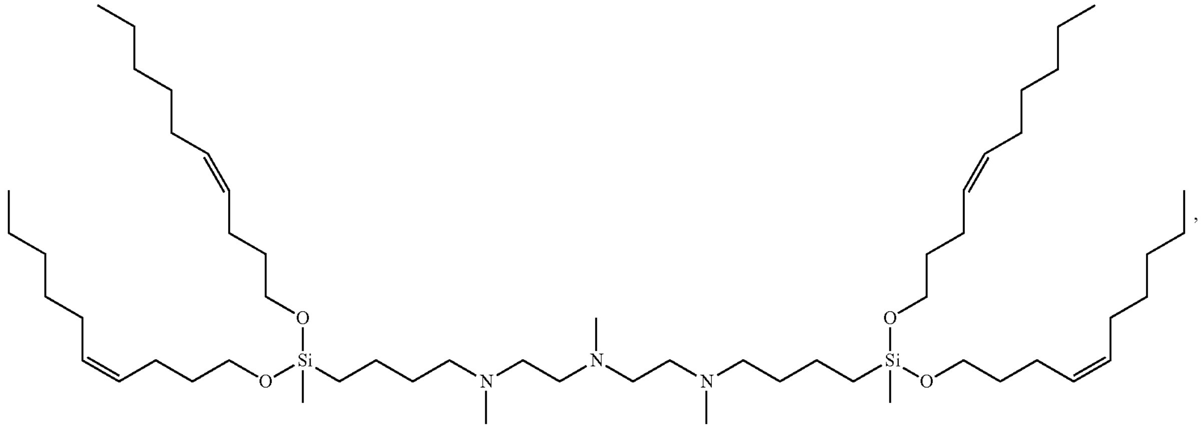
,
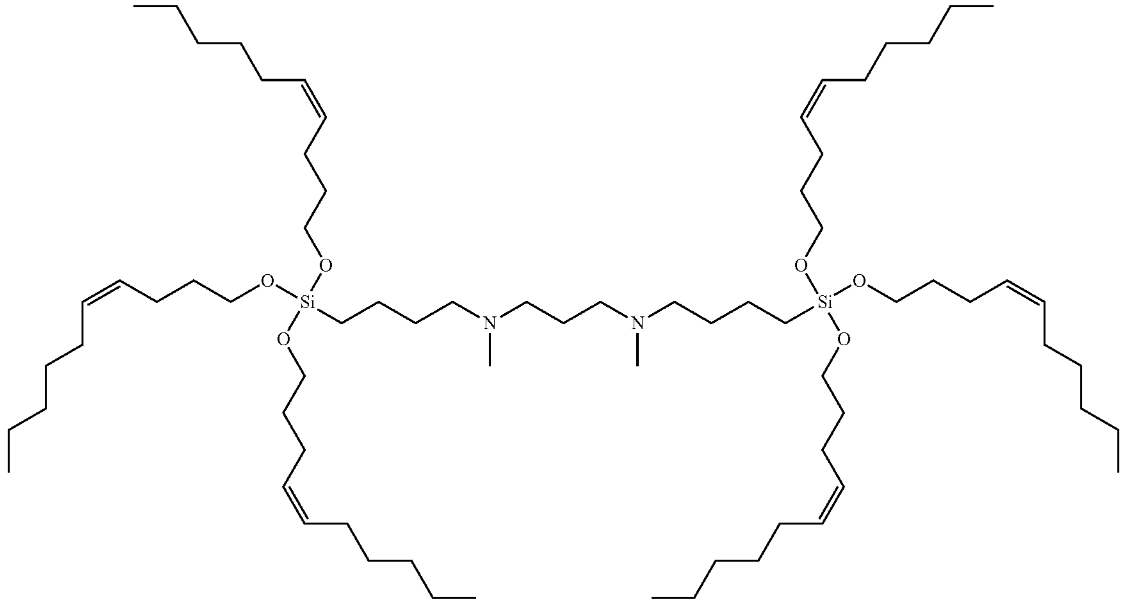
,
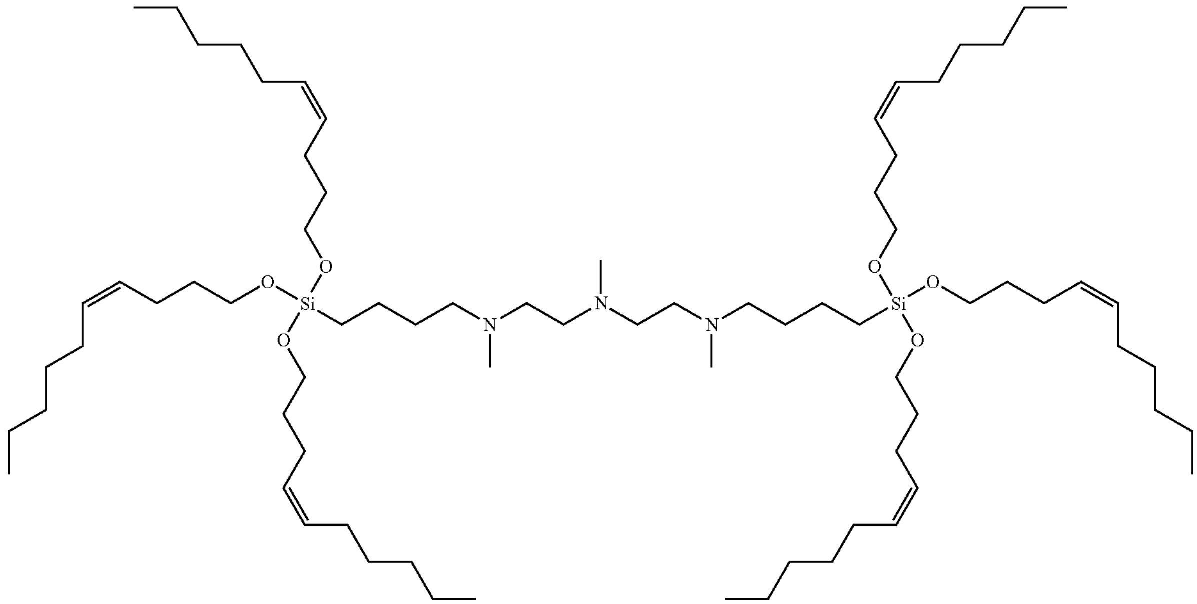
, -continued
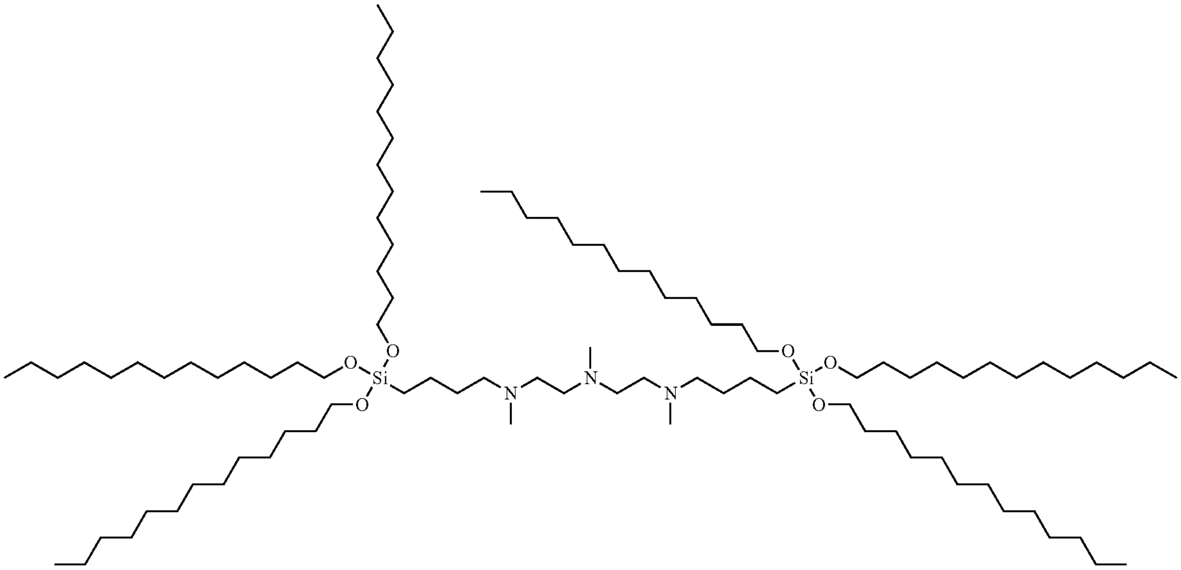
,
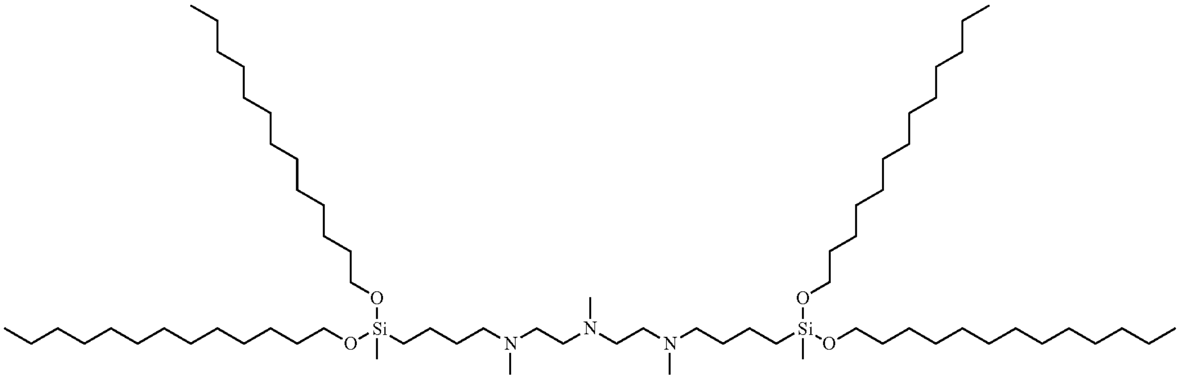
,
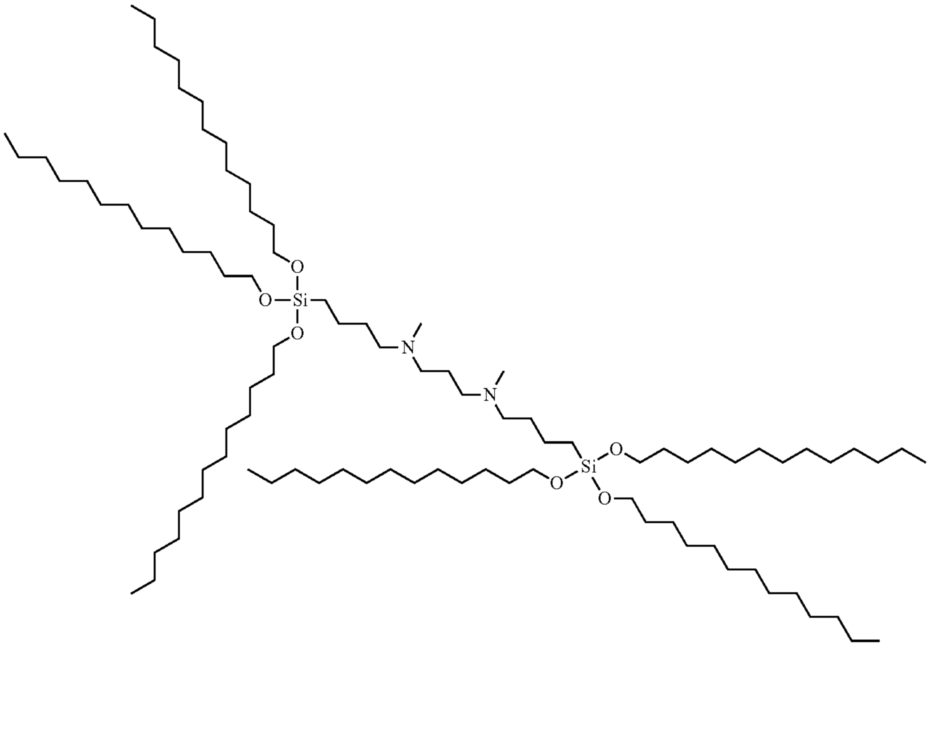
, -continued
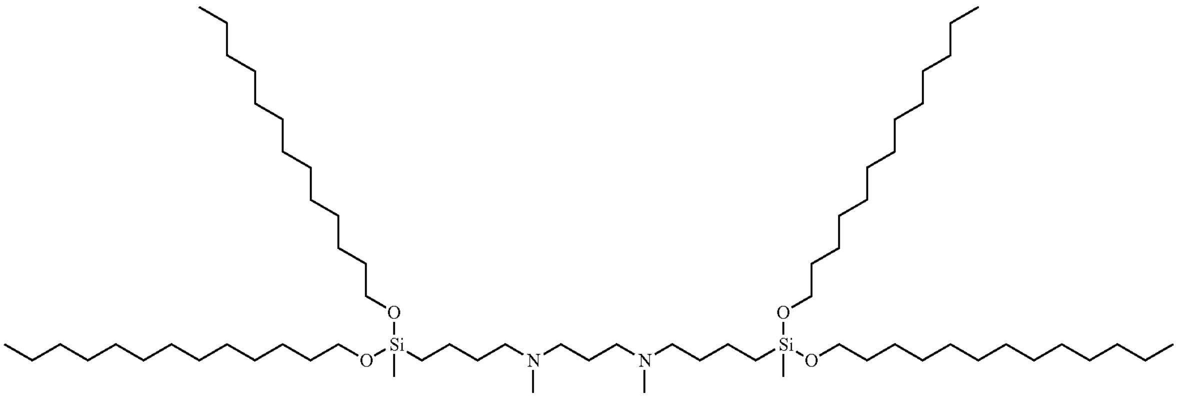
,
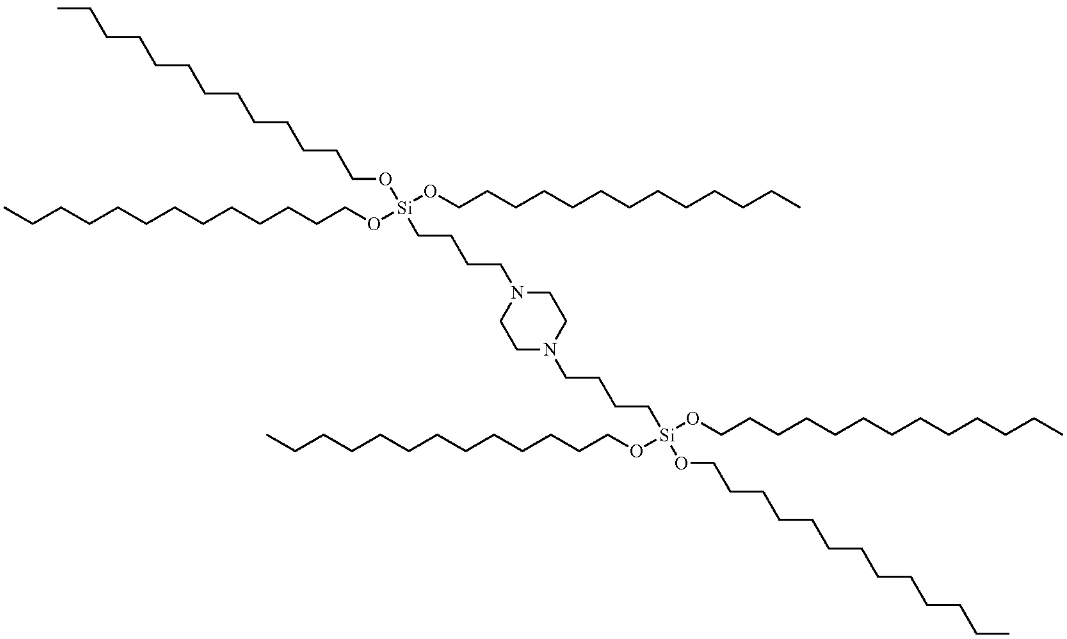
,
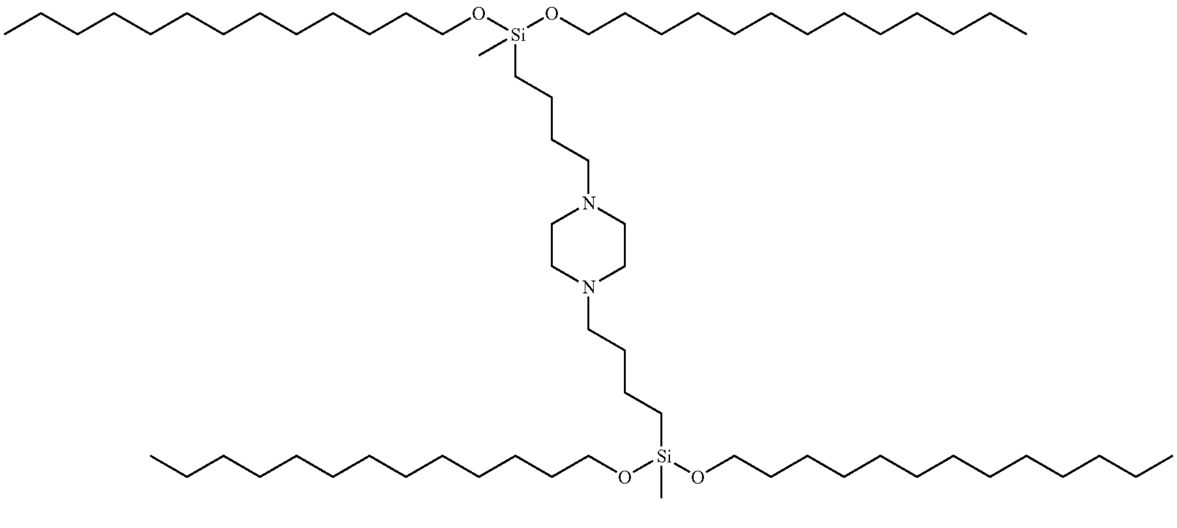
, -continued
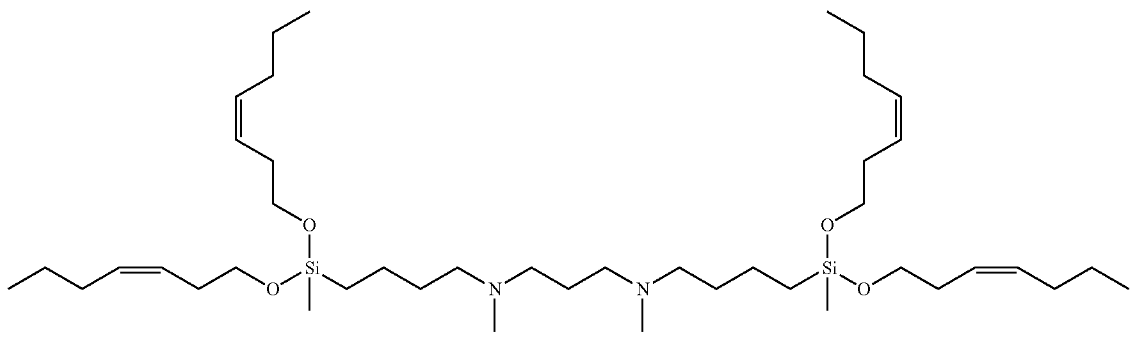
,
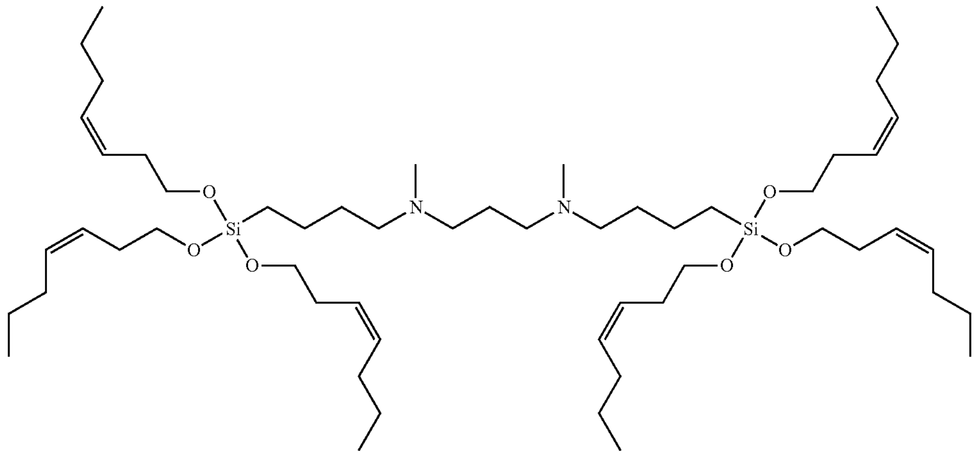
,
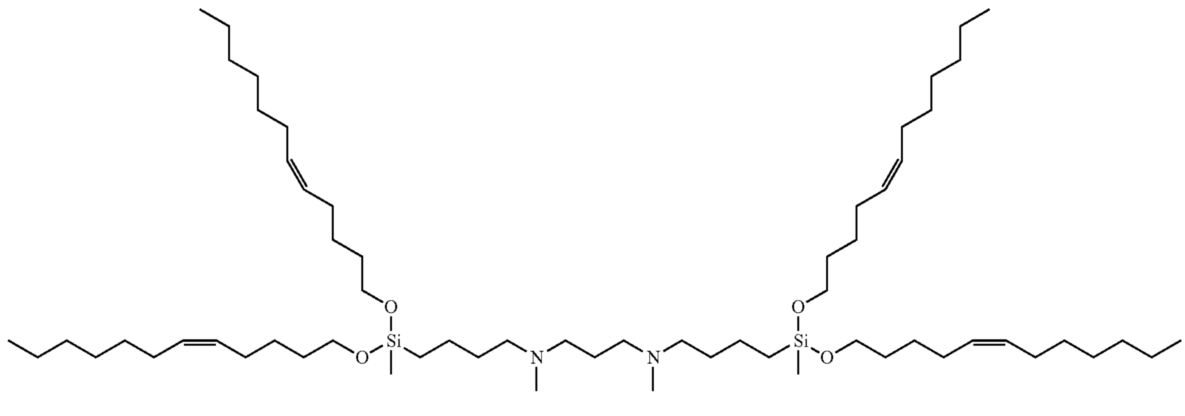
, -continued
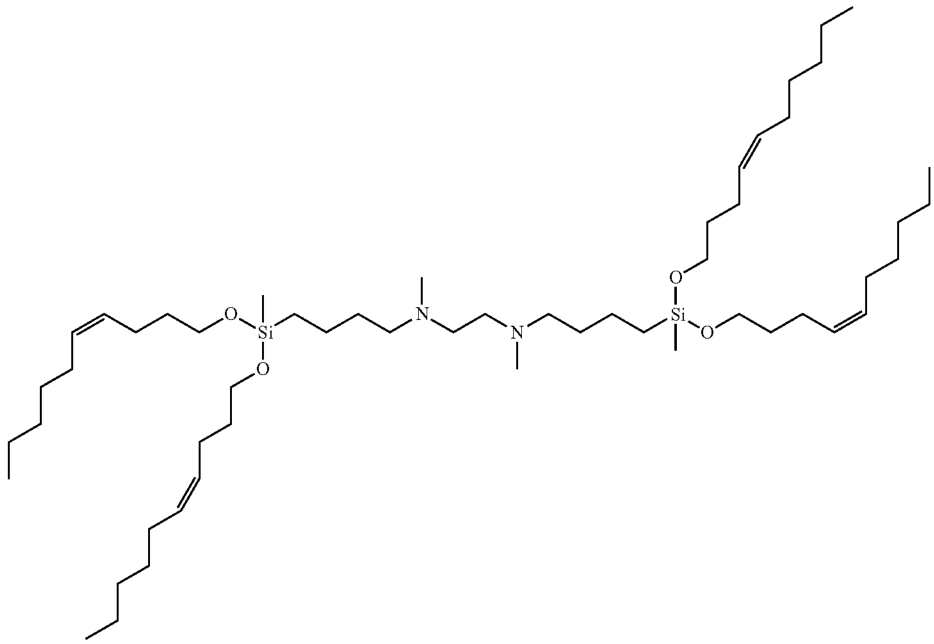
,
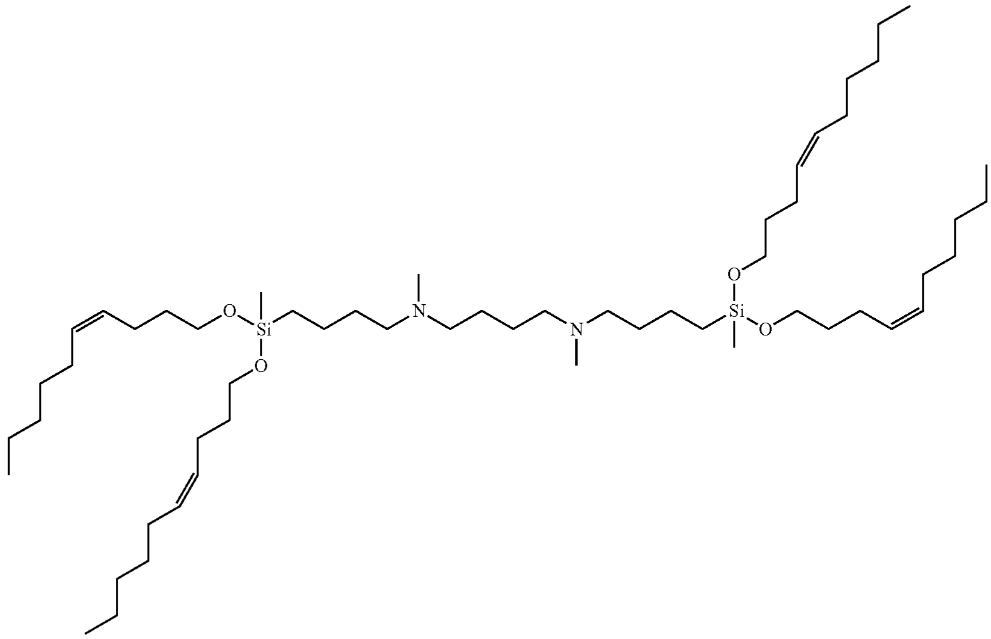
, -continued
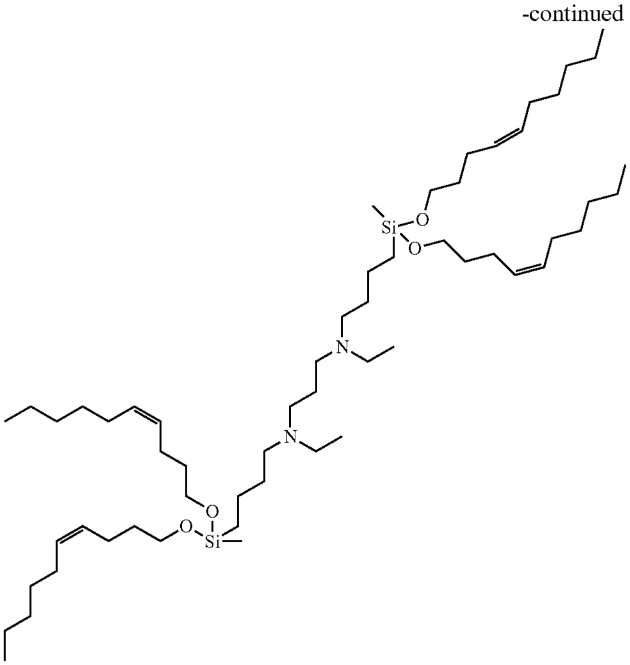
,
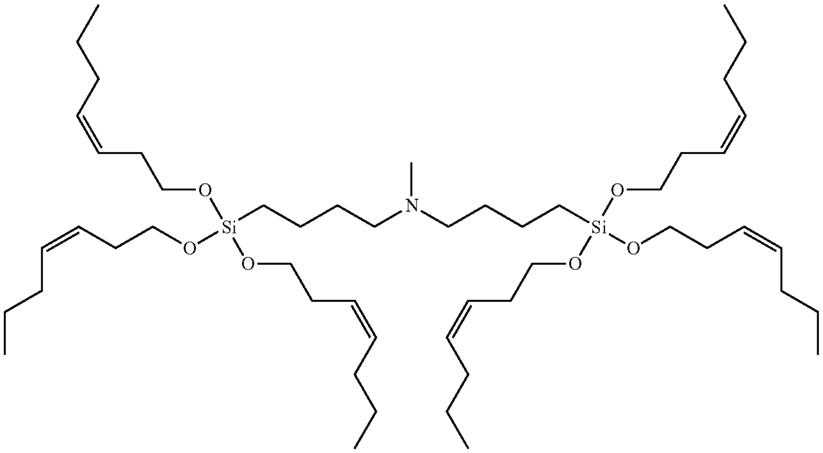
,
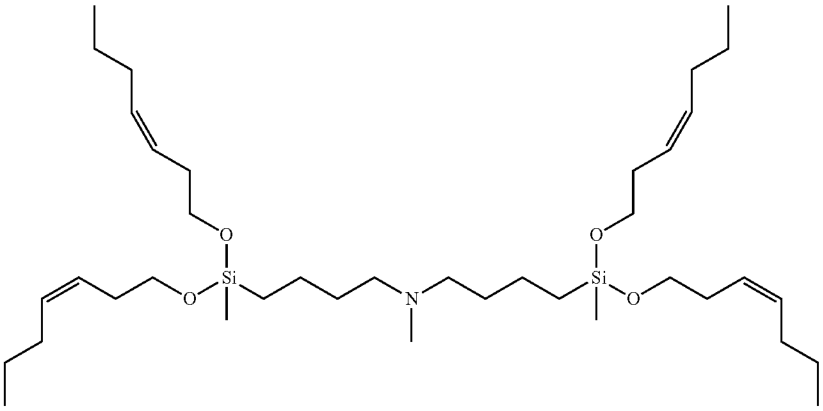
, -continued
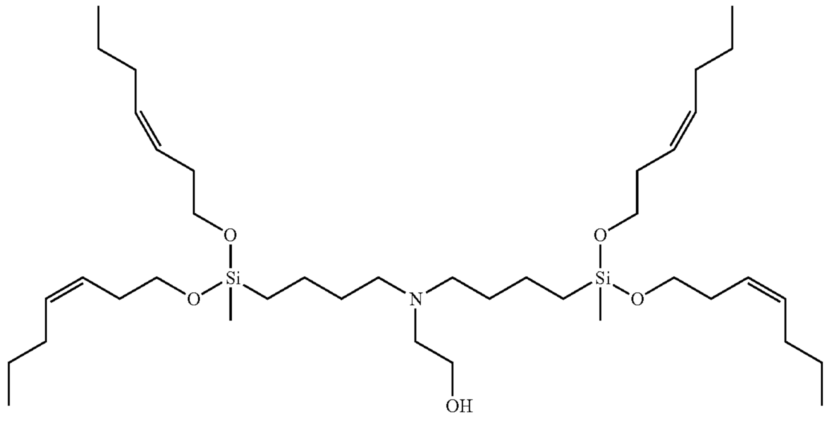
,
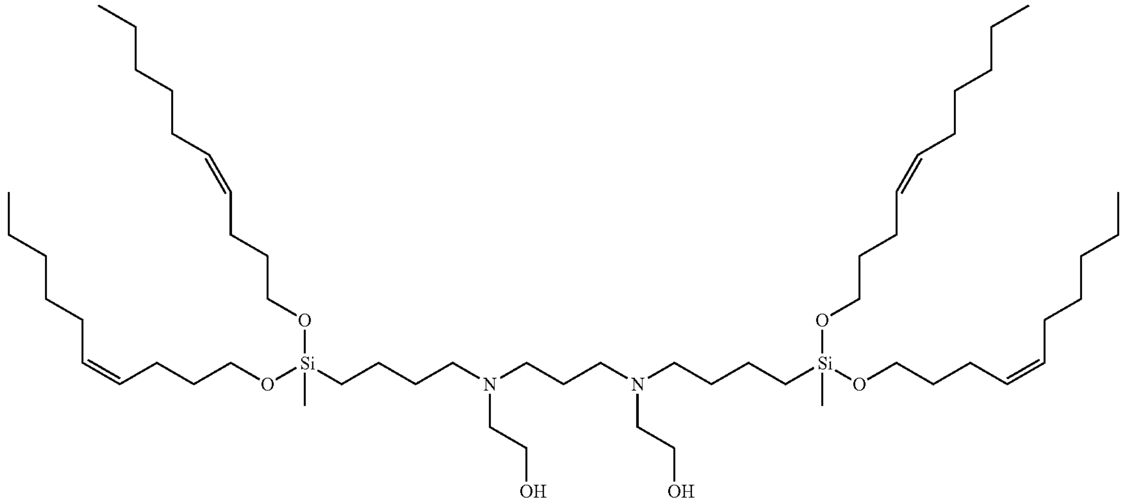
,
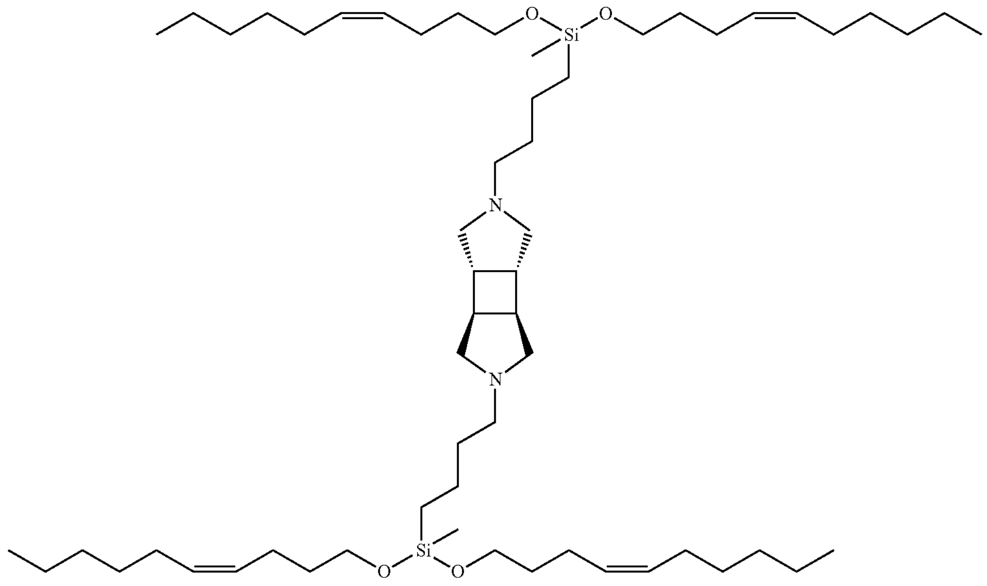
, -continued
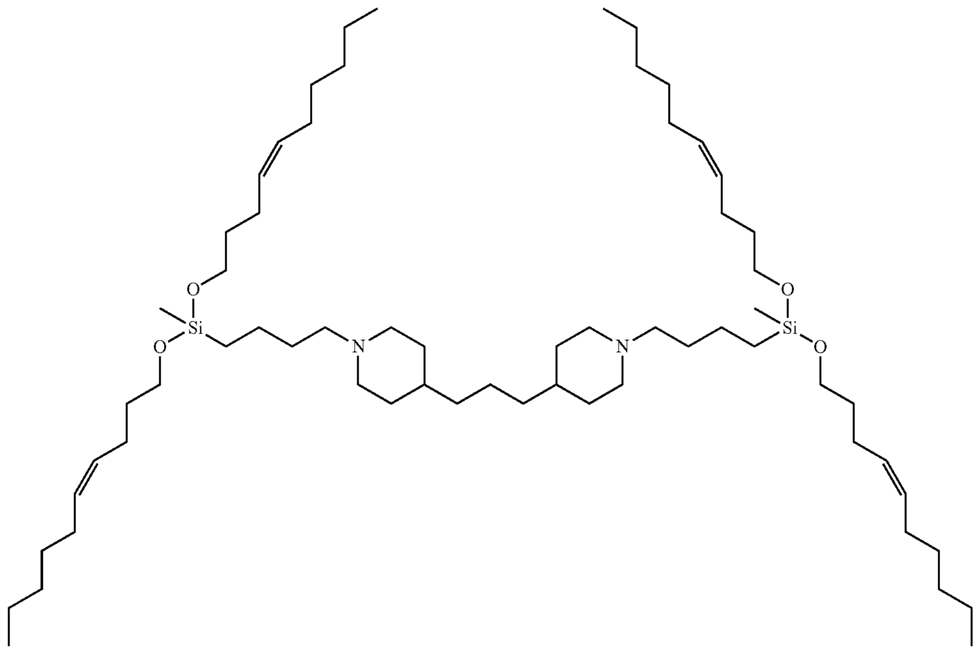
,
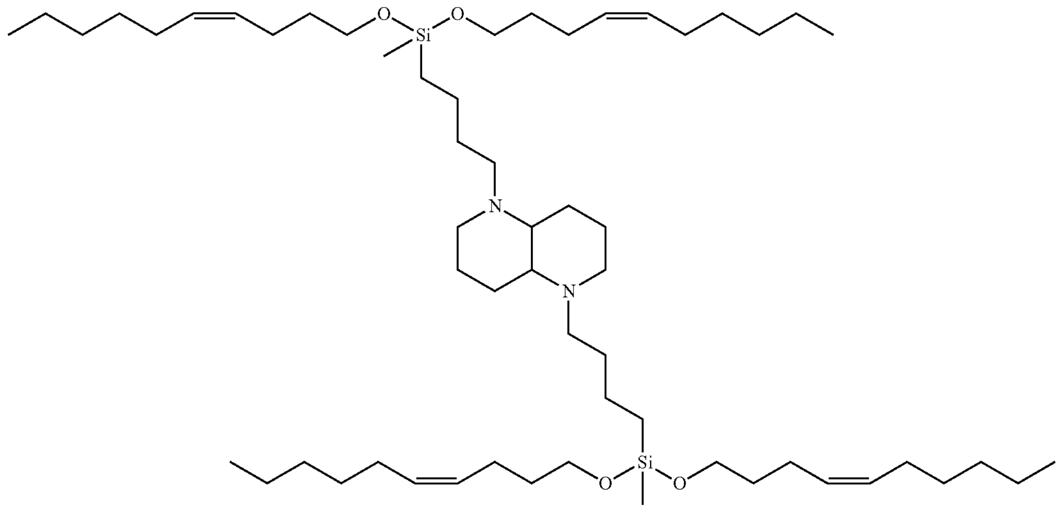
, -continued
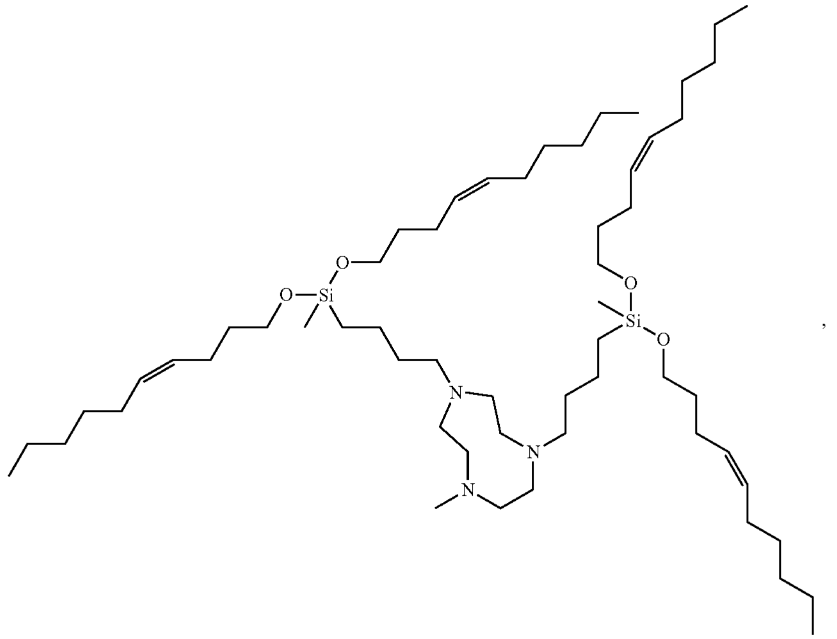
,
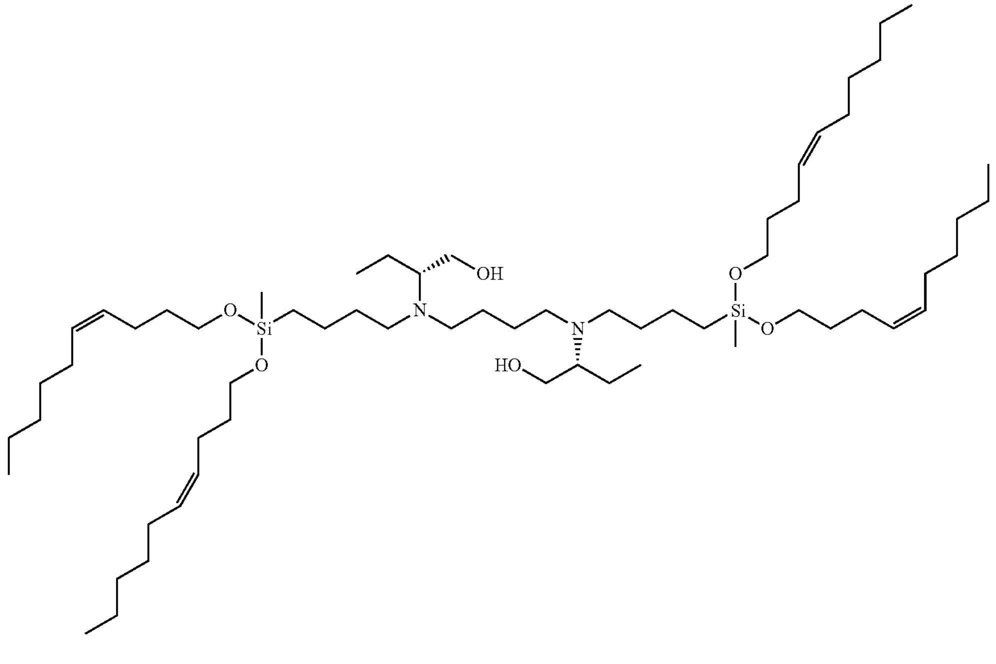
, -continued
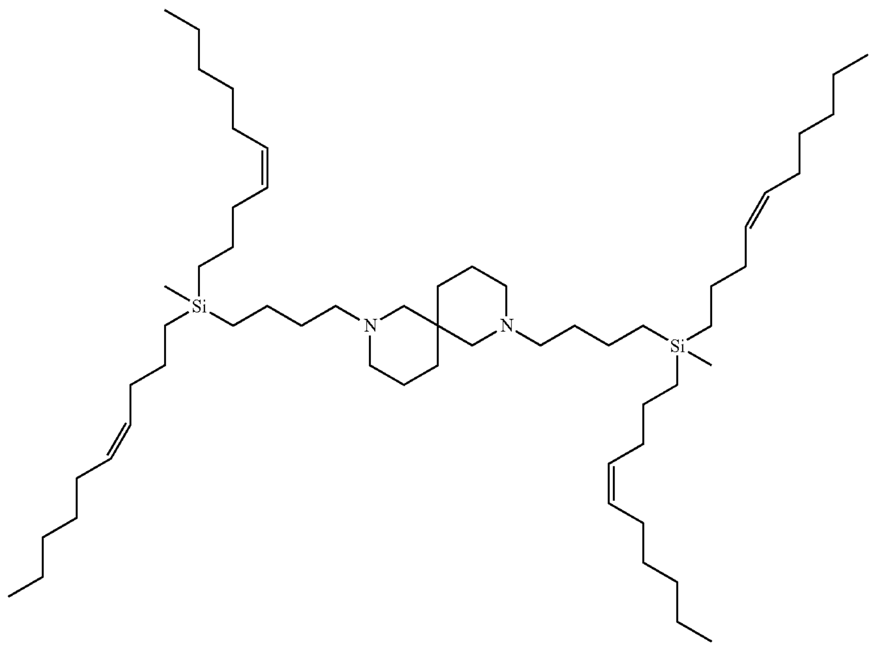
,
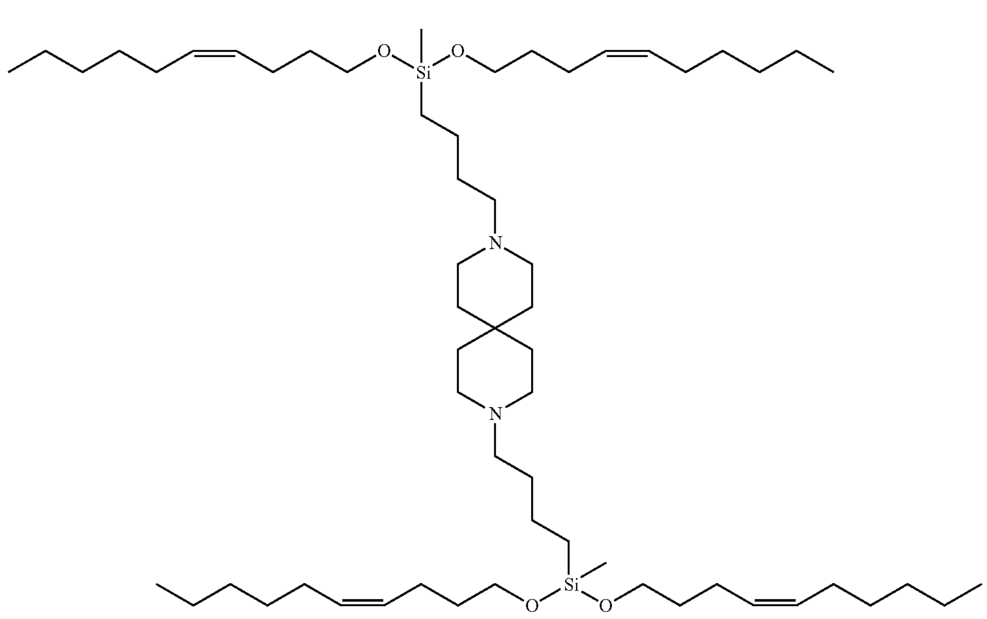
, and -continued

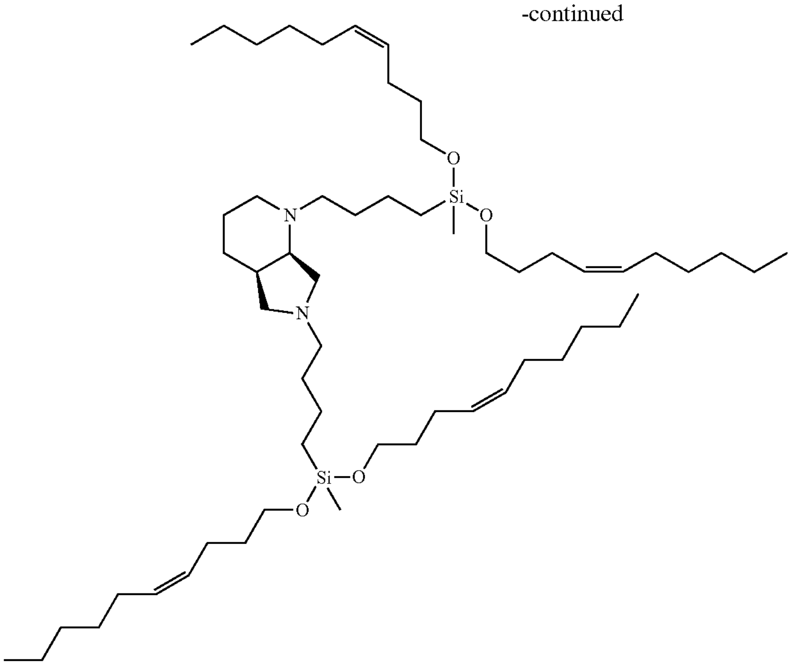

, or a salt thereof.

13. A lipid particle comprising the compound of claim 1.

14. The lipid particle of claim 13, wherein the lipid particle further comprises a therapeutic agent.

15. The lipid particle of claim 14, wherein the therapeutic agent is a nucleic acid therapeutic agent.

16. The lipid particle of claim 14, wherein the therapeutic agent is an interfering RNA agent.

17. The lipid particle of claim 16, wherein the therapeutic agent is siRNA.

18. The lipid particle of claim 14, wherein the therapeutic agent is mRNA.

19. A lipid particle comprising the compound of claim 12.

20. A composition comprising the compound of claim 1.

21. A composition comprising the compound of claim 12.

22. A pharmaceutical composition comprising the lipid particle of claim 13, and a pharmaceutically acceptable carrier.

23. A pharmaceutical composition comprising the lipid particle of claim 19, and a pharmaceutically acceptable carrier.

24. A method for the in vivo delivery of a therapeutic agent, the method comprising: administering to a mammalian subject the lipid particle of claim 14.

25. A method for treating a disease or disorder in a mammalian subject in need thereof, the method comprising:
administering to the mammalian subject a therapeutically effective amount of the lipid particle of claim 14.

26. The method of claim 25, wherein the disease or disorder is liver fibrosis.

27. The method of claim 25, wherein the disease or disorder is liver fibrosis associated non-alcoholic steatohepatitis (NASH) or alcoholic steatohepatitis (ASH).

28. A method of delivering a therapeutic agent to a hepatic stellate cell (HSC), in vivo or in vitro, comprising contacting the HSC with the lipid particle of claim 14.

29. A method for the in vivo delivery of a therapeutic agent, the method comprising: administering to a mammalian subject the lipid particle of claim 19, wherein the lipid particle further comprises the therapeutic agent.

30. A method for treating a disease or disorder in a mammalian subject in need thereof, the method comprising:
administering to the mammalian subject a therapeutically effective amount of the lipid particle of claim 19, wherein the lipid particle further comprises a therapeutic agent.

* * * * *